US012410405B2

United States Patent
Tom et al.

(10) Patent No.: US 12,410,405 B2
(45) Date of Patent: *Sep. 9, 2025

(54) ENHANCED MSC PREPARATIONS

(71) Applicant: Mesoblast International Sárl, Meyrin (CH)

(72) Inventors: Samson Tom, Basking Ridge, NJ (US); Christopher Ton, Lansdale, PA (US); Alla Danilkovitch, Columbia, MD (US)

(73) Assignee: Mesoblast International Sàrl, Meyrin (CH)

( * ) Notice: Subject to any disclaimer, the term of this patent is extended or adjusted under 35 U.S.C. 154(b) by 76 days.

This patent is subject to a terminal disclaimer.

(21) Appl. No.: 18/331,353

(22) Filed: Jun. 8, 2023

(65) Prior Publication Data
US 2024/0117315 A1 Apr. 11, 2024

Related U.S. Application Data

(60) Continuation of application No. 16/725,677, filed on Dec. 23, 2019, now Pat. No. 11,708,560, which is a continuation of application No. 15/945,148, filed on Apr. 4, 2018, now Pat. No. 10,550,369, which is a division of application No. 14/662,344, filed on Mar. 19, 2015, now Pat. No. 9,963,678, which is a division of application No. 14/138,265, filed on Dec. 23, 2013, now Pat. No. 9,828,586, which is a continuation of application No. 13/267,363, filed on Oct. 6, 2011, now abandoned.

(60) Provisional application No. 61/391,452, filed on Oct. 8, 2010, provisional application No. 61/391,482, filed on Oct. 8, 2010.

(51) Int. Cl.
| | |
|---|---|
| C12N 5/0775 | (2010.01) |
| A61K 35/12 | (2015.01) |
| A61K 35/28 | (2015.01) |
| A61K 41/00 | (2020.01) |
| A61K 47/69 | (2017.01) |
| A61K 49/04 | (2006.01) |
| A61K 49/18 | (2006.01) |
| A61P 37/06 | (2006.01) |
| B82Y 5/00 | (2011.01) |
| A61M 37/00 | (2006.01) |

(52) U.S. Cl.
CPC ............ C12N 5/0663 (2013.01); A61K 35/28 (2013.01); A61K 41/0038 (2013.01); A61K 41/0052 (2013.01); A61K 47/6901 (2017.08); A61K 49/0423 (2013.01); A61K 49/1827 (2013.01); A61P 37/06 (2018.01); B82Y 5/00 (2013.01); A61K 2035/122 (2013.01); A61M 37/00 (2013.01); C12N 2511/00 (2013.01)

(58) Field of Classification Search
None
See application file for complete search history.

(56) References Cited

U.S. PATENT DOCUMENTS

| | | |
|---|---|---|
| 5,197,985 A | 3/1993 | Caplan et al. |
| 5,226,914 A | 7/1993 | Caplan et al. |
| 5,486,359 A | 1/1996 | Caplan et al. |
| 5,591,625 A | 1/1997 | Gerson et al. |
| 5,643,736 A | 7/1997 | Bruder et al. |
| 5,733,542 A | 3/1998 | Haynesworth et al. |
| 5,736,396 A | 4/1998 | Bruder et al. |
| 5,811,094 A | 9/1998 | Caplan et al. |
| 5,827,740 A | 10/1998 | Pittenger |
| 5,837,539 A | 11/1998 | Caplan et al. |
| 5,855,619 A | 1/1999 | Caplan et al. |
| 5,908,782 A | 6/1999 | Marshak et al. |
| 5,908,784 A | 6/1999 | Johnstone et al. |
| 5,942,225 A | 8/1999 | Bruder et al. |
| 5,965,436 A | 10/1999 | Thiede et al. |
| 6,010,696 A | 1/2000 | Caplan et al. |
| 6,022,540 A | 2/2000 | Bruder et al. |
| 6,030,836 A | 2/2000 | Thiede et al. |
| 6,087,113 A | 7/2000 | Caplan et al. |
| 6,149,906 A | 11/2000 | Mosca |
| 6,174,333 B1 | 1/2001 | Kadiyala et al. |
| 6,225,119 B1 | 5/2001 | Qasba et al. |
| 6,251,295 B1 | 6/2001 | Johnson |
| 6,255,112 B1 | 7/2001 | Thiede et al. |

(Continued)

FOREIGN PATENT DOCUMENTS

| | | |
|---|---|---|
| CA | 2473108 A1 | 7/2003 |
| CA | 2736353 A1 | 2/2010 |

(Continued)

OTHER PUBLICATIONS

Augello, A., et al. "The Regulation of Differentiation in Mesenchymal Stem Cells," Hum Gene Ther 21(10):1226-1238, Mary Ann Liebert Inc., United States (Sep. 2010).

(Continued)

*Primary Examiner* — Daniel C Gamett

(74) *Attorney, Agent, or Firm* — Sterne, Kessler, Goldstein &Fox P.L.L.C.

(57) ABSTRACT

The present invention provides preparations of MSCs with important therapeutic potential. The MSC cells are non-primary cells with an antigen profile comprising less than about 1.25% CD45+ cells (or less than about 0.75% CD45+), at least about 95% CD105+ cells, and at least about 95% CD166+ cells. Optionally, MSCs of the present preparations are isogenic and can be expanded ex vivo and cryopreserved and thawed, yet maintain a stable and uniform phenotype. Methods are taught here of expanding these MSCs to produce a clinical scale therapeutic preparations and medical uses thereof.

16 Claims, No Drawings

(56) References Cited

U.S. PATENT DOCUMENTS

| | | |
|---|---|---|
| 6,261,549 B1 | 7/2001 | Fernandez et al. |
| 6,281,012 B1 | 8/2001 | McIntosh et al. |
| 6,322,784 B1 | 11/2001 | Pittenger et al. |
| 6,328,960 B1 | 12/2001 | McIntosh et al. |
| 6,344,239 B1 | 2/2002 | Asai et al. |
| 6,355,239 B1 | 3/2002 | Bruder et al. |
| 6,368,636 B1 | 4/2002 | McIntosh et al. |
| 6,379,953 B1 | 4/2002 | Bruder et al. |
| 6,387,367 B1 | 5/2002 | Davis-Sproul et al. |
| 6,387,369 B1 | 5/2002 | Pittenger et al. |
| 6,541,024 B1 | 4/2003 | Kadiyala et al. |
| 6,653,134 B2 | 11/2003 | Prockop et al. |
| 6,685,936 B2 | 2/2004 | McIntosh et al. |
| 6,709,864 B1 | 3/2004 | Pittenger et al. |
| 6,761,887 B1 | 7/2004 | Kavalkovich et al. |
| 6,797,269 B2 | 9/2004 | Mosca et al. |
| 6,835,377 B2 | 12/2004 | Goldberg et al. |
| 6,863,900 B2 | 3/2005 | Kadiyala et al. |
| 6,875,430 B2 | 4/2005 | McIntosh et al. |
| 6,936,281 B2 | 8/2005 | Seshi |
| 6,974,571 B2 | 12/2005 | Prockop et al. |
| 7,078,230 B2 | 7/2006 | Wilkison et al. |
| 7,101,704 B1 | 9/2006 | Mosca |
| 7,153,500 B2 | 12/2006 | Qasba et al. |
| 7,364,900 B2 | 4/2008 | Black et al. |
| 7,491,388 B1 | 2/2009 | McIntosh et al. |
| 7,514,074 B2 | 4/2009 | Pittenger et al. |
| 7,732,203 B2 | 6/2010 | Suh et al. |
| 7,892,829 B2 | 2/2011 | Pittenger et al. |
| 8,105,580 B2 | 1/2012 | Fraser et al. |
| 8,142,773 B2 | 3/2012 | Aslan et al. |
| 8,147,824 B2 | 4/2012 | Maziarz et al. |
| 8,158,120 B2 | 4/2012 | Pittenger et al. |
| 8,158,121 B2 | 4/2012 | Pittenger et al. |
| 8,404,229 B2 | 3/2013 | Fraser et al. |
| 8,440,177 B2 | 5/2013 | Gonzalez De La Pena et al. |
| 8,486,695 B2 | 7/2013 | Danilkovitch et al. |
| 8,637,004 B2 | 1/2014 | Danilkovitch et al. |
| 8,852,570 B2 | 10/2014 | Pittenger et al. |
| 8,852,571 B2 | 10/2014 | Pittenger et al. |
| 8,852,572 B2 | 10/2014 | Pittenger et al. |
| 8,852,573 B2 | 10/2014 | Pittenger et al. |
| 8,852,574 B2 | 10/2014 | Pittenger et al. |
| 8,852,575 B2 | 10/2014 | Pittenger et al. |
| 8,940,293 B2 | 1/2015 | Li et al. |
| 8,962,318 B2 | 2/2015 | Lim et al. |
| 9,050,178 B2 | 6/2015 | Barry et al. |
| 9,095,562 B2 | 8/2015 | Centeno et al. |
| 9,301,978 B2 | 4/2016 | Itescu et al. |
| 9,694,035 B2 | 7/2017 | Aggarwal et al. |
| 9,814,580 B2 | 11/2017 | Barry et al. |
| 9,828,586 B2 | 11/2017 | Tom et al. |
| 9,943,547 B2 | 4/2018 | Aggarwal et al. |
| 9,963,678 B2 | 5/2018 | Tom et al. |
| 10,105,394 B2 | 10/2018 | Itescu et al. |
| 10,206,951 B2 | 2/2019 | Bernard |
| 10,550,369 B2 | 2/2020 | Tom et al. |
| 10,668,101 B2 | 6/2020 | Aggarwal et al. |
| 10,716,814 B2 | 7/2020 | Aggarwal et al. |
| 10,729,727 B2 | 8/2020 | Aggarwal et al. |
| 10,828,334 B1 | 11/2020 | Aggarwal et al. |
| 10,849,932 B2 | 12/2020 | Itescu et al. |
| 10,960,025 B2 | 3/2021 | Aggarwal et al. |
| 11,389,484 B2 | 7/2022 | Aggarwal et al. |
| 11,491,188 B2 | 11/2022 | Itescu et al. |
| 11,708,560 B2 | 7/2023 | Tom et al. |
| 11,821,004 B2 | 11/2023 | Danilkovitch et al. |
| 12,115,194 B2 | 10/2024 | Itescu et al. |
| 2002/0037278 A1 | 3/2002 | Ueno et al. |
| 2002/0044923 A1 | 4/2002 | Mosca et al. |
| 2002/0064519 A1 | 5/2002 | Bruder et al. |
| 2003/0026786 A1 | 2/2003 | Pittenger et al. |
| 2003/0118567 A1 | 6/2003 | Stewart |
| 2003/0165482 A1 | 9/2003 | Roland et al. |
| 2004/0018174 A1 | 1/2004 | Palasis |
| 2004/0033214 A1 | 2/2004 | Young et al. |
| 2004/0166097 A1 | 8/2004 | Prockop et al. |
| 2004/0241145 A1 | 12/2004 | Hata et al. |
| 2005/0008626 A1 | 1/2005 | Fraser et al. |
| 2005/0031600 A1 | 2/2005 | Mickle et al. |
| 2005/0048035 A1 | 3/2005 | Fraser et al. |
| 2005/0048036 A1 | 3/2005 | Hedrick et al. |
| 2005/0095228 A1 | 5/2005 | Fraser et al. |
| 2005/0153442 A1 | 7/2005 | Katz et al. |
| 2005/0158397 A1 | 7/2005 | Chopp et al. |
| 2005/0260174 A1 | 11/2005 | Fraser et al. |
| 2005/0260175 A1 | 11/2005 | Hedrick et al. |
| 2006/0083720 A1 | 4/2006 | Fraser et al. |
| 2006/0110825 A1 | 5/2006 | Alessandri et al. |
| 2006/0275272 A1 | 12/2006 | Li et al. |
| 2007/0036768 A1 | 2/2007 | Fraser et al. |
| 2007/0123996 A1 | 5/2007 | Sugaya et al. |
| 2007/0253931 A1 | 11/2007 | Varney et al. |
| 2007/0258963 A1 | 11/2007 | Danilkovitch et al. |
| 2008/0175825 A1 | 7/2008 | Hampson et al. |
| 2008/0219957 A1 | 9/2008 | Lim et al. |
| 2008/0241113 A1 | 10/2008 | Walton et al. |
| 2009/0010896 A1 | 1/2009 | Centeno et al. |
| 2009/0169522 A1 | 7/2009 | Danilkovitch et al. |
| 2009/0180997 A1 | 7/2009 | Pittenger et al. |
| 2009/0208463 A1 | 8/2009 | Pittenger et al. |
| 2009/0214487 A1 | 8/2009 | Varney et al. |
| 2009/0220464 A1 | 9/2009 | Aggarwal et al. |
| 2009/0324609 A1 | 12/2009 | Lodie et al. |
| 2010/0034793 A1 | 2/2010 | Mcniece et al. |
| 2010/0040583 A1 | 2/2010 | Falanga |
| 2010/0068191 A1 | 3/2010 | Danilkovitch et al. |
| 2010/0166712 A1 | 7/2010 | Sadiq et al. |
| 2010/0330048 A1 | 12/2010 | Aggarwal et al. |
| 2011/0195054 A1 | 8/2011 | Cohen et al. |
| 2012/0052049 A1 | 3/2012 | Woods et al. |
| 2012/0087933 A1 | 4/2012 | Tom et al. |
| 2012/0201791 A1 | 8/2012 | Yoo et al. |
| 2012/0269774 A1 | 10/2012 | Ichim et al. |
| 2013/0330300 A1 | 12/2013 | Shi et al. |
| 2014/0112893 A1 | 4/2014 | Tom et al. |
| 2014/0161776 A1 | 6/2014 | Aggarwal et al. |
| 2014/0248244 A1 | 9/2014 | Danilkovitch et al. |
| 2015/0004693 A1 | 1/2015 | Danilkovitch et al. |
| 2015/0247122 A1 | 9/2015 | Tom et al. |
| 2015/0307844 A1 | 10/2015 | Sturm |
| 2016/0361362 A1 | 12/2016 | Koblar et al. |
| 2017/0106023 A1 | 4/2017 | Itescu et al. |
| 2017/0107495 A1 | 4/2017 | Itescu |
| 2017/0333482 A1 | 11/2017 | Itescu et al. |
| 2017/0340674 A1 | 11/2017 | Itescu et al. |
| 2018/0021380 A1 | 1/2018 | Han et al. |
| 2018/0037867 A1 | 2/2018 | Simmons et al. |
| 2018/0087032 A1 | 3/2018 | Danilkovitch et al. |
| 2019/0175657 A1 | 6/2019 | Aggarwal et al. |
| 2019/0201447 A1 | 7/2019 | Aggarwal et al. |
| 2019/0240259 A1 | 8/2019 | Aggarwal et al. |
| 2020/0197444 A1 | 6/2020 | Danilkovitch et al. |
| 2020/0231936 A1 | 7/2020 | Tom et al. |
| 2020/0325450 A1 | 10/2020 | Itescu et al. |
| 2020/0345781 A1 | 11/2020 | Honmou et al. |
| 2021/0163932 A1 | 6/2021 | Brink et al. |
| 2021/0169940 A1 | 6/2021 | Bernard |
| 2021/0171913 A1 | 6/2021 | Danilkovitch et al. |
| 2022/0079991 A1 | 3/2022 | Itescu |
| 2022/0143097 A1 | 5/2022 | Itescu et al. |
| 2022/0160776 A1 | 5/2022 | Itescu et al. |
| 2022/0226386 A1 | 7/2022 | Itescu |
| 2022/0275337 A1 | 9/2022 | Devine et al. |
| 2022/0364059 A1 | 11/2022 | Bukulmez et al. |
| 2023/0076630 A1 | 3/2023 | Aggarwal et al. |
| 2023/0089071 A1 | 3/2023 | Danilkovich et al. |
| 2023/0097931 A1 | 3/2023 | Itescu |
| 2023/0104108 A1 | 4/2023 | Itescu |
| 2023/0165904 A1 | 6/2023 | Itescu |
| 2023/0172991 A1 | 6/2023 | Itescu |
| 2023/0220349 A1 | 7/2023 | Simmons |
| 2023/0293589 A1 | 9/2023 | Itescu et al. |
| 2023/0293590 A1 | 9/2023 | Itescu et al. |

(56) References Cited

U.S. PATENT DOCUMENTS

| | | |
|---|---|---|
| 2023/0346846 A1 | 11/2023 | Itescu et al. |
| 2023/0398154 A1 | 12/2023 | Itescu et al. |
| 2024/0041934 A1 | 2/2024 | Itescu et al. |
| 2024/0091266 A1 | 3/2024 | Itescu et al. |
| 2024/0117315 A1 | 4/2024 | Tom et al. |
| 2024/0197787 A1 | 6/2024 | Itescu |
| 2024/0207323 A1 | 6/2024 | Itescu et al. |
| 2024/0301356 A1 | 9/2024 | Danilkovitch et al. |
| 2025/0032552 A1 | 1/2025 | Itescu |

FOREIGN PATENT DOCUMENTS

| | | |
|---|---|---|
| CN | 1382450 A | 12/2002 |
| CN | 1536075 A | 10/2004 |
| CN | 101210232 A | 7/2008 |
| CN | 111297899 A | 6/2020 |
| EP | 2476751 A1 | 7/2012 |
| EP | 3583945 A1 | 12/2019 |
| JP | H10501815 A | 2/1998 |
| JP | 2002510655 A | 4/2002 |
| WO | WO-9534320 A2 | 12/1995 |
| WO | WO-9630031 A1 | 10/1996 |
| WO | WO-9741208 A1 | 11/1997 |
| WO | WO-9951247 A1 | 10/1999 |
| WO | WO-0037111 A1 | 6/2000 |
| WO | WO-0049136 A1 | 8/2000 |
| WO | WO-0104268 A1 | 1/2001 |
| WO | WO-0126470 A1 | 4/2001 |
| WO | WO-03053346 A2 | 7/2003 |
| WO | WO-2004003164 A2 | 1/2004 |
| WO | WO-2004052177 A2 | 6/2004 |
| WO | WO-2004085630 A1 | 10/2004 |
| WO | WO-2005086922 A2 | 9/2005 |
| WO | WO-2005093044 A1 | 10/2005 |
| WO | WO-2006108229 A1 | 10/2006 |
| WO | WO-2006112365 A1 | 10/2006 |
| WO | WO-2006136244 A2 | 12/2006 |
| WO | WO-2007087139 A2 | 8/2007 |
| WO | WO-2007089798 A2 | 8/2007 |
| WO | WO-2007123363 A1 | 11/2007 |
| WO | WO-2007124594 A1 | 11/2007 |
| WO | WO-2007127408 A2 | 11/2007 |
| WO | WO-2008011133 A2 | 1/2008 |
| WO | WO-2008042174 A2 | 4/2008 |
| WO | WO-2008054825 A2 | 5/2008 |
| WO | WO-2008116157 A2 | 9/2008 |
| WO | WO-2008141177 A1 | 11/2008 |
| WO | WO-2009028870 A2 | 3/2009 |
| WO | WO-2010019886 A1 | 2/2010 |
| WO | WO-2010111522 A2 | 9/2010 |
| WO | WO-2012048093 A2 | 4/2012 |
| WO | WO-2013005053 A2 | 1/2013 |
| WO | WO-2013112942 A1 | 8/2013 |
| WO | WO-2015016761 A2 | 2/2015 |
| WO | WO-2015077624 A1 | 5/2015 |
| WO | WO-2015089280 A1 | 6/2015 |
| WO | WO-2016086020 A1 | 6/2016 |
| WO | WO-2016102601 A1 | 6/2016 |
| WO | WO-2017144552 A1 | 8/2017 |
| WO | WO-2017165641 A1 | 9/2017 |
| WO | WO-2018202853 A1 | 11/2018 |
| WO | WO-2019051623 A1 | 3/2019 |
| WO | WO-2019102268 A1 | 5/2019 |
| WO | WO-2020141473 A1 | 7/2020 |
| WO | WO-2020141483 A1 | 7/2020 |
| WO | WO-2020157660 A1 | 8/2020 |
| WO | WO-2020234450 A1 | 11/2020 |
| WO | WO-2021024207 A1 | 2/2021 |
| WO | WO-2021165420 A1 | 8/2021 |
| WO | WO-2021176001 A1 | 9/2021 |
| WO | WO-2021180850 A1 | 9/2021 |
| WO | WO-2021180851 A1 | 9/2021 |
| WO | WO-2021198454 A1 | 10/2021 |
| WO | WO-2022034506 A1 | 2/2022 |
| WO | WO-2022132986 A2 | 6/2022 |
| WO | WO-2022159731 A1 | 7/2022 |
| WO | WO-2023228153 A1 | 11/2023 |
| WO | WO-2024121818 A1 | 6/2024 |
| WO | WO-2024121819 A1 | 6/2024 |
| WO | WO-2024121820 A1 | 6/2024 |
| WO | WO-2024121821 A1 | 6/2024 |

OTHER PUBLICATIONS

Baksh, D., et al., "Adult mesenchymal stem cells: characterization, differentiation, and application in cell and gene therapy," J Cell Mol Med 8(3):301-316, Wiley-Blackwell Publishing Ltd., United Kingdom (Jul.-Sep. 2004).

Bernardo, M., et al., "Optimization of in vitro expansion of human multipotent mesenchymal stromal cells for cell-therapy approaches: further insights in the search for a fetal calf serum substitute," J Cell Physiol 211(1):121-130, Wiley-Liss Inc., United States (Apr. 2007).

Bieback, K., et al., "Clinical Protocols for the Isolation and Expansion of Mesenchymal Stromal Cells," Transfus Med Hemother 35(4):286-294, S. Krager AG, Switzerland (2008).

Bobis, S., et al., "Mesenchymal stem cells: characteristics and clinical applications," Folia Histochem Cytobiol 44(4):215-230, Via Medica, Poland (2006).

Both, S.K., et al., "A Rapid and Efficient Method for Expansion of Human Mesenchymal Stem Cells," Tissue Eng 13(1):3-9, Mary Ann Liebert, United States (Jan. 2007).

Colter, D. et al., "Rapid expansion of recycling stem cells in cultures of plastic-adherent cells from human bone marrow," Proc Natl Acad Sci USA 97(7):3213-3218, National Academy of Sciences, United States (Mar. 2000).

Falanga, V., et al., "Autologous Bone Marrow-Derived Cultured Mesenchymal Stem Cells Delivered in a Fibrin Spray Accelerate Healing in Murine and Human Cutaneous Wounds", Tissue Eng 13(6):1299-1312, Mary Ann Liebert, United States (Jun. 2007).

Gronthos, S., et al., "Surface Protein Characterization of Human Adipose Tissue-derived Stromal Cells," J Cell Physiol 189(1):54-63, Wiley-Liss, United States (Oct. 2001).

Guidance for FDA Reviewers and Sponsors, Content and Review of Chemistry, Manufacturing, and Control (CMS) Information for Human Gene Therapy Investigational New Drug Applications (INDs), Feb. 19, 2010.

Jiang, Y., et al., "Pluripotency of Mesenchymal Stem Cells Derived From Adult Marrow," Nature 418(6893):41-49, Nature Publishing Group, United Kingdom (Jul. 2002).

Kuznestov, S.A., et al., "Single-colony derived strains of human marrow stromal fibroblasts form bone after transplantation in vivo," J Bone Miner Res 12(9):1335-1347, Wiley, United States (Sep. 1997).

Le Blanc, K., et al., "Mesenchymal Stem Cells Inhibit the Expression of CD25 (Interleukin-2 Receptor) and CD38 on 7 Phytohaemagglutinin-Activated Lymphocytes," Scand J Immunol 60(3):307-315, Wiley-Blackwell Publishing Ltd., United Kingdom (Sep. 2004).

International Search Report and Written Opinion, PCT/US2011/055072, dated Apr. 20, 2012.

Office Action mailed Dec. 2, 2015, in U.S. Appl. No. 14/138,265, Tom et al., filed Dec. 23, 2013, 7 pages.

Office Action mailed Feb. 11, 2013, in United States Application No. for U.S. Appl. No. 13/267,363, Tom, S., et al., filed Oct. 6, 2011, 8 pages.

Office Action mailed Jul. 1, 2013, in United States Application No. for U.S. Appl. No. 13/267,363, Tom, S., et al., filed Oct. 6, 2011, 8 pages.

Office Action mailed Mar. 13, 2017, in U.S. Appl. No. 14/138,265, Tom et al., filed Dec. 23, 2013, 5 pages.

Office Action mailed Mar. 23, 2015, in U.S. Appl. No. 14/138,265, Tom et al., filed Dec. 23, 2013, 9 pages.

Peister, A., et al., "Adult stem cells from bone marrow (MSCs) isolated from different strains of inbred mice vary in surface epitopes, rates of proliferation, and differentiation potential," Blood 103(5):1662-1668, Elsevier BV, United States (Mar. 2004).

(56) References Cited

OTHER PUBLICATIONS

Pettenger. M.F., et al., "Multilineage potential of adult human mesenchymal stem cells," Science 284(5411):143-147, American Association for the Advancement of Science, United States (Apr. 1999).

Rayment, E.A., et al., "Concise Review: Mind the Gap: Challenges in Characterizing and Quantifying Cell- and Tissue-based Therapies for Clinical Translation," Stem Cells 28(5):996-1004, Oxford University Press, United Kingdom (May 2010).

Schallmoser, K., et al., "Rapid large-scale expansion of functional mesenchymal stem cells from unmanipulated bone marrow without animal serum," Tissue Eng Part C Methods 14(3):185-196, Mary Ann Liebert Inc., United States (Sep. 2008).

Tolar, J., et al., "Concise Review: Hitting the Right Spot with Mesenchymal Stromal Cells", Stem Cells 28(8):1446-1455, Oxford University Press, United States (Aug. 2010).

Wang, J.F., et al., "Mesenchymal stem/progenitor cells in human umbilical cord blood as support for ex vivo expansion of CD34+ hematopoietic stem cells and for chondrogenic differentiation," Haematologica 89(7):837-844, Ferrata Storti Foundation, Italy (Jul. 2004).

Woods, EJ., et al., "Container system for enabling commercial production of cryopreserved cell therapy products," Regen Med 5(4):659-667, Future Medicine Ltd., United Kingdom (Jul. 2010) abstract only.

Xiao et al., "Clonal Characterization of Bone Marrow Derived Stem Cells and Their Application for Bone Regeneration," Int J Oral Sci, 2(3):127-135, Sichuan University Press, China (Sep. 2010).

Zhukareva, V., et al., "Secretion profile of human bone marrow stromal cells: donor variability and response to inflammatory stimuli," Cytokine 50(3):317-321, Academic Press Inc., United States (Jun. 2010).

Zuk, P.A., et al., "Human adipose tissue is a source of multipotent stem cells," Mol Biol Cell 13(12):4279-95, American Society for Microbiology, United States (Dec. 2002).

Ramasamy, R., et al. "The immunosuppressive effects of human bone marrow-derived mesenchymal stem cells target T cell proliferation but not its effector function," Cell Immunol 251(2):131-136, Academic Press, United States (Feb. 2008).

Office Action mailed Sep. 14, 2016, in U.S. Appl. No. 14/662,344, Tom et al., filed Mar. 19, 2015, 8 pages.

Office Action mailed Jan. 7, 2016 in U.S. Appl. No. 14/662,344, Tom et al., filed Mar. 19, 2015, 8 pages.

Office Action mailed Mar. 29, 2017, in U.S. Appl. No. 14/662,344, Tom et al., filed Mar. 19, 2015, 5 pages.

Office Action mailed Aug. 2, 2017, in U.S. Appl. No. 14/662,344, Tom et al., filed Mar. 19, 2015, 5 pages.

Newman, R., et al., "Treatment of Inflammatory Diseases with Mesenchymal Stem Cells," Inflamm Allergy Drug Targets 8(2):110-123, Bentham Science Publishers Ltd., United Arab Emirates (Jun. 2009).

Chan, H., and Aggarwal, B. B., "Role of tumor necrosis factor receptors in the activation of nuclear factor kappa B in human histiocytic lymphoma U-937 cells," J Biol Chem 269(50):31424-31429, The American Society for Biochemistry and Molecular Biology Inc., United States (Dec. 1994).

Van Den Berk, L. C., et al., "Mesenchymal stem cells respond to TNF but do not produce TNF," J Leukoc Biol 87(2):283-289, Society for Leukocyte Biology, United States (published online Nov. 2009, published in print Feb. 2010).

Wang, H., et al., "Dexamethasone has variable effects on mesenchymal stromal cells," Cytotherapy 14(4):423-430, Elsevier, Netherlands (Apr. 2012).

Aggarwal, S., and Pittenger, M.F., "Human mesenchymal stem cells modulate allogeneic immune cell responses," Blood 105(4):1815-1822, American Society of Hematology, United States (Feb. 2005).

Kasakura, S., "[A role for T-helper type 1 and type 2 cytokines in the pathogenesis of various human diseases]," Rinsho Byori: The Japanese Journal of Clinical Pathology 46(9):915-921, Nihon Rinsho Byori Gakkai, Japan (1998).

Kosuge, T., et al., "[Effects of psidium components on cytokine productions in helper T cells and type-I allergy]," Yakugaku Zasshi (Journal of the Pharmaceutical Society of Japan) 120(4):408-412, Pharmaceutical Society of Japan, Japan (2000).

Miao, D., et al., "Megakaryocyte-bone marrow stromal cell aggregates demonstrate increased colony formation and alkaline phosphatase expression in vitro," Tissue Eng 10(5-6):807-817, Mary Ann Liebert, Inc., United States (May-Jun. 2004).

Takeba, Y., "[Functions and expression of Txk, a non-receptor tyrosine kinase of the Tec family]," BioMed Central, United Kingdom (2003).

Meisel, R., et al., "Human bone marrow stromal cells inhibit allogeneic T-cell responses by indoleamine 2,3-dioxygenase-mediated tryptophan degradation," Blood 103(12):4619-4621, American Society of Hematology, United States (Jun. 2004).

Ortiz, L.A., et al., "Mesenchymal stem cell engraftment in lung is enhanced in response to bleomycin exposure and ameliorates its fibrotic effects," Proc Natl Acad Sci USA 100(14):8407-8411, National Academy of Sciences, United States (Jul. 2003).

Al-Khaldi, A., et al., "Postnatal Bone Marrow Stromal Cells Elicit a Potent VEGF-dependent Neoangiogenic Response In Vivo," Gene Therapy 10(8):621-629, Nature Publishing Group, United Kingdom (Apr. 2003).

Al-Khaldi, A., et al., "Therapeutic Angiogenesis Using Autologous Bone Marrow Stromal Cells: Improved Blood Flow in a Chronic Limb Ischemia Model," Annals of Thoracic Surgery 75(1):204-209, Elsevier, Netherlands (Jan. 2003).

Barry, F.P and Murphy, J.M., "Mesenchymal Stem Cells: Clinical Application and Biological Characterization," Int J Biochem Cell Biol 36(4):568-584, Elsevier, Netherlands (Apr. 2004).

Barry, F.P., et al., "Biology and Clinical Applications of Mesenchymal Stem Cells," Birth Defects Res C Embryo Today 69(3):250-256, Wiley Periodicals, Inc., United States (Aug. 2003).

Battula, V.L., et al., "Human Placenta and Bone Marrow Derived MSC Cultured in Serum-free, B-FGF-containing Medium Express Cell Surface Frizzled-9 and SSEA-4 and Give Rise to Multilineage Differentiation," Differentiation 75(4):279-291, Elsevier, Netherlands (Apr. 2007).

Dahl, J.A., et al., "Genetic and Epigenetic Instability of Human Bone Marrow Mesenchymal Stem Cells Expanded in Autologous Serum or Fetal Bovine Serum," Int J Dev Biol 52(8):1033-1042, University of the Basque Country Press, Spain (2008).

Dayem, A.A., et al., "Production of Mesenchymal Stem Cells Through Stem Cell Reprogramming," Int J Mol Sci 20(8):1922, MDPI, Switzerland (Apr. 2019).

Deans, R.J and Moseley, A.B, "Mesenchymal Stem Cells: Biology and Potential Clinical Uses," Experimental Hematology 28(8):875-884, Elsevier, Netherlands (Aug. 2000).

Devine, S.M., et al., "Mesenchymal Stem Cells Distribute to a Wide Range of Tissues Following Systemic Infusion into Nonhuman Primates," Blood 101(8):2999-3001, American Society of Hematology, United States (Apr. 2003).

Dexter, T.M., et al., "Conditions Controlling the Proliferation of Haemopoietic Stem Cells in Vitro," J Cell Physiol 91(3):335-344, Wiley-Liss, United States (Jun. 1977).

Doucet, C., et al., "Platelet Lysates Promote Mesenchymal Stem Cell Expansion: A Safety Substitute for Animal Serum in Cell-based Therapy Applications," J Cell Physiol 205(2):228-236, Wiley-Liss, United States (Nov. 2005).

Fischer, U, M., et al., "Pulmonary Passage is a Major Obstacle for Intravenous Stem Cell Delivery: the Pulmonary First-pass Effect," Stem Cells Dev 18(5):683-92, Mary Ann Liebert, Inc., United States (Jun. 2009).

Francois, M., et al., "Cryopreserved Mesenchymal Stromal Cells Display Impaired Immunosuppressive Properties as a Result of Heat-shock Response and Impaired Interferon-γ Licensing," Cytotherapy 14(2):147-152, Elsevier Inc., United States (Feb. 2012).

Freshney, R.I., et al., Culture of Animal Cells: A Manual of Basic Technique, Edition 4, John Wiley & Sons, United States (2000).

Gartner, S and Kaplan, H.S, "Long-term Culture of Human Bone Marrow Cells, " Proc Natl Acad Sci USA America 77(8):4756-4759, National Academy of Sciences, United States (Aug. 1980).

(56) References Cited

OTHER PUBLICATIONS

Gronthos, S. and Simmons, P.J., "The Growth Factor Requirements of STRO-1-positive Human Bone Marrow Stromal Precursors Under Serum-deprived Conditions in Vitro," Blood 85(4):929-940, Elsevier, United States (Feb. 1995).
Gronthos, S., et al., "Molecular and Cellular Characterisation of Highly Purified Stromal Stem Cells Derived From Human Bone Marrow," J Cell Sci 116(Pt 9):1827-1835, Company of Biologists, United Kingdom (May 2003).
Guo, Z., et al., "Biological Features of Mesenchymal Stem Cells From Human Bone Marrow," Chinese Medical Journal 114(9):950-953, Wolters Kluwer-Medknow, China (Sep. 2001).
Hackney, J.A., et al., "A Molecular Profile of a Hematopoietic Stem Cell Niche," Proc Natl Acad Sci USA 99(20):13061-13066, National Academy of Press, United States (Oct. 2002).
Horwitz, E.M., et al., "Clarification of the Nomenclature for MSC: The International Society for Cellular Therapy Position Statement," Cytotherapy 7(5):393-395, Elsevier Inc., United States (2005).
Zhou, S. Z., et al., "Adeno-associated virus 2-mediated high efficiency gene transfer into immature and mature subsets of hematopoietic progenitor cells in human umbilical cord blood," J Exp Med 179(6):1867-1875, Rockefeller University Press, United States (Jun. 1994).
Zyuzkov, G.N., et al., "Effect of Dimethylsulfoxide on the Functions of Mesenchymal and Hemopoietic Precursors," Bull Exp Biol Med 143(4):535-538, Springer, United States (Apr. 2007).
Izadpanah, R., et al., "Biologic Properties of Mesenchymal Stem Cells Derived From Bone Marrow and Adipose Tissue," J Cell Biochem 99(5):1285-1297, Wiley-Liss, United States (Dec. 2006).
Jagasia, M.H., et al., "National Institutes of Health Consensus Development Project on Criteria for Clinical Trials in Chronic Graft-versus-host Disease: I. The 2014 Diagnosis and Staging Working Group Report," Biol Blood Marrow Transplant 21(3):389-401.e1, Carden Jennings Publishing, United States (Mar. 2015).
Krause, D.S., et al., "Multi-organ, Multi-lineage Engraftment by a Single Bone Marrow-derived Stem Cell," Cell 105(3):369-377, Cell Press, United States (May 2001).
Lange, C., et al., "Accelerated and Safe Expansion of Human Mesenchymal Stromal Cells in Animal Serum-free Medium for Transplantation and Regenerative Medicine," J Cell Physiol 213(1):18-26, Wiley-Liss, United States (Oct. 2007).
Le Blanc, K. and Ringden, O., "Immunobiology of Human Mesenchymal Stem Cells and Future Use in Hematopoietic Stem Cell Transplantation," Biol Blood Marrow Transplant 11(5):321-334, Carden Jennings Publishing, United States (May 2005).
Le Blanc, K., et al., "HLA Expression and Immunologic Properties of Differentiated and Undifferentiated Mesenchymal Stem Cells," Exp Hematol 31(10):890-896, Elsevier Science Inc, Netherlands (Oct. 2003).
Le Blanc, K., "Immunomodulatory Effects of Fetal and Adult Mesenchymal Stem Cells," Cytotherapy 5(6):485-489, Elsevier Inc., United States (2003).
Lennon, D.P., et al., "Human and Animal Mesenchymal Progenitor Cells From Bone Marrow: Identification of Serum for Optimal Selection and Proliferation," In Vitro Cellular & Developmental Biology 32(10):602-611, Springer New York, United States (Nov. 1996).
Lindner, U., et al., "Mesenchymal Stem or Stromal Cells: Toward a Better Understanding of Their Biology?" Transfus Med Hemother 37(2):75-83, S. Karger, Switzerland (Apr. 2010).
Lukomska, B., et al., "Challenges and Controversies in Human Mesenchymal Stem Cell Therapy," Stem cells international 2019: Article ID (9628536), SAGE-Hindawi Access to Research, United States (Apr. 2019).
Lv, F.J., et al., "Concise Review: the Surface Markers and Identity of Human Mesenchymal Stem Cells," Stem Cells 32(6):1408-1419, AlphaMed Press, United States (Jun. 2014).
McIntosh, K. and Bartholomew, A., "Stromal Cell Modulation of the Immune System," Graft Review 3(6):324-328, SAGE Publications, United States (2000).

Mesoblast Limited, "Mesoblast Heart Failure Cell Therapy Receives Orphan Drug Designation From FDA for Prevention of Gastrointestinal Bleeding in Patients With Left Ventricular Assist Devices," investorsmedia.mesoblast.com, accessed at URL: [http://investorsmedia.mesoblast.com/static-files/c08cebeb-456b-49d4-8e0d-cfc5dfllOd9e] on Mar. 31, 2020, 3 pages (Jun. 2019).
Muraki, K., et al., "Assessment of Viability and Osteogenic Ability of Human Mesenchymal Stem Cells After Being Stored in Suspension for Clinical Transplantation," Tissue Eng 12(6):1711-1719, Mary Ann Liebert, Inc, United States (Jun. 2006).
Pittenger, M.F., and Martin, B.J., "Mesenchymal Stem Cells and Their Potential as Cardiac Therapeutics," Circ Res 95(1):9-20, American Heart Association, United States (Jul. 2004).
Pittenger, M.F., et al., "Multilineage Potential of Adult Human Mesenchymal Stem Cells," Science 284(5411):143-147, American Association for the Advancement of Science, United States (Apr. 1999).
Prockop, D.J., "Marrow Stromal Cells as Stem Cells for Nonhematopoietic Tissues," Science 276(5309):71-74, American Association for the Advancement of Science, United States (Apr. 1997).
Rasmusson, I., "Immune Modulation by mesenchymal stem cells," Experimental Cell Research 312:2169-2179, Elsevier, Netherlands (Jul. 2006).
Sensebe, L., "Clinical Grade Production of Mesenchymal Stem Cells," Biomed Mater Eng 18(1 Suppl):S3-S10, IOS Press, Netherlands (2008).
Simmons, P.J. and Torok-Storb, B., "Identification of Stromal Cell Precursors in Human Bone Marrow by a Novel Monoclonal Antibody, STRO-1," Blood 78(1):55-62, Elsevier, United States (Jul. 1991).
Stute, N., et al., "Autologous Serum for Isolation and Expansion of Human Mesenchymal Stem Cells for Clinical Use," Exp Hematol 32(12):1212-1225, Elsevier Science Inc., Netherlands (Dec. 2004).
Takagi, M., et al., "In vitro Proliferation of Human Bone Marrow Mesenchymal Stem Cells Employing Donor Serum and Basic Fibroblast Growth Factor," Cytotechnology 43(1-3):89-96, Kluwer Academic Publishers, United States (Nov. 2003).
Thomas, R.J., et al., "Application of Process Quality Engineering Techniques to Improve the Understanding of the in Vitro Processing of Stem Cells for Therapeutic Use," J Biotechnol 136(3-4):148-155, Elsevier Science Publishers, Netherlands (Sep. 2008).
Tuli, R., et al., " Characterization of multipotential mesenchymal progenitor cells derived from human trabecular bone," Stem Cells, 21:681-693, Oxford Academic Press, United Kingdom (2003).
Ullah, I., et al., "Human mesenchymal stem cells—current trends and future prospective," Bioscience Reports 35(2):e00191, Springer, United States (Apr. 2015).
Wagers, A.J., et al., "Cell Fate Determination From Stem Cells," Gene Therapy 9(10):606-612, Nature Publishing Group, United Kingdom (May 2002).
Welter, J.F., et al., "Simplification of Aggregate Culture of Human Mesenchymal Stem Cells as a Chondrogenic Screening Assay," BioTechniques 42(6):732, 734-737, Eaton Publishing Company, United States (Jun. 2007).
Yamagiwa, S., et al., "A Role for TGF-ß in the Generation and Expansion of CD4+CD25+ Regulatory T Cells from Human Peripheral Blood," J Immunol 166(12):7282-7289, American Association of Immunologists, United States (Jun. 2001).
Co-pending U.S. Appl. No. 18/556,827, filed Apr. 22, 2022, inventor Itescu (Not Published).
Co-pending U.S. Appl. No. 18/556,845, filed Apr. 22, 2022, inventor Itescu (Not Published).
Animal Cell Culture: Practical Approach, Third Edition, ISBN 0199637970, Whole of Text (2000).
Gao, J., et al., "The Dynamic in Vivo Distribution of Bone Marrow-derived Mesenchymal Stem Cells After Infusion," Cells, Tissues, Organs 169(1):12-20, Karger, Switzerland (Apr. 2001).
Gronthos, S., et al., "A method to isolate and purify human bone marrow stromal stem cells," Methods Mol Biol., 449:45-57, Springer, Germany (2008).

(56) References Cited

OTHER PUBLICATIONS

Bartholomew, A., et al., "Mesenchymal Stem Cells Suppress Lymphocyte Proliferation In Vitro and Prolong Skin Graft Survival In Vivo," Experimental Hematology 30(1):42-48, Elsevier Science Inc., Netherlands (Jan. 2002).
Boston Scientific Corporation, "Boston Scientific and Osiris Therapeutics Announce Stem Cell Alliance, " accessed at URL:[www.ptca.org/press_rel/20030311pr_boston.html] on Apr. 12, 2023, 2 pages (Mar. 11, 2003).
Ikehara S., "Treatment of Autoimmune Diseases by a New Bone Marrow Transplantation Method," Clinical and Experimental Medicine 213(1): 96-98 (2005).
Burt, R.K., et al., "The Promise of Hematopoietic Stem Cell Transplantation for Autoimmune Diseases," Bone Marrow Transplantation 31(7):521-524, Nature Publishing Group, England (Apr. 2003).
Kong, Q., et al., "Administration of Bone Marrow Stromal Cells Ameliorates Experimental Autoimmune Myasthenia Gravis by Altering the Balance of Th1/Th2/Th17/Treg Cell Subsets Through the Secretion of TGF-beta," Journal of Neuroimmunology 207(1-2):83-91, Elsevier, Netherlands (Feb. 2009).
Di Nicola, M., et al., "Human Bone Marrow Stromal Cells Suppress T-Lymphocyte Proliferation Induced by Cellular or Nonspecific Mitogenic Stimuli," Blood 99(10):3838-3843, American Society of Hematology, United States (May 2002).
Djouad, F., et al., "Immunosuppressive Effect of Mesenchymal Stem Cells Favors Tumor Growth in Allogeneic Animals," Blood 102(10):3837-3844, American Society of Hematology, United States (Nov. 2003).
Dos Santos, F., et al., "Toward a Clinical-Grade Expansion of Mesenchymal Stem Cells from Human Sources: A Microcarrier-Based Culture System Under Xeno-Free Conditions," Tissue Eng Part C Methods. 17(12):1201-1210, Mary Ann Liebert, United States (Sep. 2011).
Eisenberg, C.A., et al., "Establishment of the mesodermal cell line QCE-6. A model system for cardiac cell differentiation," Circulation Research 78(2):205-216, Lippincott Williams & Wilkins, Untied States (Feb. 1996).
El-Badri, N.S., et al., "Mesenchymal Stem Cells in Autoimmune Disease," Stem Cells and Development 13(5):463-472, Mary Ann Liebert, United States (Oct. 2004).
Frassoni, F., et al., "Expanded Mesenchymal Stem Cells (MSC), Co-infused with HLA Identical Hemopoietic Stem Cell Transplants, Reduce Acute and Chronic Graft Versus Host Disease: a Matched Pair Analysis," Bone Marrow Transplant 29:S2 (2002).
Freshney, R.I., et al., Culture of Animal Cells: A Manual of Basic Technique, Edition 2, John Wiley & Sons, United States (1987).
Kushida, T., et al., "Crucial Role of Donor-derived Stromal Cells in Successful Treatment for Intractable Autoimmune Diseases in MRL/lpr Mice by Bmt via Portal Vein," Stem Cells 19(3):226-235, AlphaMed Press, United States (2001).
Prockop, D.J., and Olson, S.D., "Clinical trials with adult stem/progenitor cells for tissue repair: let's not overlook some essential precautions," Blood 109(8):3147-3151, American Society of Hematology, United States (Apr. 2007).
Prockop, D.J., et al., "Isolation and characterization of rapidly self-renewing stem cells from cultures of human marrow stromal cells" Cytotherapy 3(5):393-396, ISIS Medical Media, United Kingdom (Jan. 2001).
Kassem, M., "Mesenchymal Stem Cells: Biological Characteristics and Potential Clinical Applications," Cloning and Stem Cells 6(4):369-374, Mary Ann Liebert, Inc., United States (Dec. 2004).
Kebriaei, P., et al., "Adult Human Mesenchymal Stem Cells Added to Corticosteroid Therapy for the Treatment of Acute Graft-versus-Host Disease," Biol Blood Marrow Transplant 15:804-811, Elsevier, Netherlands (Jul. 2009).
Krebsbach, P.H., et al., "Bone Marrow Stromal Cells: Characterization and Clinical Application," Critical Reviews in Oral Biology and Medicine 10(2):165-181, International Association for Dental Research, United States (1999).
Lazarus, H., et al., "Role of Mesenchymal Stem Cells (MSC) in Allogeneic Transplantation: Early Phase I Clinical Result," Blood 96:392a, abstract 1691 (2000).
Le Blanc, K., et al., "Treatment of Severe Acute Graft-Versus-Host Disease With Third Party Haploidentical Mesenchymal Stem Cells," Lancet 363(9419): 1439-1441, Elsevier, England (May 2004).
Lucchini, G., et al., "Platelet-lysate-expanded Mesenchymal Stromal Cells as a Salvage Therapy for Severe Resistant Graft-versus-host Disease in a Pediatric Population," Biology of blood and marrow transplantation 16(9):1293-1301, Carden Jennings Publishing, United States (Mar. 2010).
Maitra, B., et al., "Human Mesenchymal Stem Cells Support Unrelated Donor Hematopoietic Stem Cells and Suppress T-cell Activation," Bone Marrow Transplant 33(6):597-604, Nature Publishing Group, United Kingdom (Mar. 2004).
See, F., et al., "Therapeutic effects of human STRO-3-selected mesenchymal precursor cells and their soluble factors in experimental myocardial ischemia," J Cell Mol Med 15(10):2117-29, Wiley, United States (Oct. 2011).
Shahdadfar, A., et al., "In Vitro Expansion of Human Mesenchymal Stem Cells: Choice of Serum Is a Determinant of Cell Proliferation, Differentiation, Gene Expression, and Transcriptome Stability," Stem Cells 23:1357-1366, Oxford University Press, United Kingdom (Aug. 2005).
Okamoto, R., et al., "Damaged Epithelia Regenerated by Bone Marrow-derived Cells in the Human Gastrointestinal Tract," Nature Medicine 8(9):1011-1017, Nature Publishing Company, United States (Sep. 2002).
Oskowitz, A., et al., "Serum-deprived human multipotent mesenchymal stromal cells (MSCs) are highly angiogenic," Stem Cell Research 6(3):215-225, Elsevier, Netherlands (Jan. 2011).
Spaggiari, G.M., et al., "Mesenchymal stem cells inhibit natural killer-cell proliferation, cytotoxicity, and cytokine production: role of indoleamine 2,3-dioxygenase and prostaglandin E2," Blood:111(3):1327-1332, American Society of Hematology, United States (Feb. 2008).
Pittenger, M. F., for Osiris Therapeutics, "Leaders in Stem Cell Medicine, Applications of Mesenchymal Stem Cells," Press Release, 2 pages (2001).
Prasad, A., et al., "Cytokine Detection in Culture Media Containing 10% FBS—A Comparison of Two Commonly Used Homogeneous High Throughput Assay Technologies," accessed at https://resources.perkinelmer.com/corporate/content/featured/sbs2009/pdfs/p7012%20-%20anu-alphalisa%20vs%20cisbio_15apr09.pdf Perkin Elmer, Inc., United States (Jan. 2009).
Serhan, C.N., et al., "Resolution of Inflammation: State of the Art, Definitions and Terms, " The FASEB Journal 21(2):325-332, The Federation, United States (Feb. 2007).
Sherer, Y and Shoenfeld, Y., "Autoimmune Diseases and Autoimmunity Post-bone Marrow Transplantation," Bone Marrow Transplantation 22:873-881, Stockton Press, United Kingdom (Nov. 1998).
Snowden, J.A., et al., "Long-term Outcome of Autoimmune Disease Following Allogeneic Bone Marrow Transplantation," Arthritis and Rheumatism 41(3):453-459, Wiley-Blackwell, United States (Mar. 1998).
Tse, W.T., et al., "Suppression of Allogeneic T-cell Proliferation by Human Marrow Stromal Cells: Implications in Transplantation," Transplantation 75(3):389-397, Lippincott Williams & Wilkins, United States (Feb. 2003).
Van Laar, J.M., et al., "Adult Stem Cells in the Treatment of Autoimmune Diseases," Rheumatology (Oxford) 45(10):1187-1193, Oxford University Press, England (Oct. 2006).
Wagner, W., et al., "Replicative Senescence of Mesenchymal Stem Cells: A Continuous and Organized Process," PLoS One 3(5):e2213, Public Library of Science, United States (May 2008).
Weng, J.Y., et al., "Mesenchymal stem cell as salvage treatment for refractory chronic GVHD," Bone marrow transplantation 45(12):1732-40, Nature Publishing Group, United Kingdom (Sep. 2010).
Spees, J. L., et al., "Internalized Antigens Must Be Removed to Prepare Hypoimmunogenic Mesenchymal Stem Cells for Cell and Gene Therapy," Molecular Therapy 9(5):747-756, American Society of Gene Therapy, United States (Mar. 2004).

(56) References Cited

OTHER PUBLICATIONS

Wagner, W., et al., "How to Track Cellular Aging of Mesenchymal Stromal Cells?," Aging 2(4):224-230, Impact Journals, United States (Apr. 2010).
Office Action mailed Oct. 18, 2022 in U.S. Appl. No. 16/725,677, Tom et al., filed Dec. 23, 2019, 8 pages.
Baxter Corporation, "Plasma-Lyte A (An Electrolyte Solution) Injection," Prescribing Information, 10 pages, revised Jun. 17, 2019, Baxter Corporation, Canada.
Co-pending Application, U.S. Appl. No. 18/711,167, inventor Itescu, S., filed May 17, 2024 (Not yet Published).
Co-pending Application, U.S. Appl. No. 18/872,445, inventor Itescu, S., filed Jun. 8, 2023 (Not yet Published).
Co-pending Application, U.S. Appl. No. 18/880,992, inventor Itescu, S., et al., filed Jan. 3, 2025 (Not yet Published).
Co-pending Application, U.S. Appl. No. 19/028,991, inventor Itescu, S., et al., filed Jan. 17, 2025 (Not yet Published).

ENHANCED MSC PREPARATIONS

CLAIM TO PRIORITY

This application is a continuation of U.S. patent application Ser. No. 16/725,677, filed Dec. 23, 2019, which is continuation of U.S. patent application of Ser. No. 15/945,148, filed Apr. 4, 2018 (now U.S. Pat. No. 10,550,369), which is a divisional of U.S. patent application Ser. No. 14/662,344, filed Mar. 19, 2015 (now U.S. Pat. No. 9,963,678), which is a divisional of U.S. patent application Ser. No. 14/138,265, filed Dec. 23, 2013 (now U.S. Pat. No. 9,828,586), which is a continuation of U.S. patent application Ser. No. 13/267,363, filed Oct. 6, 2011, now abandoned and claims the benefit of priority from U.S. Provisional Patent Application No. 61/391,452 entitled "Enhanced MSC Preparations," filed on Oct. 8, 2010, now expired, and U.S. Provisional Application No. 61/391,482, entitled "Nanoparticle-Loaded Cells," filed on Oct. 8, 2010, now expired, the contents of which are incorporated by reference in their entireties.

This application incorporates by reference, the International PCT Application No. PCT/US2011/055072 entitled "Enhanced MSC Preparations, which is incorporated by reference in its entirety.

TECHNICAL FIELD

The present invention generally relates to therapeutically effective preparations of mesenchymal stem cells (MSCs), methods for manufacturing such preparations, methods of screening and selecting such preparations, and therapeutic uses thereof.

BACKGROUND

One of the major problems in stem cell therapy is the lack of understanding of the therapeutic properties of stem cells, and how these therapeutic properties are influenced by manufacturing methods.

Stem cells are populations of cells found in embryos, fetuses, and adult tissues that are capable of self-renewal in undifferentiated forms and regain the capability of toti-, pluri- or multi-potential differentiation in conditioned environments.

Use of the term "stem" cell has generally been reserved for those cells possessing the ability to self-replicate and give rise to daughter cells which undergo a unidirectional, terminal differentiation process. Three adult tissues in which stem cells have been extensively studied include the epidermis, gastrointestinal epithelium, and the hematopoietic compartment of bone marrow. Of these, hematopoietic stem cells are perhaps the best characterized, and are noted for their ability to give rise to multiple cellular phenotypes through lineage progression of daughter progenitor cells.

The bone marrow stroma was originally thought to function mainly as a structural framework for the hematopoietic component of the marrow. Subsequently, it has become well established that the stroma consists of a heterogeneous population of cells, a subset of which exerts both positive and negative regulatory effects on the proliferation and differentiation of hematopoietic stem cells (HSC) in the marrow through a combination of physical and chemical signals. The stroma also contains other non-hematopoietic cells termed mesenchymal stem cells (MSC), which are capable of both self-renewal and differentiation into osteoblasts, adipocytes, myoblasts and chondroblasts. The number of HSCs in bone marrow is about 10-100 times greater than that of MSCs. MSCs also give rise to a variety of mature cell types via a step-wise maturation process similar to hematopoiesis, termed mesengenesis. Functions that have been attributed to MSCs include, for example, the daily control of inflammation, immune response, hematopoiesis and organ integrity.

Despite the features ascribed to MSC populations by their in vitro differentiation capabilities, the mechanisms governing their proliferation and multi-lineage differentiation capacity have been poorly understood. At the clonal level, there is little evidence for MSC self-renewal, therefore these cells might be termed multipotent progenitor cells. One of the greatest obstacles in the study of MSC biology is the heterogeneity of studied cell populations (Baksh et al. (2004) J Cell Mol Med 8, 301-16). For example, Pittenger et al. ((1999) Science 284, 143-7) found that the majority of human bone marrow derived MSCs are not pluripotent, while Kusnestov et al., ((1997) J Bone Miner Res 12, 1335-47) showed that only 58.8% of human MSCs had in vivo osteogenic potential. Others have shown that within the adipose derived populations of MSCs, cells with multi-lineage differentiation capability co-exist with single lineage committed cells (Zuk et al. (2002) Mol Biol Cell 13, 4279-95). Others have reported pluripotent progenitor cells (Jiang et al. (2002) Nature 418, 41-9).

Ex vivo preparations of bone marrow aspirates can show a great diversity of cell types. Even when such preparations are enriched for MSCs (e.g. by adherence), there is a remarkable diversity and heterogeneity. Methods exist in the art to enrich and expand such MSC's in culture, nonetheless, heterogeneity is observed at biochemical, genetic, and phenotypic levels.

Even so-called "pure MSC" preparations demonstrate heterogeneity with variation of therapeutic effect, potency, differentiation capacity, mitotic activity, and so forth. For example, MSCs are known to undergo phenotypic rearrangements during ex vivo manipulations, losing expression of some markers while acquiring new ones (Augello et al. "The Regulation of Differentiation in Mesenchymal Stem Cells" HUMAN GENE THERAPY 21:1226-1238 (October 2010)). Depending on culture conditions, various MSC subsets are preferentially expanded in culture, differing, for example, in expression of surface markers and other proteins, differentiation capacity, proliferation, and morphology (Baksh et al. "Adult mesenchymal stem cells: characterization, differentiation, and application in cell and gene therapy," J. Cell. Mol. Med. Vol 8, No 3, 2004 pp. 301-316; Bobis et al. "Mesenchymal stem cells: characteristics and clinical applications," FOLIA HISTOCHEMICA ET CYTOBIOLOGICA. Vol. 44, No. 4, 2006; pp. 215-230). Donor variability and donor tissue site also contribute to differences between preparation of cells (Zhukareva et al. "Secretion profile of human bone marrow stromal cells: donor variability and response to inflammatory stimuli," Cytokine, 2010, Volume: 50, Issue: 3, Pages: 317-321; US 2009/0010896).

Thus, it is clear that various observations attributed to "MSCs" by various laboratories are very likely describing different subsets of MSC populations, even when populations share certain functional properties typical of MSCs in general such as proliferative or differentiation capacity. For example, Xiao et al. describe a culture of bone marrow derived MSCs that has undergone 20 population doublings, exhibiting an antigen profile of less than 90% CD105+ cells and less than 85% CD166+ cells (Xiao et al. "Clonal Characterization of Bone Marrow Derived Stem Cells and Their Application for Bone Regeneration" Int J Oral Sci, 2(3): 127-135, 2010).

Changes of MSC cultures with passage (i.e. ex vivo expansion) are also well recognized. For example, in U.S. Pat. No. 5,486,359, Caplan describes that in his MSC preparations, early passaged cells (1st-2nd passages) gave more bone formation than late passaged cells (4th-6th passages).

This heterogeneity can be explained, in part, by the hypothesis that MSCs, with the ability to self-renew and differentiate into multiple lineages, are only a small subpopulation of the pool of MSCs and the remainder of the mixed population consists of cells at various stages of differentiation and commitment. Adding to the complexity of heterogeneity within a single MSC population is the variety of tissues from which MSC have been harvested and the variety of techniques that have been utilized in their isolation and propagation (Gronthos et al. (2001) J Cell Physiol 189, 54-63; Peister et al. (2004) Blood 103, 1662-8). Given these variabilities, populations and sub-populations of so-called MSCs have not yet been systematically compared.

WO 2007/123363 (Choung et al.) describes an MSC preparation that appears to be enriched for CD105+ cells and CD45− cells. However, Choung et al. does not teach an MSC preparation that is pure for CD166+ cells, CD105+ cells, and CD45− cells and does not teach a clinical scale MSC preparation containing a billion MSCs. Further, Choung et al. does not provide teachings of other technical features such as TNFRI expression, immunosuppression by inhibition of IL-2Rα expression, resilience to cryopreservation, a capacity for adipogenic, chondrogenic, and osteogenic differentiation after passage expansion.

US 2009/0010896 (Centeno et al.) describes a preparation of primary MSCs that are enriched for CD166+ cells, CD105+ cells, and CD45− cells. However, such a primary culture does not provide clinical scale MSC numbers in the billions. Further, like Choung et al., Centeno et al. lacks teaching of other technical features useful for therapeutic treatment.

Choung et al. and Centeno et al. illustrate a problem facing the skilled artisan. The art is replete with reports of poorly characterized preparations based on a mixed variety of cellular phenotypes derived from a mixed variety of manufacturing techniques. While there is a tendency among some to combine teachings from such reports, such combinations can lead to false conclusions when the reports represent different MSC populations. To advance the understanding of MSC biology and therapy, it will be important to fully characterize the phenotype of MSCs in a preparation and to recognize heterogeneity where it exists.

What is needed in the art is the ability to manufacture uniform preparations of MSCs in numbers sufficient for one or more therapeutically-effective dose, having a reproducible therapeutic action, and having a phenotype that is stable during ex vivo expansion and following cryogenic preservation. Also needed are such preparations that are isogenic, minimizing certain adverse effects associated with allogeneic transplantation.

SUMMARY OF THE INVENTION

Preparations of mesenchymal stem cells (MSCs) have now been discovered with enhanced therapeutic potential and with a structural and functional phenotype that is stable in culture. Surprisingly, MSCs in these preparations can be expanded to provide a therapeutic dose; even clinical scale preparations can now be made.

MSCs of the present preparations can be expanded ex vivo and cryopreserved and thawed, yet maintaining a stable and uniform phenotype.

The MSCs of the present invention are non-primary MSCs, having an antigen profile comprising less than about 1.25% CD45+ cells (or less than about 0.75% CD45+), at least about 95% CD105+ cells, and at least about 95% CD166+ cells.

MSCs of the present preparation have a phenotype characterized by one or more of the following properties: TNFR1 expression, inhibition of IL2Rα (e.g. in a PBMC assay), greater than 70% viability after freeze-thaw, ability to maintain phenotype following ex vivo expansion, capacity for differentiation, and isogenic (i.e., derived from a single donor).

In one embodiment, the MSC preparation has a combination of unexpected technical features, namely: a) it comprises at least about 1 billion ($1 \times 10^9$) cells; b) it has an antigen profile comprising less than about 0.75% CD45+ cells, at least about 95% CD105+ cells, and at least about 95% CD166+ cells; c) it comprises TNFRI in an amount of at least about 13 pg (e.g. about 13 pg to about 44 pg) of TNFRI per million cells; d) the MSCs have a capacity for adipogenic, chondrogenic, and osteogenic differentiation; e) the MSCs are resilient to cryopreservation, i.e. after a freeze-thaw cycle, at least about 70% of the MCSs are viable, as assessed by dye exclusion; f) when mixed with PBMCs at a ratio of about 5 PBMCs per MSC, the MSCs are capable of inhibiting IL2Rα expression by CD3/CD28-activated PBMCs cells by at least about 30%, relative to a control; g) it generally contains less than about 55 µg/mL BSA and less than about 42 µg/mL trypsin; h) it is substantially free of pathogens (e.g. endotoxin, bacteria, fungi, and viruses); and i) the MSCs have a normal karyotype. Surprisingly such an MSC preparation can comprise a cell number of at least about any of: 10 billion, 100 billion, 500 billion, or 1 trillion cells, even when expanded from a single bone marrow donation.

Preparations of the above embodiment can be obtained by screening preparations made by various culture techniques known in the art or made by screening preparations made by methods including one or more of the steps of ex vivo expansion taught herein. Surprisingly, however, the inventors have discovered a novel method that involves a series of steps that result in consistent MSC preparations of the present invention, as detailed herein, for example in Example 1 through Example 41. Accordingly, the invention also provides a collection of preparations with low variability between preparations.

The invention also provides a method of preparing, screening, or selecting preparations.

The invention also provides a method of treatment comprising administering MSCs from a preparation to a subject in need thereof.

DETAILED DESCRIPTION OF THE INVENTION

As used here, the following definitions and abbreviations apply.

"BMA" means bone marrow aspirate.

"Clinical scale" as it refers to a present MSC preparation, means a preparation that contains more than one therapeutic dose. Optionally, a clinical scale preparation is derived from a single donor. For example, a clinical scale preparation of the present invention can comprise 8,000±10% or ±20% doses of 125 million MSCs (or 100 million viable MSCs after a freeze-thaw cycle). Optionally, a clinical scale preparation of the present invention can comprise 10,000±10% or ±20% doses of 125 million MSCs (or 100 million viable MSCs after a freeze-thaw cycle).

"Freeze-thaw cycle" or "cryoprotective freeze-thaw cycle" means cryogenic freezing followed by thawing and in vitro culturing under conditions to preserve viability, especially as taught here according to the present invention.

"Therapeutic dose" is an amount of MSCs that, when administered to a subject in need thereof in a single administration (or optionally in fractional amounts within a given period), can result in a clinically relevant response. A clinically relevant response is any direct or indirect indicator of a positive therapeutic response (irrespective of the eventual outcome). Methods of determining therapeutic response are well known in the art. By way of example, a therapeutic dose is about 100 million MSCs or about 125 million MSCs. Other useful therapeutic doses include about 2 million MSCs per kg, about 8 million MSCs per kg, and about 2-8 million MSCs per kg, for example, as detailed in Example 42 through Example 45.

"Exemplary" (or "e.g.," or "by example") means a non-limiting example.

"Isogenic" means that cells of a given population are autologous to each other, i.e., derived from the same donor. The term isogenic is intended to include, for example, natural variation in genetic makeup of cells derived from the same donor.

"n±x %" means a range extending from [n−(x %·n)] to [n+(x %·n)]. Such a phrase is not intended to set forth error or precision in measurement.

"$P_n$", where "n" is an integer, refers to the number of cells that a culture has been passage. P1 is the first passage after cells are plated from the bone marrow aspirate (primary culture).

The present invention provides a preparation comprising a uniform population of MSC cells in sufficient numbers to have a clinically significant effect and being greatly enriched for a subset of MSCs with a remarkable therapeutic potential. Surprisingly, it has been discovered that such a preparation can be further expanded ex vivo to produce multiple therapeutic doses, even from a single donor.

Overview of MSC Preparations.

An MSC preparation according to the present invention is an MSC preparation that is 95% homogeneous with respect to being CD105 positive and CD166 positive and being CD45 negative. This homogeneity persists through ex vivo expansion; i.e. though multiple population doublings. An example of a useful embodiment is a preparation where the MSCs comprise less than about 1.25% CD45+ cells, at least about 95% CD105+ cells, and at least about 95% CD166+ cells, and contains at least one therapeutic dose. This homogeneity persists after cryogenic storage and thawing, where the cell also generally have a viability of about 70% or more.

MSC preparations of the instant invention express substantial levels of TNFR1, for example greater than 13 pg of TNFRI per million MSCs. This phenotype is stable throughout ex vivo expansion and cryogenic storage. Indeed, the expression of levels of TNFRI in the range of about 13 to about 179 pg (e.g. about 13 pg to about 44 pg) per million MSCs is associated with a desirous therapeutic potential which also persists through ex vivo expansion and cryopreservation.

Another feature of cells according to the present invention in high potency, as defined by the ability of the cells to inhibit IL-2Rα expression on T-cells. Typically, preparations according to the present invention can inhibit IL-2Rα expression by at least about 30%, alternatively at least about 35%, alternatively at least about 40%, alternatively at least about 45%, alternatively at least about 50%, alternatively at least about 55%, alternatively at least about 60.

Optionally, the preparations of MSCs of the present invention contain at least one therapeutic dose (e.g., at least about 100 million cells or about 125 million cells).

Unexpectedly, one embodiment of the present invention provides a clinical scale preparation providing multiple therapeutic doses (e.g., expanded from a single donor).

Optionally, the preparations of the present invention, including, for example, a clinical scale preparation, can be produced that have one or more additional unexpected profiles that especially suit the preparation for clinical use. For example, the preparations of the present invention may have a profile based on potency (e.g., TNFRI activity), resilience to cryopreservation (e.g., viability after a freeze thaw cycle), differentiation capacity (i.e., the ability to differentiate into cell types), retention of differentiation capacity, unexpected therapeutic utility as taught herein, or any combination of the aforementioned properties.

Optionally, the preparations of the present invention comprise at least 100 million cells, have an antigen profile of less than about 1.25% CD45+ cells, at least about 95% CD105+ cells, and at least about 95% CD166+ cells and the cells can be expanded ex vivo from passage 2 until passage 5 while maintaining population uniformity based upon the antigen profile (i.e. less than about 1.25% CD45+ cells, at least about 95% CD105+ cells, and at least about 95% CD166+ cells).

An MSC preparation can be in any form. In one embodiment, a preparation is provided in a single volume or aliquot (e.g., in a single container comprising the entire preparation). In another embodiment, a preparation is provided as a non-continuous preparation (e.g., the preparation is provided as a plurality of spatially separate compositions). Optionally, a non-continuous preparation is provided in a plurality of vessels, wherein each of the plurality of vessels contains a portion of the preparation. Optionally, the vessels are bags, or other useful storage containers. Optionally, the vessels are other therapeutic dosage form. Optionally, the vessels are culture vessels. Optionally, a continuous or non-continuous preparation is present in a facility, such as an MSC manufacturing facility.

Optionally, the MSCs in the preparation are isogenic (e.g., derived from the same donor).

Optionally, the majority of MSCs in the preparation have about the same ex vivo age.

Optionally, the majority of MSCs in the preparation are of about the same generation number (i.e., they are within about 1 or about 2 or about 3 or about 4 cell doublings of each other). Optionally, the average number of cell doublings in the present preparations is about 20 to about 25 doublings. Optionally, the average number of cell doublings in the present preparations is about 9 to about 13 (e.g., about 11 or about 11.2) doublings arising from the primary culture, plus about 1, about 2, about 3, or about 4 doublings per passage (for example, about 2.5 doublings per passage) as seen in the MSC preparations set forth in Example 30 and Example 32. Exemplary average cell doublings in present preparations are any of about 13.5, about 16, about 18.5, about 21, about 23.5, about 26, about 28.5, about 31, about 33.5, and about 36 when produced by about 1, about 2, about 3, about 4, about 5, about 6, about 7, about 8, about 9, and about 10 passages, respectively.

Optionally, the majority of MSCs in the preparation have about the same passage number (e.g., they are within about 1 or about 2 or about 3 or about 4 passages numbers of each other). Exemplary passage numbers in present preparations are any of about 2 to about 5, about 2 to about 6, about 2 to about 7, about 2 to about 8, about 3 to about 5, about 3 to about 6, about 3 to about 7, about 3 to about 8, about 4 to about 7, about 4 to about 8, about 4 to about 9, or less than any of about 10, about 11, or about 12.

Preparation Profiles

Surprisingly, it has been discovered that MSCs can be cultured and expanded ex vivo to produce a preparation containing at least one therapeutic dose (or optionally, multiple therapeutic doses constituting a clinical scale preparation) with an antigen profile of less than about 1.25% CD45+ cells, at least about 95% CD105+ cells, and at least about 95% CD166+ cells (e.g., as set forth in Example 30 or Example 32). Additionally, the MSC preparations having such an antigen profile can be produced that also have one or more other unexpected profiles that especially suit the preparation for clinical use For example, the preparation may exhibit unexpected potency (e.g., TNFRI concentration or activity as set forth in Example 30 or Example 32), resilience to cryopreservation (e.g., viability after a freeze thaw cycle as set forth in Example 30 or Example 32), differentiation capacity or retention and differentiation (e.g., the ability to differentiate into cell types as set forth in Example 30 or Example 32).

In some embodiments of the present technology, the preparations of MSCs have an antigen profile of at least about 95% CD166+ cells, alternatively at least about 95.5% CD166+ cells, alternatively at least about 96%, alternatively at least about 96.5%, alternatively at least about 97%, alternatively at least about 97.5%, alternatively at least about 98%, alternatively at least about 98.5%, alternatively at least about 99%, alternatively at least about 99.5% of CD166+ cells, or any amounts in between, for example, in increments of about 0.01%, about 0.025%, about 0.05%, about 0.075% about 0.1%, etc. In some embodiments, the MSCs of the present technology further include an antigen profile of at least about 95% CD105+ cells, alternatively at least about 95.5%, alternatively at least about 96%, alternatively at least about 96.5%, alternatively at least about 97%, alternatively at least about 97.5%, alternatively at least about 98%, alternatively at least about 98.5%, alternatively at least about 99%, alternatively at least about 99.5% of CD105+ cells, or any amounts in between, for example, in increments of about 0.01%, about 0.025%, about 0.05%, about 0.075%, about 0.1%, etc. In some embodiments, the MSCs of the present technology have an antigen profile of less than about 1.75% CD45+ cells, alternatively less than about 1.7%, alternatively less than about 1.65%, alternatively less than about 1.6%, alternatively less than about 1.55%, alternatively less than about 1.5%, alternatively less than about 1.45%, alternatively less than about 1.4%, alternatively less than about 1.35%, alternatively less than about 1.3%, alternatively less than about 1.25%, alternatively less than about 1.2%, alternatively less than about 1.15%, alternatively less than about 1.1%, alternatively less than about 1.05%, alternatively less than about 1%, alternatively less than about 0.95%, alternatively less than about 0.9%. alternatively less than about 0.85%, alternatively less than about 0.8%, alternatively less than about 0.75%, alternatively less than about 0.7%, alternatively less than about 0.65%, alternatively less than about 0.6%, alternatively less than about 0.55%, alternatively less than about 0.5%, alternatively less than about 0.45%, alternatively less than about 0.4%, alternatively less than about 0.35%, alternatively less than about 0.3%, alternatively less than about 0.25%, alternatively less than about 0.2%, alternatively less than about 0.15%, alternatively less than about 0.1%, alternatively less than about 0.05%, alternatively less than about 0.04%, alternatively less than about 0.03%, alternatively less than about 0.01%, or any amounts in between, for example, in increments of about 0.001%, about 0.005%, about 0.01%, about 0.025%, about 0.05%, about 0.075%, about 0.1%, etc. In some embodiments, the antigen profile of the MSCs is about 95% or greater of CD166+ cells, about 95% or greater of CD105+ cells, and 1.75% or less of CD48+ cells, preferably about 97.5% or greater of CD166+ cells, about 98% or greater of CD105+ cells, and 1.48% or less of CD48+ cells. In one embodiment, the invention provides a preparation, therapeutic dose, or a clinical scale preparation having a quantity of MSCs and an antigen profile set forth in Example 30 or Example 32. The antigen profile is a useful indicator of phenotypic purity. Methods for determining an antigen profile are provided herein.

In one embodiment, the invention provides a therapeutic dose or a clinical scale preparation having a TNFRI profile of greater than about 13 pg per million MSCs, or optionally about 13 pg to about 179 pg per million MSCs (e.g., as set forth in Example 30 or Example 32) such as about 13 pg to about 44 pg/million MSCs. Among other qualities, a TNFRI profile is a useful indicator of potency of the preparation (e.g., capacity for immunosuppression). The potency and activity in the TNFRI profiles of the present invention are based on the relative amount of TNFRI (pg per million MSCs) in the preparation (e.g., as set forth in Example 30 or Example 32). The activity of the preparation can be expressed as the percent IL-2Rα expression inhibition on mitogen-stimulated white blood cells (e.g., as set forth in Example 32). Methods for determining relative TNFRI amount or aggregate cellular preparation activity are provided herein.

In one embodiment, the invention provides a therapeutic dose or a clinical scale preparation having a favorable cryopreservation profile, i.e., favorable post-thaw viability. A cryopreservation profile of the present invention indicates the resilience of the cells to cryopreservation as the percentage of viable cells in the composition after a freeze thaw cycle. A cryopreservation profile indicates the percentage of cells that are viable after a freeze-thaw cycle compared to an unfrozen composition. Exemplary post-thaw viabilities of present preparations are at least about 70%, about 75%, about 80%, about 82%, or about 85% viable cells (e.g., as set forth in Example 30 or Example 32). Methods for determining viability after a freeze thaw cycle are provided herein.

In one embodiment, the invention provides a therapeutic dose or clinical scale preparation having a favorable differentiation profile (e.g., as set forth in Example 30 or Example 32). A differentiation profile of the present invention indicates the MSCs' capacity for each of osteogenic, chondrogenic, and adipogenic differentiation at a given passage number or doubling number. Methods for determining differentiation capacity are described herein.

In one embodiment, the invention provides a therapeutic dose or clinical scale preparation having a normal karyotype, i.e. a preparation having cells with no chromosomal abnormalities, for example, as described in Example 37. Chromosomal abnormalities that can be screened optionally include numerical and structural abnormalities, such as translocations, breaks, rings, markers and double-minutes.

In one embodiment, the invention provides a therapeutic dose or clinical scale preparation comprising MSCs with a spindle-shaped morphology or appearance (as opposed to star, flat, or round shape). Optionally, at least about any of: about 80%, about 90%, or about 95% or greater of the MSCs exhibit a spindle-shaped morphology.

In one embodiment, the invention provides a therapeutic dose or clinical scale preparation free of pathogen contaminants (e.g. fungi, viruses, mycobacteria, and other pathogenic bacteria), for example, as detailed in Example 38.

In one embodiment, the invention provides a therapeutic dose or clinical scale preparation free of abnormalities in telomerase activity. Methods of determining such are well known in the art.

In one embodiment, the invention provides a therapeutic dose or clinical scale preparation wherein the cells are non-senescent. Methods of determining senescence are well known in the art, for example as described by Wagner et al. (Wagner et al., "Replicative Senescence of Mesenchymal Stem Cells: A Continuous and Organized Process", PLoS ONE. 2008; 3(5): e2213; Wagner et al. "How to track cellular aging of mesenchymal stromal cells?," Aging (Albany NY). 2010 April; 2(4): 224-230). Optionally, non-senescent MSCs do not have elevated levels of senescent markers such as micro-RNA markers or protein markers (e.g. expression is similar to P1 MSC cultures, or within about 10%, or about 25%, or about 50%). For example, hsa-mir-371, hsa-mir-369-5P, hsa-mir-29c, hsa-mir-499 and hsa-mir-217; GPNMB; RAMP; PERP; LY96; STAT1; and PRNP have all been shown to be up-regulated in senescent MSCs (Wagner et al.). Optionally, non-senescent cells exhibit typical morphology of non-senescent cells. For example, it has been shown that senescent MSCs enlarge and generate more vacuoles and cellular debris compared to non-senescent cells (Wagner et al.). Optionally, the cells remain non-senescent for at least 1, 2, or 3 additional population doublings.

In one embodiment, the invention provides a therapeutic dose or clinical scale preparation having an antigen profile, TNFRI profile, cryopreservation profile, and differentiation profile, as described above.

In one embodiment, the invention provides a therapeutic dose or clinical scale preparation having an antigen profile, TNFRI profile, karyotype, and differentiation profile, as described above. Optionally, the therapeutic dose or clinical scale preparation further comprises a cryopreservation profile, as described above.

In one embodiment, the invention provides a pathogen-free therapeutic dose or clinical scale preparation having an antigen profile, TNFRI profile, and differentiation profile, as described above. Optionally, the therapeutic dose or clinical scale preparation further comprises a cryopreservation profile, as described above. Optionally, the therapeutic dose or clinical scale preparation further comprises a normal karyotype, as described above.

In one embodiment, the invention provides a therapeutic dose or clinical scale preparation having an antigen profile, TNFRI profile, telomerase activity, and differentiation profile, as described above. Optionally, the therapeutic dose or clinical scale preparation further comprises a cryopreservation profile, as described above.

In one embodiment, the invention provides a therapeutic dose or clinical scale preparation having an antigen profile, TNFRI profile, morphology, and differentiation profile, as described above. Optionally, the therapeutic dose or clinical scale preparation further comprises a cryopreservation profile, as described above.

In one embodiment, the invention provides a therapeutic dose or clinical scale preparation having an antigen profile, TNFRI profile, non-senescent state, and differentiation profile, as described above. Optionally, the therapeutic dose or clinical scale preparation further comprises a cryopreservation profile, as described above.

Clinical Scale Preparations

Surprisingly, a population of MSCs, e.g., derived from only a single donor, can expanded to a clinical scale preparation having an antigen profile taught herein (e.g., as detailed forth in Example 30 or Example 32).

A clinical scale preparation of the present invention provides several superior advantages. The availability of multiple, nearly identical therapeutic doses (i.e., within the variance taught here) allows more predictable clinical responses. Subjects that respond to a therapeutic dose can be subsequently treated with reduced risk of toxicity. As information is obtained for various conditions, dosing (frequency and amounts) can be adjusted to achieve better therapeutic outcomes.

Without being bound by theory, it is believed that the therapeutically effective amount of cells is highly dependent on the nature of the preparation itself, for example, the phenotypic purity, potency, resilience to cryopreservation, and/or differentiation capacity of cells in the preparation. Unless indicated otherwise, a therapeutically effective dose of MSC preparations of the present invention is about 100 million cells or about 125 million cells. While the skilled artisan can readily determine the number of the present MSCs required for a therapeutic dose, in general (depending upon the therapeutic need), such a number can be any of about 50 million, about 100 million, about 250 million, or about 500 million, or about $1 \times 10^6$ cells for example. Other useful therapeutic doses include about 2 million MSCs per kg, about 8 million MSCs per kg, and about 2 to about 8 million MSCs per kg, for example, as detailed in Example 42 through Example 45.

Surprisingly, an MSC population derived from only a single donor can be expanded to produce a clinical scale MSC preparation containing about at least any of: about 2; about 8; about 11; about 36; about 50; about 150; about 220; about 690; about 960; about 1,000; about 2,000; about 3,000; about 4,200; about 5,000; about 6,000; about 7,000; or about 8,000 therapeutic doses, wherein the preparation has the antigen profile described above (e.g., as set forth in Example 30 and Example 32).

By way of example, one embodiment of the present invention provides an MSC preparation of about $1 \times 10^{12}$ or about $1 \times 10^{12} \pm$about 10%, about 20%, about 30%, or about 40% MSCs, with the antigen profile described above. Such an MSC preparation is capable of providing, for example, about 8,000±about 10%, about 20%, about 30%, or about 40% doses to a patient before or after a freeze-thaw cycle (e.g., a patient with an immune modulatory disease such as GVHD) or, optionally about 10,000±about 10%, about 20%, about 30%, or about 40% doses to a patient before or after a freeze-thaw cycle. Such a clinical scale preparation is quite remarkable, for example, because a single patient can be frequently and repeatedly treated with doses of MSCs expanded from a single donation (e.g., bone marrow donation of 100 ml to 120 ml). For example, with the teachings provided herein, a single donation of bone marrow (e.g., 100-120 ml) can be used to produce a preparation of MSCs which can be used to treat a patient for many months or many years (i.e., lifelong treatment).

With the teachings provided herein, the skilled artisan can now make clinical scale MSC preparations having a desired number of MSCs with the antigen profiles taught herein. In general, the final number of MSCs in a preparation is dependent the starting number of primary MSCs (or volume of bone marrow aspirate) and the expansion level. However, large aspirate and culture volumes introduce a number of technical challenges. Successful culture of cells to provide clinical scale preparations of the instant invention can require a heavy burden on cell handling and sterile technique. Even the most well-established culture methods can impart culture heterogeneity in a multitude of ways. A present clinical scale preparation can optionally be obtained by serial passage expansion where each passage includes a step of splitting the previous culture into a plurality of cultures at a given ratio. Each passaging step increases the number of concurrent cultures in the preparation. By way of example, the method detailed in Example 1 through Example 25 produces over 7,000 cell factories for a single isogenic preparation. It is quite remarkable that, by following the teachings provided herein, one can successfully produce clinical scale preparations having the instant preparation profiles, e.g. antigen profile, TNFRI profile, cryopreservation profile, differentiation profile, and/or sterility (with respect to pathogens).

In one embodiment, a preparation is provided comprising at least about $1 \times 10^9$ MSCs (e.g. ≥P2 cells). In one embodiment, a preparation is provided comprising at least about $4.5 \times 10^9$ MSCs (e.g. ≥P2 cells). In one embodiment, a preparation is provided comprising at least about $31 \times 10^9$ MSCs (e.g. ≥P3 cells). In one embodiment, a preparation is provided comprising at least about $177 \times 10^9$ MSCs (e.g. ≥P4 cells). In one embodiment, a preparation is provided comprising at least about $8 \times 10^{11}$ MSCs (e.g. ≥P5 cells). In one embodiment, a preparation is provided comprising at least about $1 \times 10^{12}$ MSCs (e.g. ≥P5 cells). In one embodiment, a preparation is provided comprising about $1 \times 10^9$ to about $1 \times 10^{12}$ MSCs (e.g. P1, P2, P3, P4, or P5 cells). In one embodiment, a preparation is provided comprising about $4.5 \times 10^9$ to about $1 \times 10^{12}$ MSCs (e.g. P2, P3, P4, or P5 cells). In one embodiment, a preparation is provided comprising about $31 \times 10^9$ to about $1 \times 10^{12}$ MSCs (e.g. P3, P4, or P5 cells). In one embodiment, a preparation is provided comprising about $177 \times 10^9$ to about $1 \times 10^{12}$ MSCs (e.g. P4, or P5 cells). In addition to having the antigen profile taught herein, the preparations listed above preparations optionally have a TNFRI profile, cryopreservation profile, and/or differentiation profile taught herein. Optionally, the preparations above retain the antigen profile after one or more additional population doublings. The invention also provides a preparation comprising any of: about $1 \times 10^9$ to about $2 \times 10^{12}$ MSCs, about $4.5 \times 10^9$ to about $2 \times 10^{12}$ MSCs, about $31 \times 10^9$ to about $2 \times 10^{12}$ MSCs, and about $177 \times 10^9$ to about $2 \times 10^{12}$ MSCs, about $1 \times 10^9$ to about $3 \times 10^{12}$ MSCs, about $4.5 \times 10^9$ to about $3 \times 10^{12}$, about $1 \times 10^9$ to about $4 \times 10^{12}$ MSCs, about $4.5 \times 10^9$ to about $3 \times 10^{12}$, about $31 \times 10^9$ to about $3 \times 10^{12}$ MSCs, about $177 \times 10^9$ to about $3 \times 10^{12}$ MSCs, about $31 \times 10^9$ to about $4 \times 10^{12}$ MSCs, and about $177 \times 10^9$ to about $4 \times 10^{12}$ MSCs.

The number of cells in a preparation of the instant invention can be estimated by considering various factors such as the initial volume of bone marrow aspirate (BMA) and number of population doublings (PD).

Table 1 shows exemplary cell numbers in a clinical scale preparation based on the number of PD and the initial volume of BMA.

TABLE 1

Example Cell Numbers

| PD | MSCs-120 ml BMA | MSCs-70 ml BMA | MSCs-20 ml BMA |
| --- | --- | --- | --- |
| 30 | 3.20E+13 | 1.87E+13 | 3.11E+12 |
| 29 | 1.60E+13 | 9.33E+12 | 1.56E+12 |
| 28 | 8.00E+12 | 4.67E+12 | 7.78E+11 |
| 27 | 4.00E+12 | 2.33E+12 | 3.89E+11 |
| 26 | 2.00E+12 | 1.17E+12 | 1.94E+11 |
| 25 | 1.00E+12 | 5.83E+11 | 9.72E+10 |
| 24 | 5.00E+11 | 2.92E+11 | 4.86E+10 |
| 23 | 2.50E+11 | 1.46E+11 | 2.43E+10 |
| 22 | 1.25E+11 | 7.29E+10 | 1.22E+10 |
| 21 | 6.25E+10 | 3.65E+10 | 6.08E+09 |
| 20 | 3.13E+10 | 1.82E+10 | 3.04E+09 |
| 19 | 1.56E+10 | 9.11E+09 | 1.52E+09 |
| 18 | 7.81E+09 | 4.56E+09 | 7.60E+08 |
| 17 | 3.91E+09 | 2.28E+09 | 3.80E+08 |
| 16 | 1.95E+09 | 1.14E+09 | 1.90E+08 |
| 15 | 9.77E+08 | 5.70E+08 | 9.49E+07 |
| 14 | 4.88E+08 | 2.85E+08 | 4.75E+07 |
| 13 | 2.44E+08 | 1.42E+08 | 2.37E+07 |
| 12 | 1.22E+08 | 7.12E+07 | 1.19E+07 |
| 11 | 6.10E+07 | 3.56E+07 | 5.93E+06 |
| 10 | 3.05E+07 | 1.78E+07 | 2.97E+06 |

Collections of Preparations

In one embodiment, the invention provides a collection (sometimes simply referred to as 'a composition') of at least three preparations, wherein each preparation comprises a therapeutic dose (or multiple doses as in a clinical scale preparation) of MSCs with an antigen profile taught herein (e.g., as set forth in Example 30 or Example 32), wherein each preparation is derived from a different donor, and wherein the variance of % CD45+ cells is less than about 0.5%, optionally less than about 0.1%, optionally less than about 0.05%, alternatively optionally less than about 0.4%, optionally less than about 0.3%, or optionally about less than 0.2%, the variance of % CD105+ cells is less than about 1%, optionally less than about 0.5%; and/or the variance of % CD166+ cells is less than about 2.5%, optionally less than about 2%, optionally less than about 1% (e.g., as set forth in Example 34). Optionally, each preparation additionally comprises one or more other profiles of set forth in Example 30 or Example 32.

In one embodiment, the invention provides an MSC manufacturing facility comprising a collection of at least three preparations, wherein each preparation of the collection comprises an antigen profile taught herein (e.g., as set forth in Example 30 or Example 32), wherein each preparation is derived from a different donor, wherein the variance of % CD45+ cells is less than about 0.5%, optionally less than about 0.1%, the variance of % CD105+ cells is less than about 1%, optionally less than about 0.5%; and the variance of % CD166+ cells is less than about 2.5%, optionally less than about 2%, optionally less than about 1% (e.g., as set forth in Example 34), and wherein greater than: about 50%, about 60%, about 70%, about 80%, about 90%, or about 95% of all clinical scale MSC preparations (e.g., preparations having at least any of: about $1 \times 10^9$, about $5.5 \times 10^9$, about $31 \times 10^9$, about $177 \times 10^9$, or about $8 \times 10^{11}$ MSCs) also have the antigen profile, for example, as described in Example 30 or Example 32.

In one embodiment, the invention provides a method of making therapeutically acceptable MSCs comprising obtaining a bone marrow aspirate containing MSCs, expanding the number of MSCs to produce a preparation having at least one therapeutic dose (e.g. a clinical scale preparation), and selecting the batch for therapeutic use if the preparation has an antigen profile taught herein (e.g., as set forth in Example 30 or Example 32). Optionally, upon repeating said obtaining and expanding steps a plurality of times to produce a plurality of preparations derived from different donors, greater than: about 50%, about 60%, about 70%, about 80%, about 90%, or about 95% of the preparations have an antigen profile taught here, for example, as described in Example 30 or Example 32.

Formulation

The MSC preparations of the present invention can optionally be formulated for pharmaceutical administration. For example, any pharmaceutically acceptable diluents can be combined with a therapeutic dose (e.g., to form a therapeutic product). Optionally, the therapeutic product comprises albumin, such as human serum albumin (HSA) or bovine serum albumin (BSA). Optionally, the therapeutic product comprises an electrolyte solution, for example, to provide physiological osmolality and pH (e.g., Plasma-Lyte®A (an electrolyte solution), Baxter, Deerfield IL). Optionally, the therapeutic product comprises a cryopreservative, such as DMSO. Optionally, during formulation of albumin (e.g., with a cryopreservative, such as DMSO), the formulation is chilled before mixing with albumin, for example, to prevent possible degradation of albumin by exothermic reaction.

In one embodiment, a therapeutic product comprises albumin, an electrolyte solution, and a cryopreservative. Optionally, the therapeutic product comprises about 0.1% to about 1 5% albumin (e.g., about 1% to about 15% such as about 5%) by weight and about 5% to about 20% cryopreservative by volume (e.g., about 10%). Optionally, the therapeutic product comprising albumin is HSA (human serum albumin), the electrolyte solution comprises Plasma-Lyte®A (an electrolyte solution), and the cryopreservative comprises DMSO.

In one embodiment, a therapeutic product comprises a therapeutic dose.

In one embodiment, a therapeutic product comprises a plurality of therapeutic doses (e.g., about 8,000±about 10% or about 20% doses, or, optionally, about 10,000±about 10% or about 20% doses, and include ranges there between). In one embodiment, the therapeutic product comprises a plurality of therapeutic doses derived from the same donor.

Manufacture

Surprisingly, a bone marrow aspirate containing only a small fraction of the MSCs of the present invention can be processed to produce a preparation containing a relatively uniform and reliable population of MSCs, expanded to a sufficient quantity for a therapeutic dosage or for a clinical scale preparation. Such preparations have an antigen profile taught herein (e.g., a preparation set forth in Example 30 or Example 32), optionally having one or more profiles selected from the group consisting of potency, resilience to cryopreservation, differentiation capacity and retention of differentiation capacity, as taught herein (e.g., as set forth in Example 30 or Example 32).

Generally, a donor is selected as taught here, a biological sample is obtained, the sample is screened (e.g., by methods taught here), acceptable samples are cultured to obtain adherent cells, the adherent cells are expanded under conditions that greatly enrich for the MSCs with desired phenotype (e.g., having an antigen profile taught herein). The culture is expanded to contain a number of cells for a therapeutic dose or for a clinical scale preparation. The preparation can be cryopreserved at one or more passages during expansion.

An MSC preparation of the present invention can be prepared by obtaining a population comprising MSCs, expanding the number by passaging the population one or more times, and selecting cells with a CD105+/CD166+/CD45− phenotype to provide a therapeutic dose or a clinical scale MSC preparation having an antigen profile taught herein (e.g., a preparation set forth in Example 30 or Example 32). In one embodiment, the selection process comprises a step of culturing a population in the presence of a substrate and selecting cells that adhere to the substrate. Optionally, the selecting step does not comprise immunoselecting (e.g. antibody-based purification). Optionally, the selecting step consists essentially of culturing a population in the presence of a substrate and selecting cells that adhere to the substrate, and optionally serially repeating said culturing and selecting steps one or more times.

As set forth below, the MSC preparations of the present invention can be produced by a series of steps, including (1) obtaining living cells from a biological sample of bone marrow (e.g. a bone marrow aspirate); (2) combining the cells with growth medium on a surface suitable for adherent cells; (3) cultivating the cells in vitro to increase the cell numbers; (4) expanding the cells numbers further through "passaging" (or subculturing); (5) optional selecting preparations that have been "qualified" by structural and function features of the therapeutic MSC preparations of the present invention; (6) optionally, cryopreserving the cells; and (6) optionally thawing the cells for subsequent therapeutic administration.

Bone marrow aspirates can typically be more than about 50 ml such as about 100 ml to about 120 ml bone marrow. These cells are "seeded" in appropriate tissue culture medium containing factors that stimulate MSC growth relative to differentiation. Initial seeding concentrations can be about 40 to about one million cells per cm$^2$ of culture dish, or about 146 or about 146 plus and minus 50 or plus and minus 100 or in the range of about 50 to about 500 cells/cm$^2$ of culture dish. Primary cells are selected for adherence to an appropriate substrate surface and cultivated for one or more weeks (e.g., for about 21±3 days), removing the non-adherent matter from the substrate surface by replacing the medium with a fresh medium and allowing the adherent MSCs to culture-expand.

Optionally, these primary cells can be further passaged to non-primary cells (e.g. removed from the culture surface and expanded into additional area) by seeding at a density of about 1,000 to about one million nucleated cells/cm$^2$ of culture dish (e.g. about 5,900 cells/cm$^2$ plus and minus about 1,200), and then culturing for additional days, e.g. about 14±about 2 days. In suitable embodiments, the primary cells are grown to confluence, and in some instances are passaged to a second culture of non-primary cells by seeding the primary cells from a confluent primary cell culture in the second culture surface in an amount below confluence and growing the non-primary culture to confluence. This method can be repeated for additional passages.

This ex vivo culture expansion can optionally comprise additional passaging (e.g., about 3, about 4, or about 5 cycles). The method can comprise, for example, passaging a number of times to provide a five passage (P5) culture.

Donor Selection

In one embodiment, a population of MSCs is derived from a tissue specimen containing MSCs (e.g., bone marrow). The donor can be any donor having MCS-containing tissue. Optionally, the donor is a human. Optionally, the donor is a living human. Optionally, the donor is not a fetus. Optionally, the donor is in a post-natal stage of life.

In one embodiment, a donor is selected for tissue donation (e.g., bone marrow donation) based on predetermined selection criteria. Optionally, a donor is determined to be eligible if the donor is free from risk factors, shows no signs of infection due to relevant communicable disease agents and infectious diseases, or is deemed physically fit to undergo the bone marrow aspirate procedure as per HCT/P regulations, for example, as set forth in Example 2.

In one embodiment, a donor is a "qualified donor". A qualified donor is a donor that is selected based on the results of one or more or all assessments/tests listed in Table 2. Optionally, a qualified donor is a donor having one or more of: a minimum of one successful donation, a previous bone marrow cell count greater than about $2.0 \times 10^6$ cells/mL, a history of negative infectious disease tests, a Body Mass Index (BMI)<about 30, and an age of about 18 to about 30 years.

In one embodiment, a qualified donor is negative or non-reactive for some or all of the diseases set forth in Table 3. Optionally, the donor is screened for said diseases using the respective example assay/test set forth in Table 3.

Donor Tissue Source

In order to obtain the present preparations, it is necessary to obtain and selectively expand the MSCs from biological samples.

Bone marrow cells can be obtained from iliac crest, femora, tibiae, spine, rib or other medullary spaces. Optionally, bone marrow is obtained as soft tissue, for example, occupying the medullary cavities of long bones, some haversian canals, and spaces between trabeculae of cancellous or spongy bone. Optionally, bone marrow is obtained as either of two types: red, which is found in all bones in early life and in restricted locations in adulthood (i.e., in the spongy bone) and is concerned with the production of blood cells (i.e., hematopoiesis) and hemoglobin; and yellow, which consists largely of fat cells and connective tissue.

The collection of MSCs-containing tissue can be performed by any method known in the art.

In one embodiment, bone marrow is collected by aspiration, for example, as set forth in Example 3. Optionally, the method of collection involves the use of an anticoagulant, for example, heparin, as set forth in Example 3. Optionally, the bone marrow is collected from the iliac crest.

In one embodiment, up to about 120 ml of bone marrow is collected from a donor, for example, as set forth in Example 3. In another embodiment, at least about 60 ml or more of bone marrow is collected. Optionally, about 60 ml (±about 10%, about 20%, or about 30%) of bone marrow is collected from each side of the iliac crest. Optionally, about 80 ml to about 120 ml or about 80 ml to about 160 ml is collected. Optionally, about 20 ml to about 40 ml, about 40 ml to about 60 ml, about 60 ml to about 80 ml, about 80 ml to about 100 ml, about 100 ml to about 120 ml, or about 120 ml to about 120 ml of bone marrow is collected. Optionally, the bone marrow is collected from the iliac crest. Optionally, the bone marrow is collected from the iliac crest and a volume equal to about half the volume in the ranges taught above is collected from each side thereof.

In one embodiment, donor tissue (e.g., BMA) is placed in a container having a tubing harness or other means allowing for transfer to a processing device For example, the processing device may be in a functionally closed system of processing steps comprising filling, sampling, and transferring of solutions, as set forth in Example 4.

Isolation of an MSC-Containing Population

An MSC-containing population can be isolated from MSC-containing tissue (e.g., bone marrow) by any method known in the art.

In one embodiment, isolation of an MSC-containing population comprises a step of isolating nucleated bone marrow cells (e.g., from BMA). Methods for the isolation of nucleated bone marrow cells are known in the art. Optionally, nucleated bone marrow cells are isolated by diluting bone marrow (e.g., BMA) and separating nucleated bone marrow cells from other cells (e.g., red blood cells). Optionally, separating comprises allowing the other cells to settle and extracting a layer of nucleated bone marrow cells, for example, as set forth in Example 5.

In one embodiment, nucleated bone marrow cells (e.g., obtained as described above) are washed and/or concentrated. Any composition known for washing can be used (e.g., a physiological salt buffer such as PBS). Optionally, washing and/or concentrating comprises washing with a culture medium. The culture medium can be any medium suitable for expansion of MSCs without differentiation (e.g., DMEM; RPMI; etc. in the presence of FBS or serum-free replacement). Optionally, the culture medium comprises L-alanyl-L-glutamine and FBS, for example, as set forth in Example 5. Optionally, the culture medium comprises DMEM, L-alanyl-L-glutamine, and about 10% FBS. Optionally, the culture medium comprises DMEM with about 4 mM L-alanyl-L-glutamine+about 10% FBS.

In one embodiment, nucleated bone marrow cells are washed and/or concentrated in an automated device, for example, as set forth in Example 5.

In one embodiment, nucleated bone marrow cells are washed or concentrated (or washed and concentrated) in a device that allows for a functionally closed system of filling, sampling, or transferring of solutions, for example, as set forth in Example 5.

Establishing an MSC Culture

An MSC culture can be established from MSC-containing tissue or an MSC-containing population (e.g., isolated nucleated bone marrow cells) by any method known in the art.

In one embodiment, an MSC culture is provided by establishing an adherent culture (e.g., a primary adherent culture). Methods of establishing an adherent MCS culture are known in the art. Generally, establishing an adherent culture comprises seeding an MSC-containing population (e.g., isolated nucleated bone marrow cells or INBMCs) on a substrate, as is known in the art (e.g., a treated or untreated plastic culture vessel), and incubating the population under appropriate conditions for expansion of adherent cells. Non-adherent cells are removed by changing the culture medium with an optional washing step.

Optionally, the culture vessel comprises a cell factory (CF). Optionally, seeding an MSC-containing population comprises seeding at a target concentration, for example, as set forth above or in Example 6.

Optionally, seeding comprises providing an MSC-containing population in suspension at a target concentration in a container and transferring the suspension to a culture vessel (e.g., a ten-stack CF), for example, as set forth in Example 6.

Optionally, seeding is performed in an automated device, for example, as set forth in Example 6. Optionally, seeding is performed in a device that allows for a functionally closed system of filling, sampling, and transferring of solutions, for example, as set forth in Example 6.

Cultured MSCs are is incubated under appropriate conditions, as is known in the art (e.g., at a desired temperature, $CO_2$ concentration, and relative humidity), for example, as set forth in Example 6.

Expansion in Culture

Once a culture of MCSs has been established (e.g., by the methods described above), the culture is expanded to increase the quantity of MCSs.

The culture is expanded in any culture medium suitable for expansion of MSCs without differentiation (e.g., DMEM, RPMI, etc. in the presence of FBS or serum-free replacement). Optionally, the culture medium contains L-alanyl-L-glutamine and FBS. Optionally, the culture medium comprises DMEM, L-alanyl-L-glutamine, and about 10% FBS. Optionally, the culture medium comprises DMEM with about 4 mM L-alanyl-L-glutamine and about 10% FBS.

While growing in culture, cells consume nutrients in the culture medium. Optionally, nutrients are replenished by adding culture medium. Optionally, replenishing comprises one or more feed changes (e.g., about every 3-4 days). Optionally, a feed change comprises removing spent medium (medium with reduced nutrient levels) and then adding fresh culture medium. Optionally, non-adherent cells are removed with the spent medium (e.g., by aspiration) during the one or more feed changes, for example, as set forth in Example 7. Optionally, the cells are grown in culture for about 14±2 days (e.g., between passages). Optionally, cells are grown in culture for about 9 to about 12 days for the final expansion stage, for example, to produce a P5 culture. Optionally, MSCs are seeded at about 5,900 cells±about 5%, ±about 10%, or ±about 20% per $cm^2$ or in a range of about 1,000 to about 10,000 and/or about 37.5× $10^6$±about 5%, ±about 10%, or ±about 20% cells per about 1.5 L of culture media for expansion steps (e.g., prior to a second or later expansion after an initial passage of an MSC culture expanded from a population of INBMCs).

MSCs in culture will generally continue growing until confluence at which time contact inhibition causes cessation of cell division or growth. A passage can then be performed at or before confluence, as described below, to reseed the culture at a reduced concentration in order to continue expansion of the cells ("passage expansion"), as described above.

Passaging

The methods of manufacture of the present invention comprise at least one passaging, splitting or "subculturing".

In one embodiment, one passage comprises removing non-adherent cells, leaving adherent MSCs. Such MSCs can then be dissociated from the substrate or flask (e.g., by using a protease such as trypsin or collagenase), media can be added, optional washing (e.g., by centrifugation) may be performed, and then the MSCs can be replated or reseeded to one or more culture vessels contain a greater surface area in total, for example, as set forth in Example 9 through Example 11. Other methods of removing non-adherent cells include steps of non-enzymatic treatment (e.g., with EDTA).

The cells can then continue to expand in culture, as described above.

Optionally, cells are passaged at or near confluence (e.g., about 75% to about 95% confluence), for example, as set forth in Example 8, Example 17, Example 18, or Example 20.

In one embodiment, the MSC preparations in culture are split at a ratio of about 1:6 (by surface area). Optionally, the MCSs in culture are split at a ratio of about 1:2 or more, about 1:3 or more, about 1:4 or more, about 1:5 or more, about 1:6 or more, about 1:7 or more, about 1:8 or more, about 1:9 or more, or about 1:10 or more.

In one embodiment, the MSCs are seeded at a concentration of about $37.5 \times 10^6$±about 5%, about 10%, about 15%, or about 20% cells/ml of culture medium.

In one embodiment, the MSCs are cultured for at least about two passages. Optionally the MSCs are cultured for about two to about five, two to about six, or two to about seven passages, or more. Optionally, the MSCs are cultured for about two, about three, about four, or about five passages. Optionally, the MSCs are passaged not more than about ten or not more than about seven passages.

Cell Handling

The process of MSC isolation and ex-vivo expansion can be performed using any equipment and cell handing methods known in the art.

Various manufacturing embodiments of the present invention employ steps that require manipulation of cells, for example, steps of seeding, feeding, dissociating an adherent culture, or washing. Any step of manipulating cells has the potential to insult the cells. Although MSCs can generally withstand a certain amount of insult during preparation, cells are preferably manipulated by handling procedures and/or equipment that adequately performs the given step(s) while minimizing insult to the cells.

Steps of washing and freezing are potentially insulting to cells. Without being bound by theory, it is believed that protocols requiring extensive washing or rapid freezing of cells do not provide the quality or consistency required to manufacture a pharmaceutical composition suitable for administration to a human. Furthermore, the effects of extensive washing or rapid freezing protocols on the viability of cells and the efficacy a pharmaceutical composition comprising such cells is unknown.

In one embodiment, the mesenchymal stem cells are washed in an apparatus that includes a cell source bag, a wash solution bag, a recirculation wash bag, a spinning membrane filter having inlet and outlet ports, a filtrate bag, a mixing zone, an end product bag for the washed cells, and appropriate tubing, for example, as described in U.S. Pat. No. 6,251,295 to Johnson, which is hereby incorporated by reference. The apparatus can be a closed or semi-closed system, thereby reducing the potential for contamination. Unwashed MSCs from the cell source bag can be mixed with the wash solution in the centrifugal filtration device. The resulting suspension of mesenchymal stem cells in wash solution then is fed to the spinning membrane filter through an inlet port. A filtrate comprising wash solution is withdrawn from the spinning membrane filter through a first outlet port, and a concentrated suspension of MSCs is withdrawn from the spinning membrane filter through a second outlet port, and fed into the recirculation wash bag. The MSCs then are withdrawn from the recirculation wash bag, mixed with additional wash solution, and sent again to the spinning membrane filter.

In one embodiment, washing comprises pooling several culture vessels in a single container and washing, for example, as set forth in Example 12 and Example 28.

In one embodiment of the present technology, a therapeutic MSC preparation is provided by placing culture expanded MSCs in an appropriate cryopreservative for cryopreservation. Optionally, the cryopreservative comprises DMSO. Optionally, an MSC preparation comprises about 5% to about 20% cryopreservative. For example, in some embodiments, a therapeutic MSC preparation comprises MSCs and about 20% DMSO. In other embodiments, a therapeutic MSC preparation comprises MSCs and about 10% DMSO. In some embodiments, the DMSO is added to purified MSCs.

In one embodiment, cells are cryogenically frozen and/or stored at less than about −70° C., for example: about ≤−80° C., about ≤−80° C. to about ≤−135° C., or about ≤−135° C. In one embodiment, cells are cryogenically frozen by reducing the preparation temperature by about one degree per minute. Optionally, cells are cryogenically frozen by reducing the preparation temperature by about one degree per minute until the preparation reaches about ≤−80° C., and then the temperature of preparation is reduced to about ≤−135° C. Optionally, the rate of temperature change before reaching about −80° C. is less than the rate of temperature change from about ≤−80° C. to about ≤−135° C. Optionally, the temperature of preparation is reduced to about ≤−80° C. in a first refrigerating apparatus that provides a controlled rate of temperature change (e.g., a Cryomed) while temperature of preparation is reduced from about ≤−80° C. to about ≤−135° C. in second refrigerating apparatus that does not provide a controlled rate of temperature change, for example, a freezer set at about ≤−135° C. (e.g., a LN2 freezer), for example, as discussed in Example 29.

In one embodiment, manufacturing of MSCs preparation is performed in a closed or semi-closed system, for example, for filling, sampling, and transfer of solutions. A closed or semi-closed system can be provided by utilizing transfer means (e.g., tubes) which are sterile-welded, sterile-fused, sterile-sealed, or otherwise sterilely connected to cell-containing vessels. Exemplary steps that can use the welder and sealer include: transfer of BMA and fluids, sampling, seeding of CF, feeds, passages, harvest, formulation, fill and cryopreservation. Exemplary cell-containing vessels include those which are used in the steps described above, for example, BMA collection containers or bags, cell washing containers or bags, cell-cryopreservation vessels or bags, cell-culture vessels, and cell-sampling vessels.

Screening

In one embodiment of the present invention, an MSC preparation is screened for therapeutic use, wherein the preparation is selected for administration to a patient if the preparation has an antigen profile taught herein (e.g., as set forth in Example 30 or Example 32). Optionally, the preparation is selected for administration only if it has an acceptable potency (e.g., a TNFRI profile set forth in Example 30 or Example 32), an acceptable post-thaw viability (e.g., as set forth in Example 30 or Example 32), has an acceptable differentiation profile (e.g., as set forth in Example 30 or Example 32), has a pathogen content under an acceptable limit, and/or has an animal-derived residual content under an acceptable limit.

A number of methods are known in the art for determining an antigen profile. In one embodiment, an antigen profile is determined by flow cytometry or fluorescence activated cell sorting (FACS). Thus, as known in the art, FACS involves exposing cells to a reporter, such as a labeled antibody, which binds to and labels antigens expressed by the cell. Methods of production of antibodies and labeling thereof to form reporters are known in the art. The cells are then passed through a FACS machine, which sorts the cells from each other based on the labeling.

The potency in the TNFRI profiles of the present invention is the relative amount of TNFRI in the preparation (pg per million MSCs) and optionally, the activity of the preparation (% IL-2Rα Inhibition). The amount of cellular TNFRI in a culture of mesenchymal stem cells can be determined by methods known to those skilled in the art. Such methods include, but are not limited to, quantitative assays such as quantitative ELISA assays, for example, as described in WO 2007/087139 to Danilkovitch et al., which is hereby incorporated by reference. It is to be understood, however, that the scope of the present invention is not to be limited to any particular method for determining the amount. The TNFRI activity of the preparation is expressed as the percent IL-2Rα expression inhibition on mitogen-stimulated white blood cells and is determined by the method described by Le Blanc et al. ("Mesenchymal Stem Cells Inhibit the Expression of CD25 (Interleukin-2 Receptor) and CD38 on Phytohaemagglutinin-Activated Lymphocytes", Scandinavian Journal of Immunology, 2004, Vol 60 No 3, Pages 307-315).

Methods of determining adipogenic, chondrogenic, and osteogenic differentiation are described by Pittenger et al. ("Multilineage potential of adult human mesenchymal stem cells". Science 1999; 284:143-7). Adipogenic differentiation can be measured by detecting the formation of lipid-rich vacuoles within cells after treatment with 1-methyl-3-isobutylxanthine, dexamethasone, insulin, and indomethacin. Chondrogenic differentiation can be measured by detecting type II collagen and expression of chondrocytic markers after culturing the cells without serum and with transforming growth factor-b3. Osteogenic differentiation is measured by detecting alkaline phosphatase expression after treatment with dexamethasone, ß-glycerol phosphate, and ascorbate and in the presence of about 10% v/v FBS.

In one embodiment of the present invention, an MSC preparation is screened for therapeutic use, wherein the preparation is selected for administration to a patient if the preparation is free of pathogens. Optionally, the pathogens screened for include on or more of endotoxin, bacteria, fungi, or viruses. Optionally, the viruses include one or more of a human T-cell lymphotropic virus nucleic acid sequence, a human hepatitis virus nucleic acid sequence, a human cytomegalovirus nucleic acid sequence, a human Epstein-Barr virus nucleic acid sequence, a human herpesvirus nucleic acid sequence, a human immunodeficiency virus nucleic acid sequence, a parvovirus nucleic acid sequence, and a human papillomavirus nucleic acid sequence. Methods for screening for such pathogens are well known in the art.

In one embodiment of the present invention, an MSC preparation is screened for therapeutic use, wherein the preparation is selected for administration to a patient if the preparation has a BSA and/or trypsin content of less than a predetermined amount. Optionally, a present preparation contains less than about 55 µg/mL, about 42 µg/mL, about 25 µg/mL, about 13 µg/mL, about 10 µg/mL BSA, about 7 µg/mL, or about 15 µg/mL BSA. Optionally, a present preparation contains less than: about 42 µg/mL or about 40 µg/mL trypsin. Such exemplary methods include quantitative assays such as quantitative immuno assays, for example, as described in copending application Ser. No. 12/541,282, filed Aug. 14, 2009, which is hereby incorporated by reference.

In one embodiment of the present invention, an MSC preparation is screened for therapeutic use, wherein the preparation is selected for administration to a patient if the preparation has acceptable freeze-thaw viability (e.g., as set forth in Example 30 or Example 32). Cell viability and cell count is assessed by flow cytometry of fluorescently stained cells, based on differential staining of viable and non-viable cells due to their respective permeabilities to DNA-binding dyes in a proprietary reagent (Viacount™, Guava Technologies). The stained sample is analyzed on a Guava PCA flow cytometer and the Guava CytoSoft software package. The Guava PCA uses a 532 nm diode laser to excite the dyes, whose fluorescence is detected by photomultipliers ("PM") (PM1 detects the viability dye emission at 580 nm; PM2 detects nuclear dye emission at 675 nm), while a photodiode measures forward light scatter (FSC). The fluorescence signal is resolved, allowing quantitation of the viable and non-viable cell populations from cellular debris in the test article. The Guava's operational range of diluted cell suspension is about 10 to about 500 particles/mL.

Methods of Use

In one embodiment, the invention provides a method of treating a subject in need thereof comprising the step of administering a therapeutic dose of an MSC preparation having an antigen profile taught herein (e.g., as set forth in Example 30 and Example 32). Optionally, the preparation further comprises a second profile taught herein (e.g., as set forth in Example 30 or Example 32).

In one embodiment, the disease is an autoimmune disease or a graft-versus-host disease treated by the administration of one or more therapeutic doses. Optionally, administration of one or more therapeutic doses produces an endpoint taught herein (e.g. overall response or partial response, such as that of a single organ). Optionally, administration of one or more therapeutic doses is therapeutically effective in steroid-refractory disease (e.g., GVHD).

By way of example, autoimmune diseases which can be treated in accordance with the present invention include multiple sclerosis, Type 1 diabetes, rheumatoid arthritis, uveitis, autoimmune thyroid disease, inflammatory bowel disease (IBD), scleroderma, Graves' Disease, lupus, Crohn's disease, autoimmune lymphoproliferative disease (ALPS), demyelinating disease, autoimmune encephalomyelitis, autoimmune gastritis (AIG), and autoimmune glomerular diseases. Also, as noted hereinabove, graft-versus-host disease (GVHD) can be treated. It is to be understood, however, that the scope of the present invention is not to be limited to the treatment of the specific diseases mentioned herein.

In general, the mesenchymal stem cell therapy is based, for example, on the following sequence: harvest of MSC-containing tissue, isolate and expand MSCs, and administer the MSCs to the animal, with or without biochemical or genetic manipulation.

A therapeutic dose for an autoimmune disease or graft-versus-host disease can contain about $1\times10^5$ cells/kg to about $1\times10^7$ cells/kg. In another embodiment, a therapeutic dose is about $1\times10^6$ cells/kg to about $5\times10^6$ cells/kg. In another embodiment, a therapeutic dose is about $2\times10^6$ cells/kg to about $8\times10^6$ cells/kg. In another embodiment, a therapeutic dose is about $2\times10^6$ cells/kg or about $2\times10^6\pm$about 10%, about 20%, or about 30% cells/kg. In another embodiment, a therapeutic dose is about $8\times10^6$ cells/kg or about $8\times10^6\pm$about 10%, about 20%, or about 30% cells/kg, and include any amounts or ranges there between. Given an MSC preparation of the present invention, the amount of mesenchymal stem cells to be administered is dependent upon a variety of factors, including the age, weight, and sex of the patient, the autoimmune disease to be treated, and the extent and severity thereof.

The mesenchymal stem cells can be administered by a variety of procedures. The mesenchymal stem cells can be administered systemically, such as by intravenous, intraarterial, or intraperitoneal administration. The mesenchymal stem cells can be administered by direct injection to an organ or tissue in need thereof. The mesenchymal stem cells can be applied topically. The mesenchymal stem cells can be applied directly to a tissue in need thereof during a surgical procedure.

The mesenchymal stem cells can be, for example, autologous, allogeneic, or xenogeneic.

The mesenchymal stem cells can be administered in conjunction with an acceptable pharmaceutical carrier. For example, the mesenchymal stem cells can be administered as a cell suspension in a pharmaceutically acceptable liquid medium or gel for injection or topical application.

In accordance with another aspect of the present invention, there is provided a method of treating an inflammatory response in an animal. The method comprises administering to the animal mesenchymal stem cells in an amount effective to treat the inflammatory response in the animal.

Although the scope of this aspect of the present invention is not to be limited to any theoretical reasoning, it is believed that the mesenchymal stem cells promote T-cell maturation to regulatory T-cells (TReg), thereby controlling inflammatory responses. It is also believed that the mesenchymal stem cells inhibit T helper 1 cells (Th1 cells), thereby decreasing the expression of the Interferon-γ (IFN-γ) in certain Th1 type inflammatory reactions, such as those associated with psoriasis, for example.

In one embodiment, the inflammatory responses which can be treated are those associated with Th1-type diseases.

In one embodiment, the inflammatory responses which can be treated are those associated with hyperactivated T helper 2 cells (Th2 cells), for example, allergies and asthma.

In one embodiment, the inflammatory responses which can be treated are those associated with psoriasis.

In another embodiment, the mesenchymal stem cells can be administered to an animal such that the mesenchymal stem cells contact microglia or astrocytes in the brain to reduce inflammation. Although this embodiment is not to be limited to any theoretical reasoning, it is believed that the mesenchymal stem cells limit neurodegeneration caused by activated glial cells in diseases or disorders such as Alzheimer's Disease, Parkinson's Disease, stroke, or brain cell injuries.

In yet another embodiment, the mesenchymal stem cells can be administered to an animal such that the mesenchymal stem cells contact keratinocytes and Langerhans cells in the epidermis of the skin to reduce inflammation as can occur in psoriasis, chronic dermatitis, and contact dermatitis. Although this embodiment is not to be limited to any theoretical reasoning, it is believed that the mesenchymal stem cells can contact the keratinocytes and Langerhans cells in the epidermis, and alter the expression of T-cell receptors and cytokine secretion profiles leading to decreased expression of tumor necrosis factor-alpha (TNF-α) and increased regulatory T-cell (Treg cell) population.

In a further embodiment, the mesenchymal stem cells can be used to reduce inflammation in an articulating joint, the bone, cartilage, or cartilage and bone, as occurs in arthritis and arthritis-like conditions, including but not limited to, osteoarthritis and rheumatoid arthritis, and other arthritic diseases listed in the website www.arthritis.org/conditions/diseases as it appears on 12 Sep. 2011. Although the scope of this embodiment is not intended to be limited to any theoretical reasoning, it is believed that the mesenchymal stem cells can inhibit Interleukin-17 secretion by memory T-cells in the synovial fluid.

In another embodiment, the mesenchymal stem cells can be used to limit inflammation in the gut and liver during inflammatory bowel disease and chronic hepatitis, respectively. Although the scope of this aspect of the present invention is not intended to be limited to any theoretical reasoning, it is believed that the mesenchymal stem cells promote increased secretion of Interleukin-10 (IL-10) and the generation of regulatory T-cells (Treg cells).

In another embodiment, the mesenchymal stem cells can be used to inhibit excessive neutrophil and macrophage activation in pathological conditions such as sepsis and trauma, including burn injury, surgery, and transplants. Although the scope of this embodiment is not to be limited to any theoretical reasoning, it is believed the mesenchymal stem cells promote secretion of suppressive cytokines such as IL-10, and inhibit IL-1 RA.

In another embodiment, the mesenchymal stem cells can be used to control inflammation in immune privileged sites such as the eye, including the cornea, lens, pigment epithelium, and retina, brain, spinal cord, pregnant uterus and placenta, ovary, testes, adrenal cortex, liver, and hair follicles. Although the scope of this embodiment is not to be limited to any theoretical reasoning, it is believed that the mesenchymal stem cells promote the secretion of suppressive cytokines such as IL-10 and the generation of Treg cells.

In yet another embodiment, the mesenchymal stem cells can be used to treat tissue damage associated with end-stage renal disease (ESRD) during dialysis or glomerulonephritis. Although the scope of this embodiment is not to be limited to any theoretical reasoning, it is believed that mesenchymal stem cells can promote renal repair. Mesenchymal stem cells also are believed to express and secrete vascular endothelial growth factor, or VEGF, which stimulates new blood vessel formation, which may aid in the repair of damaged kidney tissue.

In a further embodiment, the mesenchymal stem cells can be used to control viral infections such as influenza, hepatitis C, Herpes Simplex Virus, vaccinia virus infections, and Epstein-Barr virus. Although the scope of this embodiment is not to be limited to any theoretical reasoning, it is believed that the mesenchymal stem cells promote the secretion of Interferons including Interferon-Alpha, Interferon-Beta, and Interferon-Gamma.

In yet another embodiment, the mesenchymal stem cells can be used to control parasitic infections such as *Leishmania* infections and *Helicobacter* infections. Although the scope of this embodiment is not to be limited to any theoretical reasoning, it is believed that the mesenchymal stem cells mediate responses by T helper 2 (Th2) cells, and thereby promote increased production of Immunoglobulin E (IgE) by B-cells.

In another embodiment, the mesenchymal stem cells can be administered to an animal to treat inflammation which results from a lung disease or disorder. Such lung diseases or disorders include, but are not limited to, Acute Respiratory Distress Syndrome (ARDS), Chronic Obstructive Pulmonary Disease (COPD), Idiopathic Pulmonary Fibrosis (IPF), asthma, and pulmonary hypertension.

Although the scope of this embodiment is not to be limited to any theoretical reasoning, the inflammatory response in the above-mentioned lung diseases or disorders involves the secretion of TNF-alpha and/or MCP-I. It is believed that the mesenchymal stem cells migrate to inflamed lung tissue due to increased production of one or both of TNF-alpha and MCP-I, which are chemoattractants for mesenchymal stem cells.

It is to be understood, however, that the scope of this aspect of the present invention is not to be limited to the treatment of any particular inflammatory response.

The mesenchymal stem cells can be administered to a mammal, including human and non-human primates, as hereinabove described.

The mesenchymal stem cells also can be administered systemically, as hereinabove described, for example, but not limited to, intravenously or intra-arterially. In some embodiments, the MSCs of the present technology can be administered by direct injection into the tissue, for example, but not limited to, direct injection to inflamed tissue in a subject or a joint of a subject. For example, MSCs of the present technology can be administered directly to the heart of a patient. Alternatively, in the case of osteoarthritis or rheumatoid arthritis, the mesenchymal stem cells may be administered directly to an arthritic joint.

The mesenchymal stem cells, in accordance with the present invention, can be employed in the treatment, alleviation, or prevention of any disease or disorder which can be alleviated, treated, or prevented through angiogenesis. Thus, for example, the mesenchymal stem cells can be administered to an animal to treat blocked arteries, including those in the extremities, i.e., arms, legs, hands, and feet, as well as the neck or in various organs. For example, the mesenchymal stem cells can be used to treat blocked arteries which supply the brain, thereby treating or preventing stroke. Also, the mesenchymal stem cells can be used to treat blood vessels in embryonic and postnatal corneas and can be used to provide glomerular structuring. In another embodiment, the mesenchymal stem cells can be employed in the treatment of wounds, both internal and external, as well as the treatment of dermal ulcers found in the feet, hands, legs or arms, including, but not limited to, dermal ulcers caused by diseases such as diabetes and sickle cell anemia.

Furthermore, because angiogenesis is involved in embryo implantation and placenta formation, the mesenchymal stem cells can be employed to promote embryo implantation and prevent miscarriage.

In addition, the mesenchymal stem cells can be administered to an unborn animal, including humans, to promote the development of the vasculature in the unborn animal.

In another embodiment, the mesenchymal stem cells can be administered to an animal, born or unborn, in order to promote cartilage resorption and bone formation, as well as promote correct growth plate morphogenesis.

The mesenchymal stem cells can be genetically engineered with one or more polynucleotides encoding a therapeutic agent. The polynucleotides can be delivered to the mesenchymal stem cells via an appropriate expression vehicle. Expression vehicles which can be employed to genetically engineer the mesenchymal stem cells include, but are not limited to, retroviral vectors, adenoviral vectors, and adeno-associated virus vectors.

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1 Donor Selection

The starting material for the production of the present MSCs in this example is a bone marrow aspirate ("BMA")

obtained from a human donor. The donor is selected based on the results of one or more or all assessments/tests listed in Table 2.

TABLE 2

Donor Selection

| Assessment/Test | Acceptance Criteria |
|---|---|
| Clinical Bone Marrow Donor Application | Must be Completed |
| Consent Form for the Bone Marrow Collection | Must Consent |
| Informed Consent & Agreement for HIV Testing | Must Consent |
| Health & TSE-Risk Factor Questionnaire (TSE = transmissible spongiform encephalopathy) | As accepted by Medical Director |
| Physical assessment | As accepted by Medical Director |
| ABO Rh | Results as reported |
| HLA Typing | Results as reported |

TABLE 2-continued

Donor Selection

| Assessment/Test | Acceptance Criteria |
|---|---|
| HLA Beta DR Typing | Results as reported |
| Comprehensive Metabolic Panel (CMP) | Within acceptable limits |
| Complete Blood Count (CBC) | Within acceptable limits |

The qualified donor meets all of the following selection criteria: a minimum of one successful donation, a previous bone marrow cell count greater than $2.0 \times 10^6$ cells/mL, a history of negative infectious disease tests, a Body Mass Index (BMI)<30, and an age of 18 to 30 years.

Example 2 Donor Screening

The BMA donor is screened for acceptance by testing a sample of blood against a panel of infectious diseases as shown in Table 3. The donor meets all of the acceptance criteria shown in Table 3.

TABLE 3

Donor Screening

| Disease | Assay/Test | Acceptance Criteria | Regulatory Status |
|---|---|---|---|
| Human Immunodeficiency Viruses 1 and 2 (HIV) Antibody HIV-1, HIV-2 | Genetic Systems HIV-1/HIV-2 Plus 0 EIA (Bio-Rad Laboratories, Hercules, CA) | Negative or Nonreactive | FDA Licensed for donor screening |
| HIV-1. HIV-1 NAT | Procleix HIV-1/HCV Assay (Gene-Probe, Inc, San Diego, CA) | Negative or Nonreactive | FDA Licensed for donor screening |
| Hepatitis B Virus (HBV). Hep B surface Antigen (HBsAg) | Genetic System HBsAg EIA 3.0 (Bio-Rad Laboratories, Hercules, CA) | Negative or Nonreactive | FDA Licensed for donor screening |
| Hepatitis B Virus (HBV). Antibody Hep B core (total) | Ortho HBc ELISA Test (Ortho-Clinical Diagnostics, Rochester, NY) | Negative or Nonreactive | FDA Licensed for donor screening |
| Hepatitis B Virus (HBV). HBV NAT | COBAS AmpliScreen HBV Test (Roche Molecular Systems Inc, Pleasanton, CA) | Negative or Nonreactive | FDA Licensed for donor screening |
| Hepatitis C Virus (HCV). Antibody HCV | Ortho HCV Version 3.0 ELISA Test System (Ortho-Clinical Diagnostics, Rochester, NY) | Negative or Nonreactive | FDA Licensed for donor screening |
| Hepatitis C Virus (HCV). HCV NAT | Procleix HIV-1/HCV Assay (Gen-Probe, Inc., San Diego, CA) | Negative or Nonreactive | FDA Licensed for donor screening |
| Human T Cell Lymphotropic Virus Types I & II (HTLV I1/II). Antibody HTLV-I/II | Abbott HTLV I/HTLV-II EIA (Abbott Laboratories, Abbott Park, IL) | Negative or Nonreactive | FDA Licensed for donor screening |
| Cytomegalovirus (CMV). Antibody CMV Total | Capture-CMV Immucor Gamma (Immucor, Inc., Norcroos, GA) | Negative or Nonreactive | FDA Cleared for donor screening |
| Antibody Epstein-Barr Virus (EBV) IgM | AtheNa Multi-Lyte EBV (Inverness Medical Professional Diagnostics, Princeton, NJ) | Negative or Nonreactive | Laboratory Validated |

TABLE 3-continued

Donor Screening

| Disease | Assay/Test | Acceptance Criteria | Regulatory Status |
|---|---|---|---|
| Rapid Protein Reagin (RPR, Serological test for Syphilis) | Macro-Vue RPR Card Tests (BD, Franklin Lakes, NJ) | Nonreactive or Reactive | FDA Cleared for Diagnostic Use |
| Syphilis (*Treponema pallidum*). FTA-ABS performed if RPR is reactive | MarDx FTA-ABS Test System (MarDx Diagnostics, Inc. A Trinity Biotech Company, Carlesbad, CA) | Negative or Nonreactive | FDA Cleared for donor screening |
| West Nile Virus (WNV). WNV NAT | Procleix WNV Assay (Novartis, Cambridge MA) | Negative or Nonreactive | FDA Licensed for donor screening |

Example 3 BMA Collection

Collection of the BMA takes place at an outpatient surgical center (e.g., 7 days after blood sample collection was performed.) The donor is placed in the prone position and the bone marrow aspiration needle is inserted into the posterior iliac crest. The BMA collection procedure uses two syringes each containing 5 mL of 1,000 USP units/mL heparin sodium, which acts as an anticoagulant. As a result, the BMA material contains a small concentration (10,000 U/BMA) of heparin sodium. Up to 60 ml bone marrow is aspirated from the insertion site (from each side of the iliac crest), for example from 100 ml to 120 ml bone marrow in total.

Example 4 BMA Packaging

The BMA material is packaged in a 300 mL Baxter LifeCell™ tissue culture bag, which is an FDA-cleared, sterile, gas-permeable bag that is intended for the cultivation of cells grown in suspension. The container has a tubing harness allowing for functionally closed system filling, sampling, and transferring of solutions during the manufacturing process.

Example 5 Isolation of Nucleated Bone Marrow Cells from BMA

The first step (day 1) in the isolation and expansion of human mesenchymal stem cells (hMSCs) involves the isolation of nucleated bone marrow cells from the BMA. A CytoMate® Cell Washer (Baxter Healthcare Corp., Deerfield, IL) connected with a fluid transfer set is used to transfer a Plasma-Lyte®A (an electrolyte solution) (Baxter, Deerfield, IL) and Hespan formulation to the BMA by using a Terumo sterile tube welder to fuse the BMA bag tubing lines together with the fluid transfer set. In some embodiments of the present application, other cell washing or purification machines or techniques are used instead of a Cytomate Cell Washer; when the Cytomate is referred to herein, the present inventors appreciate that any suitable replacement device for cell washing or purification machines or techniques may be employed instead. Hespan is utilized to agglutinate, sediment, and separate the majority of the red blood cells (RBCs) from the bone marrow nucleated cells. Using the "Fluid Transfer" program on the CytoMate® (Baxter, Deerfield, IL), the Plasma-Lyte®A (an electrolyte solution) (Baxter, Deerfield, IL) and Hespan formulation (6% Hetastarch) is then transferred into the BMA bag and the RBCs are allowed to settle for approximately 60 to 90 minutes until a distinct separation appears between the nucleated bone marrow cells and the RBCs. The nucleated bone marrow cells (top layer) are isolated from the BMA bag using a Fenwal plasma extractor to press the upper nucleated bone marrow cell layer into a transfer pack. The isolated nucleated bone marrow cells (INBMCs) are then transferred to the CytoMate® and processed by concentrating and washing the cells with culture medium (DMEM w/ 4 mM L-alanyl-L-glutamine+10% FBS). INBMCs are counted using a Hematology Analyzer (Beckman Coulter).

Example 6 Isolation of MSCs

Following the cell count, the INBMCs are diluted to the target seeding concentration (e.g., $925 \times 10^6$ INBMCs per 55 ml) and transferred to a 1.5 L culture medium bag using the "Transfer Volume" program on the CytoMate® to obtain the "Media Cell Suspension". The "Media Cell Suspension" is used to seed the INBMCs into a $CO_2$ primed Nunc ten-stack cell factory (CF) at about 5,900 cells±about 20% per $cm^2$ of growing surface. The CF is then placed in an incubator set at about 37±1° C. and about 5±2% $CO_2$, and ambient relative humidity. This is the primary culture (P0). After the initial seeding of the INBMCs, MSCs attach to the tissue culture plastic and grow to form a primary adherent population.

Example 7 Feeds

Non-adherent cells are aspirated away during a feed change. The feed is an addition of 1.5 L of fresh culture medium to replace the existing culture medium ("spent medium") that has been depleted of nutrients from cells growing in culture. A feed is performed every 3-4 days. During each feed, the CF is examined for integrity and appearance.

Example 8 First Passage

After approximately about 21±3 days in culture, the primary culture (P0) is expanded (e.g., from one CF to approximately six CFs, or, optionally from one CF to approximately eight CFs) for the first passage (P1).

Example 9 Trypsinizing

The spent medium in each CF is drained via gravity flow into an empty medium bag that is attached (e.g., sterile welded such as using a Terumo Sterile Tubing Welder) to a CF tubing set. After the CF has been completely drained, the "spent medium" bag is removed.

A "Stop Solution" bag and a "Trypsin-EDTA (0.05% Trypsin, 0.53 mM EDTA)" bag are attached (e.g., sterile welded) to the CF tubing set. Trypsin-EDTA (approximately 400 mL) is added to the CF via gravity flow. Once the "Trypsin-EDTA" bag has been emptied, the CF is placed into a 37±1° C. and 5±2% $CO_2$ incubator for trypsinization.

Each CF is trypsinized for up to 30 minutes (e.g., up to about 15 to about 30 min or any range in-between). During the trypsinization period, the CFs are observed approximately every 8 minutes using an inverted microscope to determine the percentage of cells that have detached. When the percentage of detached cells is estimated to be >about 90%, the trypsinization is stopped by adding 100 mL of media "stop solution" (e.g., DMEM containing 10% FBS) into the CF via gravity flow. The duration of the trypsinization is recorded.

Example 10 Washing

The trypsinized-stopped cell suspension is drained via gravity flow into a 600 mL transfer pack that is attached to a CF tubing set.

The trypsinized-stopped cell suspension is then washed using the CytoMate®.

Example 11 Seeding

The hMSCs are counted on a Guava Personal Cytometer™ (Guava Technologies).

An amount of cells (e.g., about $37.5 \times 10^6$ cells or about $37.5 \times 10^6$±about 5%, about 10%, or about 20% cells) are added to 1.5 L culture medium bags on the CytoMate®. The culture medium bags now containing cells are then used to seed a corresponding number of CFs via sterile tubing connections (e.g. at about 5,900 cells/per $cm^2$±about 5%, about 10%, about 15%, or about 20% per $cm^2$). The seeded CFs are then placed in an incubator set at about 37±1° C. and about 5±2% $CO_2$, and ambient relative humidity for approximately 14±2 days, with feeds approximately every 3-4 days, as set forth in Example 7.

Example 12 Second Passage

After approximately 14±2 days in culture, the CF (e.g., six-CF, or eight-CF) P1 cultures are expanded (e.g., into 36 CFs) for the second passage (P2).

Each of the CEs (e.g., 6 CEs, or eight-CF) is passaged as set forth in Example 9 through Example 11 (e.g., to provide 36 CEs). The trypsinized-stopped cell suspensions of several CFs can be pooled before washing.

Example 13 Harvest

After approximately 14±2 days in culture, the cultured hMSCs are harvested (e.g., after about 42 to about 56 days total over two passages). Each CF is processed as set forth in Example 9 through Example 10, using Plasma-Lyte®A (an electrolyte solution) containing about 1% Human Serum Albumin as a stop solution. The trypsinized-stopped cell suspensions of several CFs can be pooled before washing.

Example 14 Preparing an In-Process Intermediate

Based on the cell yield calculated from the harvest, the pooled "Washed hMSCs", are concentrated or diluted to obtain an in-process intermediate formulation containing about 6.0 million cells/mL, for example, in a wash solution such as about 1% HSA in Plasma-Lyte®A (an electrolyte solution). The in-process intermediate is a clinical scale MSC preparation that provides a standardized formulation for sample analysis or cryopreservation before further expansion, if desired, or before administration to a patient as therapy.

Samples for sterility, endotoxin, adventitious viruses (DNA PCR and RNA PCR detection), and phenotype lot release testing are obtained from the formulation.

The in-process intermediate is diluted with an equal volume (1:1) of cryoprotectant solution containing about 20% DMSO and about 9% HSA in Plasma-Lyte®A (an electrolyte solution). The in-process intermediate has now been diluted to about 3.0 million cells/mL in approximately 10% DMSO and approximately 5% HSA in Plasma-Lyte®A (an electrolyte solution).

Samples for potency, cell line species identity, human karyotyping, and ultrastructural evaluation of cell culture for viral particles (transmission electron microscopy or "TEM") for lot release testing are then obtained from the in-process intermediate.

Example 15 Cryopreservation and Storage

A number of Cryocyte™ (Baxter, Deerfield, IL) bags (between about 100 to about 300, e.g. about 200) are filled, each with a 15 mL volume of the in-process intermediate. Each bag now contains about 45 million MSCs in about 5% HSA, about 1 0% DMSO in Plasma-Lyte®A (an electrolyte solution) (Baxter, Deerfield, IL). The in-process intermediate is then placed into a secondary packaging container (e.g. a Custom Biogenic Systems aluminum canister/cassette) that is designed to enclose and protect the Cryocyte™ bag. Once in the cassette, the in-process intermediate is cryopreserved in a Cryomed controlled-rate freezer. Following completion of the freezing program, the frozen bags are then transferred from the Cryomed® (Thermo Scientific, Rockford, IL) and placed into a LN2 cryofreezer.

Before freezing, a sample is obtained for sterility, endotoxin, appearance, and cell viability (past-thaw) testing. The in-process intermediate is screened for acceptance by each of the tests listed in Table 4.

TABLE 4

| Preparation Screen | | |
|---|---|---|
| DS Test Name | DS Sample Point | DS Specification |
| Sterility (2X DCB Formulation) | 2X DCB Formulation-Harvest | Negative |
| Mycoplasma PTC | 2X DCB Formulation-Harvest | Negative |
| Phenotype (FACS) CD166 | 1X DCB Formulation-Harvest | ≥95% CD166 |

TABLE 4-continued

Preparation Screen

| DS Test Name | DS Sample Point | DS Specification |
| --- | --- | --- |
| Phenotype (FACS) CD105 | 1X DCB Formulation-Harvest | ≥95% CD105 |
| Phenotype (FACS) CD45 | 1X DCB Formulation-Harvest | ≤1.25% CD45 |
| Detection of HCV RNA by RT-qPCR | 2X DCB Formulation-Harvest | Negative |
| Detection of CMV DNA by qPCR | 2X DCB Formulation-Harvest | Negative |
| Detection of EBV DNA by qPCR | 2X DCB Formulation-Harvest | Negative |
| Detection of HBV DNA by qPCR | 2X DCB Formulation-Harvest | Negative |
| Detection of HHV-6 Variant A and Variant B DNA by qPCR | 2X DCB Formulation-Harvest | Negative |
| Detection of HHV-8 DNA by qPCR | 2X DCB Formulation-Harvest | Negative |
| Detection of HIV-1 DNA by qPCR | 2X DCB Formulation-Harvest | Negative |
| Detection of HIV-2 DNA by qPCR | 2X DCB Formulation-Harvest | Negative |
| Detection of HTLV I & II DNA by qPCR | 2X DCB Formulation-Harvest | Negative |
| Detection of Parvovirus B-19 DNA by qPCR | 2X DCB Formulation-Harvest | Negative |
| Detection of HPV 18 DNA by qPCR | 2X DCB Formulation-Harvest | Negative |
| In-Vivo Assay for Viral Contaminants (USFDA): Mouse and Egg | 2X DCB Formulation + Spent Medium-Harvest | Negative |
| In-Vitro Assay for Detection of Adventitious Viral Contaminants: MRC-5, VERO, Hs68 Cells | 2X DCB Formulation + Spent Medium-Harvest | Negative |
| Thin Section Electron Microscopy for Detection of Viral Particles | 2X DCB Formulation + Cryoprotectant-Harvest | Negative |
| Cell Line Species Identity by Isoenzyme Electrophoresis | 2X DCB Formulation + Cryoprotectant-Harvest | Human Cell Line |
| Karyology-Cell Culture | 2X DCB Formulation + Cryoprotectant-Harvest | No Chromosomal Abnormalities |
| Sterility (Packaged Dose) | DS Packaged Donor Cell Bank | Negative |
| Endotoxin (Packaged Dose) | DS Packaged Donor Cell Bank | ≤1.67 EU/mL |
| Potency (TNF RI) | 1X DCB Formulation-Harvest | ≥39 pg/mL (13 pg/million cells) |
| Potency (IL-2Rα) | 1X DCB Formulation-Harvest | ≥30% Inhibition of IL-2Rα Expression |
| Appearance | DS Packaged Donor Cell Bank | Pass: Opaque contents, off-white to pale amber in color |

Example 16 Thawing at the In-Process Intermediate

The in-process intermediate is selected for further culture expansion. Each of the bags is thawed and processed, alone or simultaneously with the others, and processed by the steps that follow. The bag is diluted with DMEM containing about 10% FBS. A sample is taken from the bag for a cell count and cell viability assessment, and then hMSCs are transferred from the bag into 1.5 L of culture medium.

Example 17 Third Passage

The Culture Media containing hMSCs are seeded into a CF. The CF is then placed in an about 37±1° C. and about 5±2% $CO_2$ incubator and maintained with media feeds, as set forth in Example 7, for approximately 14±2 days.

Example 18 Fourth Passage

After approximately 14 days±2, the P3 culture is split (e.g., into approximately six CFs, or optionally approximately eight CFs) for the fourth passage (P4).

Example 19 Passaging

Each of the CFs (e.g., six CFs) is passaged as set forth in Example 9 through Example 11. The trypsinized-stopped cell suspensions of several CFs can be pooled before washing.

Example 20 Fifth Passage

After approximately 14±2 days (Day 28) in culture, the P4 cultures (e.g., six cultures) are split (e.g., into 40 CFs) for the fifth passage (P5).

Example 21 Passaging

Each of the CFs is passaged as set forth in Example 9 through Example 11, except that the CFs are cultured for 9 to 12 days. The trypsinized-stopped cell suspensions of several CFs can be pooled before washing.

Example 22 Pre-Harvest

After approximately 9 to approximately 12 days in culture (Day 42), the cultured hMSCs are harvested.

Example 23 Harvesting

A harvest is performed, as set forth in Example 13, except that the harvest is performed after 9 to 12 days, as detailed above.

Example 24 Formulating an MSC Preparation for Therapy or Storage

Based on the cell yield calculated from the harvest, the pooled "Washed hMSCs" are either concentrated or diluted to obtain a formulation containing about 16.6 million cells/mL. If the pooled "Washed hMSCs" are concentrated, the cells are spun down and the excess volume is removed. If the pooled "Washed hMSCs" are diluted, the required volume of Wash/Stop Solution (about 1% HSA in Plasma-Lyte®A (an electrolyte solution)) is added to get the desired concentration. A sample for phenotype and residuals (BSA and trypsin) testing are obtained from the formulation.

The formulation is then diluted with an equal volume (1:1) of cryoprotectant solution containing about 20% DMSO and about 9/o HSA in Plasma-Lyte®A (an electrolyte solution). The formulation now contains a concentration of about 8.3 million cells/mL (in approximately 1 0% DMSO and approximately 5% HSA in Plasma-Lyte®A (an electrolyte solution)).

A sample for potency testing is obtained from the diluted formulation.

Example 25 Cryopreserving and Storage

The MSC preparation is then filled into a number of Cryocyte™ bags to a volume of about 15 mL/bag (e.g., about 8,000 bags in total, or optionally about 10,000 bags in total). Each bag of the MSC preparation has a final formulation of about 125×1 06 hMSCs (at least about 100×106 viable hMSCs after a freeze-thaw cycle) in Plasma-Lyte®A (an electrolyte solution) containing a concentration of about 5% HSA and about 1 0% DMSO per bag. Bags of the MSC preparation are then placed into a secondary container (a Custom Biogenic Systems aluminum canister/cassette) that is designed to enclose and protect the Cryocyte™ bag. Once in the cassette, the MSC preparation is cryopreserved in a controlled rate freezer (Cryomed®, Thermal Scientific, Rockford, IL). Following completion of the freezing program, the frozen bags are then transferred from the Cryomed® (Thermal Scientific, Rockford, IL) and placed into LN2 cryofreezers. A sample bag is obtained for sterility, endotoxin, appearance and cell viability (post-thaw) lot release testing.

Example 26 MSC Preparation Acceptance for Therapy

The MSC preparation remains in "quarantine" pending testing and release. The MSC preparation passes each of the tests listed in Table 5.

TABLE 5

Preparation Screen

| Test Name | Sample Point | Description | Specification |
|---|---|---|---|
| Sterility (Pooled Suspension) | Pooled Suspension Bulk-Harvest | Direct Inoculation Method | Negative |
| Mycoplasma (PTC) | Pooled Suspension Bulk-Harvest | Points to Consider | Negative |
| Phenotype (FACS) CD166 | DP Formulation-Harvest | Flow Cytometry | ≥95% CD166 |
| Phenotype (FACS) CD105 | DP Formulation-Harvest | Flow Cytometry | ≥95% CD105 |
| Phenotype (FACS) CD45 | DP Formulation-Harvest | Flow Cytometry | ≤0.75% CD45 |
| Sterility (Packaged Dose) | DP | Direct Inoculation Method | Negative |
| Endotoxin (Packaged Dose) | DP | Chromogenic Kinetic Method | ≤1.67 EU/mL |
| Viability (Post Thaw) | DP | Flow Cytometry | ≥70% |
| Residual BSA | 2X DP Formulation | ELISA | ≤10 µg/mL |
| Residual Trypsin | 2X DP Formulation | ELISA | ≤30 µg/mL |
| Potency (TNF RI) | DP Formulation-Harvest | ELISA | Min: ≥108 pg/mL (13 pg/million cells) Max: ≤368 pg/mL (44 pg/million cells) |
| Potency (IL-2Rα) | DP Formulation-Harvest | ELISA | ≥30% Inhibition of IL-2Rα expression |
| Appearance | DP | Macroscopic Assessment | Pass: Opaque contents, off-white to pale amber in color, no particulates/fibers, no |

TABLE 5-continued

| | Preparation Screen | | |
|---|---|---|---|
| Test Name | Sample Point | Description | Specification |
| | | | cell clumping observed, package integrity must be intact. |

Example 27 Evaluation of Passage Number

The number of cells harvested per donor is correlated with the number of passages during culture expansion. Although cells from any passage can be formulated for therapy, it has been surprisingly discovered that limiting the number of passages, for example, to less than any of about 14, about 10, about 8, or about 6 passages, provides preparations with a superior safety profile. By the end of the process set forth in Example 1 through Example 23, there are approximately 22 to approximately 25 (e.g., 25) population doublings. Without being bound by theory, it is believed that limiting the number of passages minimizes the risk of spontaneous genetic transformations.

Example 28 Evaluation of Washing Protocol

Based on low post-thaw cell viabilities observed in a development study, changes were made in the CytoMate® (Baxter, Deerfield, IL) cell washing process to improve cell viability and cell recovery post-thaw. The old standard procedure to be improved upon here used a CytoMate® (Baxter, Deerfield, IL) programmed to wash all three collection bags serially. The time required to complete the entire wash cycle was three times longer than the time required to wash the contents of one individual collection bag. Surprisingly, it was discovered here that standard shear forces experienced by the cells during washing reduced cell viability and resilience to cryopreservation.

In the new procedure, the contents of the cell factories harvested at each passage are transferred into collection bags for cell washing. An automated cell washer (CytoMate® (Baxter, Deerfield, IL)) is used during processing to provide consistent, automated cell washing. The change in the washing process was to wash one collection bag at a time, and after completion of its wash cycle, transfer the contents of the washed cells to a "Washed hMSC" collection (or holding) bag. Without being bound by theory, it is believed that this modification to the process reduced the cell wash exposure time per collection bag by one third, thus protecting the cells from unnecessary handling and exposure to the shear forces of cell washing.

Example 29 Evaluation of Freezing Protocol

Based on low post-thaw cell viabilities observed in a development study, changes in the Cryomed® (Thermo Scientific, Rockford, IL) freezing process were made to ensure good cell viability and cell recovery post-thaw. Surprisingly, standard procedures previously used for freezing MSC preparations resulted in unacceptable cell viability. Changes in the Cryomed® (Thermo Scientific, Rockford, IL) freezing process included a modification to the freeze program so that it would closely mimic what is experienced by cells which are simply placed in an −80° C. freezer inside an insulated container. These modifications raised cell viability post-thaw by approximately 20%.

In manufacturing, a Cryomed® (Thermo Scientific, Rockford, IL) freezer is used at the time of harvest to provide controlled-rate freezing of the cells to ≤−80° C. prior to the transfer to a $LN_2$ freezer (≤−135° C.). In development and research, small scale samples were initially frozen directly in a −80° C. inside an insulated container, and then transferred to a $LN_2$ freezer (≤135° C.). It was noted that these samples had consistently high viability. A study was conducted to map the temperature profile under these conditions. This temperature profile was then programmed into the Cryomed® (Thermo Scientific, Rockford, IL) freezer and tested. The effect was a more gradual temperature transition to the final freezing temperature. This change was found to improve cell viability and was incorporated into the current Cryomed® (Thermo Scientific, Rockford, IL) freezing process used in manufacturing.

Example 30 Production of Clinical Scale MSC Preparations Through Passage 2

Multiple clinical scale preparations were produced, each by the method set forth in Example 1 through Example 15 to produce a collection of preparations. Each MSC preparation contained about $4.5 \times 10^9$ to about $6.3 \times 10^9$ cells (about 30 to about 50 doses), for example about $5.5 \times 10^9$ cells derived from a single donor with an average of 5 population doublings compared to the P0 culture. After thawing, a sample from each preparation was tested for antigen profile, TNFRI profile, cell viability, and capacity for differentiation.

As shown in Table 6, each preparation in the collection had an antigen profile of less than about 1.25% CD45+ cells, at least about 95% CD105+ cells, and at least about 95% CD166+ cells. Also as shown in Table 6, each preparation in the collection had a TNFRI profile of at least about 13 pg TNFRI per million cells. Each preparation had a cell viability of at least about 70% (data not shown). Cells from each preparation were tested and determined to have a capacity for chondrogenesis, osteogenesis, and adipogenesis.

The antigen profile of MSCs was assessed by fluorescence-activated cell sorting (FACS) analysis. The assay used a single-antibody approach and generated data reflecting expression of the three markers individually (CD45−, CD105+, and CD166+). CD45 (LCA) is a marker for cells of hematopoietic origin, while CD105 (endoglin) and CD166 (ALCAM) are markers for MSCs. The MSC samples were labeled with commercial fluorescent antibodies to the cell surface markers, then washed, fixed and subjected to flow cytometric analysis. An isotype antibody negative control was also run at the same time. The MSC phenotype profile was determined using CELLQuest software (Becton, Dickinson and Company, San Jose CA). The cells were first identified on the basis of light scatter properties (forward scatter for size and side scatter for internal granularity), while marker expression was assessed through fluorescence from the bound antibodies. In the forward scatter versus side scatter dot blot for the unstained control, the main dot cluster was positioned at the center of the side scatter axis by adjusting the side scatter voltage control. The acquisition gate, defined by the R1 region, was subsequently adjusted to ensure that the main dot cluster is completely enclosed within the R1 region. The data acquisition process involved the accumulation of 10,000 events. When the analysis of the unstained control was complete, the isotype antibody negative control was analyzed using the acquisition parameters that were defined for the unstained control. The CD166, CD105, and CD45 test samples were analyzed using the same approach. The fluorescence threshold for positive marker expression was defined using the isotype antibody negative control, which was adjusted so that at least about 99.50% of the negative control cells were identified as "negative". This threshold was used to measure the percentage of positive cells for each of the three cell surface markers independently.

Cell viability was assessed by a flow cytometry of fluorescently stained cells, based on differential staining of viable and non-viable cells on their respective permeabilities to DNA-binding dyes in a proprietary reagent (Viacount™, Guava Technologies, Millipore, Billerica, CA). The stained sample was analyzed on a Guava PCA flow cytometer and the Guava CytoSoft software package (Millipore, Billerica, CA). The Guava PCA uses a 532 nm diode laser to excite the dyes, whose fluorescence is detected by photomultipliers (PM: PM1 detects the viability dye emission at 580 nm; PM2 detects nuclear dye emission at 675 nm), while a photodiode measures forward light scatter (FSC). The fluorescence signal was resolved, allowing quantitation of the viable and non-viable cell populations from cellular debris in the test article.

To test for osteogenic differentiation, about $3\times10^4$ hMSCs were seeded onto 35 mm dishes in medium (DMEM, 10% FBS). After 24 hours, the medium was replaced with osteogenic assay medium (DMEM, 10% FBS, 50 mM ascorbate 2-phosphate, 10 mM β-glycerol phosphate, 0.1 mM dexamethasone), which was replaced every three to four days during the 17-day period of the assay. At the end of culture period MSC osteogenic differentiation was assessed using von Kossa staining and by measurement of calcium accumulation in cells. Selected specimens were subsequently stained for mineral by the von Kossa method. Cell layers were fixed with 10% formalin for 1 hour, incubated with 2% (w/v) silver nitrate solution for 10 minutes in the dark, washed thoroughly with deionized water and then exposed to bright light for 15 minutes. For the calcium assay, cell layers were rinsed twice with Phosphate Buffered Saline (PBS) and scraped off the dish in 0.5N Hydrochloric acid. Calcium was then extracted from the cell layers by shaking for 4 hours at 4° C. followed by centrifugation at 1,000×g for 5 minutes. The calcium content of the resulting supernatant was determined according to the manufacturer's instructions for Sigma kit #587-A. Absorbance of samples was measured at 575 nm using a Beckman spectrophotometer. Total calcium in samples was calculated using standards assayed in parallel and expressed as μg per dish.

To test for chondrogenic differentiation, chondrogenic differentiation was induced by gently pelleting about $2.5\times 10^5$ hMSCs in defined chondrogenic medium (high-glucose DMEM, ITS$^+$ supplement (Becton-Dickinson), 0.1 mM dexamethasone, 10 ng/mL TGF-β3, 50 μg/mL ascorbate 2-phosphate, 2 mM pyruvate+antibiotics) in a 15 mL conical tube. The pellet culture was then incubated at 37° C. for 1 to 4 weeks with medium replacement every 2 to 3 days. At harvest, the pellets were gently fixed in 4% formaldehyde, embedded in paraffin, and then sections cut and analyzed. Type II collagen was detected by immunohistochemical methods. Sections were also stained for proteoglycans using Toluidine Blue and Safronin O.

To test for adipogenic differentiation, adipogenic differentiation was induced by adding adipogenic induction medium (DMEM, 10% FBS, 1 mM dexamethasone, 0.5 mM methyl-isobutylxanthine, 0.2 mM indomethecin, 10 μg/mL insulin and antibiotics) to hMSCs previously grown for several days after reaching confluency. After induction, the media was changed to adipogenic maintenance media (DMEM, 10% FBS, 10 μg/mL insulin and antibiotics) and the culture grown for a further 1 week. Lipid vacuoles in cells differentiated into adipocytes were detected by Oil Red O.

For the TNFRI assay, MSC samples were processed to lyse the cells and release TNFRI into solution. An ELISA method was used to quantify TNFRI using a commercially available kit. This kit allowed for the measurement of both cell-associated TNFRI, and soluble TNFRI that has been shed from cell surface. The assay employed a quantitative sandwich enzyme immunoassay technique. Samples were added to a microplate that had been precoated with a monoclonal antibody specific for human TNFRI. TNFRI present in standards and samples was captured by the immobilized anti-TNFRI antibody. After repeated washing to remove unbound extraneous material, an enzyme-linked polyclonal antibody specific for TNFRI was added. Following incubation, a wash was done to remove unbound antibody-enzyme reagent, and then a substrate solution was added and color develops in proportion to the amount of TNFRI bound to the microplate. The color development was stopped at a specified time point and the intensity of the color is measured using a microplate spectrophotometer. Quantitation was achieved by comparing the signal of unknowns to TNF RI standards assayed at the same time. Although quantification using this assay provides units of pg TNFRI/ml, the amount of TNFRI relative to the number of MSCs ('potency') can be obtained by calculating the concentration of MSCs before lysis.

TABLE 6

Clinical scale MSC preparations produced through passage 2

| Test | Sampling | Test Method | Expected Results | Lot 1 | Lot 2 | Lot 3 |
|---|---|---|---|---|---|---|
| Phenotype | Date of Manufacture 2X DCB Formulation | FACS G-SOP-Q0007 | ≥95% CD105 ≥95% CD166 ≤1.25% CD45 | 25 Aug. 2005 99.22% CD105 99.23% CD166 0.27% CD45 | 26 Aug. 2005 99.28% CD105 99.35% CD166 0.00% CD45 | 8 Sep. 2005 99.42% CD105 99.39% CD166 0.02% CD45 |
| TNF RI | DCB Formulation | Sandwich ELISA | ≥108 pg/mL$^1$ | 430 pg/mL | 579 pg/mL | 453 pg/mL |

TABLE 6-continued

Clinical scale MSC preparations produced through passage 2

| | | | | | | |
|---|---|---|---|---|---|---|
| Cell Line Species Identity | DCB Formulation | Isoenzyme electrophoresis | human cell line | human cell line | human cell line | human cell line |
| Karyology | DCB Formulation | cytogenic evaluation | no chromosomal abnormalities | no chromosomal abnormalities | no chromosomal abnormalities | no chromosomal abnormalities |
| Sterility | 2X DCB Formulation packaged DCB (post thaw) | USP <71> Direct Method | Negative | Negative | Negative | Negative |
| Mycoplasma | pooled suspension | 1993 FDA PTC (Indirect and Direct method) | Negative | Negative | Negative | Negative |
| Endotoxin | 2X DCB Formulation packaged DCB (post thaw) | USP <85> (LAL; kinetic chromogenic) | ≤1.67 EU/mL | pass | pass | pass |
| Ultrastructural Evaluation of Cell Cultures for Viral Particles | DCB Formulation | Thin-Section TEM | Negative | Negative | Negative | Negative |
| in Vitro Assay for Detection of Adventitious Virus Contaminants | pooled suspension | MRC-5, VERO, and Hs68 cells | Negative | Negative | Negative | Negative |
| In Vitro Assay for Detection Adventitious Virus Contaminates | pooled suspension | USFDA | Negative | Negative | Negative | Negative |
| Detection of HTLV I & II | 2X DCB Formulation | DNA qPCR | Negative | Negative | Negative | Negative |
| Detection of Human HBV | 2X DCB Formulation | DNA qPCR | Negative | Negative | Negative | Negative |
| Detection of Human CMV | 2X DCB Formulation | DNA qPCR | Negative | Negative | Negative | Negative |
| Detection of Human EBV | 2X DCB Formulation | DNA qPCR | Negative | Negative | Negative | Negative |
| Detection of HHV-6A and HHV-6B | 2X DCB Formulation | DNA qPCR | Negative | Negative | Negative | Negative |
| Detection of HIV-1 | 2X DCB Formulation | DNA qPCR | Negative | Negative | Negative | Negative |
| Detection of HIV-2 | 2X DCB Formulation | DNA qPCR | Negative | Negative | Negative | Negative |
| Detection Parvovirus B-19 | 2X DCB Formulation | qRT-PCR | Negative | Negative | Negative | Negative |
| Detection of HCV | 2X DCB Formulation | DNA qPCR | Negative | Negative | Negative | Negative |
| Detection of Human Papilloma Virus (HPV) | DCB Formulation | DNA qPCR | Negative | Negative | Negative | Negative |
| Detection of HHV-8 | 2X DCB Formulation | DNA qPCR | Negative | Negative | Negative | Negative |

| Test | Sampling | Test Method | Expected Results | Lot 4 | Lot 5 | Lot 6 |
|---|---|---|---|---|---|---|
| Date of Manufacture | | | | 29 Aug. 2005 | 30 Aug. 2005 | 9 Sep. 2005 |
| Phenotype | 2X DCB Formulation | FACS G-SOP-Q0007 | ≥95% CD105 ≥95% CD166 ≤1.25% CD45 | 96.72% CD105 98.37% CD166 0.10% CD45 | 98.05% CD105 97.35% CD166 0.10% CD45 | 99.42% CD105 99.40% CD166 0.01% CD45 |
| TNF RI | DCB Formulation | Sandwich ELISA | ≥108 pg/mL[1] | 602 pg/mL | 537 pg/mL | 372 pg/mL |
| Cell Line Species Identity | DCB Formulation | Isoenzyme electrophoresis | human cell line | human cell line | human cell line | human cell line |
| Karyology | DCB Formulation | cytogenic evaluation | no chromosomal abnormalities | no chromosomal abnormalities | no chromosomal abnormalities | no chromosomal abnormalities |

TABLE 6-continued

Clinical scale MSC preparations produced through passage 2

| | | | | | | |
|---|---|---|---|---|---|---|
| Sterility | 2X DCB Formulation packaged DCB (post thaw) | USP <71> Direct Method | Negative | Negative | Negative | Negative |
| Mycoplasma | pooled suspension | 1993 FDA PTC (Indirect and Direct method) | Negative | Negative | Negative | Negative |
| Endotoxin | 2X DCB Formulation packaged DCB (post thaw) | USP <85> (LAL; kinetic chromogenic) | ≤1.67 EU/mL | pass | pass | pass |
| Ultrastructural Evaluation of Cell Cultures for Viral Particles | DCB Formulation | Thin-Section TEM | Negative | Negative | Negative | Negative |
| in Vitro Assay for Detection of Adventitious Virus Contaminants | pooled suspension | MRC-5, VERO, and Hs68 cells | Negative | Negative | Negative | Negative |
| In Vitro Assay for Detection Adventitious Virus Contaminates | pooled suspension | USFDA | Negative | Negative | Negative | Negative |
| Detection of HTLV I & II | 2X DCB Formulation | DNA qPCR | Negative | Negative | Negative | Negative |
| Detection of Human HBV | 2X DCB Formulation | DNA qPCR | Negative | Negative | Negative | Negative |
| Detection of Human CMV | 2X DCB Formulation | DNA qPCR | Negative | Negative | Negative | Negative |
| Detection of Human EBV | 2X DCB Formulation | DNA qPCR | Negative | Negative | Negative | Negative |
| Detection of HHV-6A and HHV-6B | 2X DCB Formulation | DNA qPCR | Negative | Negative | Negative | Negative |
| Detection of HIV-1 | 2X DCB Formulation | DNA qPCR | Negative | Negative | Negative | Negative |
| Detection of HIV-2 | 2X DCB Formulation | DNA qPCR | Negative | Negative | Negative | Negative |
| Detection Parvovirus B-19 | 2X DCB Formulation | qRT-PCR | Negative | Negative | Negative | Negative |
| Detection of HCV | 2X DCB Formulation | DNA qPCR | Negative | Negative | Negative | Negative |
| Detection of Human Papilloma Virus (HPV) | DCB Formulation | DNA qPCR | Negative | Negative | Negative | Negative |
| Detection of HHV-8 | 2X DCB Formulation | DNA qPCR | Negative | Negative | Negative | Negative |

Example 31 Production of Clinical Scale MSC Preparations Through Passage 2

A collection of clinical scale preparations were produced and analyzed, as in Example 30. The results are depicted in Table 7, Table 8, and Table 9. As depicted, each preparation in the collection had an antigen profile of less than 1.25% CD45+ cells, at least 95% CD105+ cells, and at least 95% CD166+ cells. Also as depicted, each preparation in the collection had a TNFRI profile of at least 13 pg TNFRI per million cells. Each preparation was tested and determined to have a cell viability of at least 70% (data not shown).

TABLE 7

Clinical Scale MSC Preparations Produced Through Passage 2

| P2 Lot Number | Sterility[1] Negative | Mycoplasma PTC Negative | FACS CD166 (%) ≥95% | FACS CD105 (%) ≥95% | FACS CD45 (%) ≤1.25% | Sterility[2] Negative | Endotoxin[3] (EU/mL) ≤1.67 | TNF RI (pg/mL) ≥39 | IL-2Rα (%) ≥30% | Appearance Pass[4] |
|---|---|---|---|---|---|---|---|---|---|---|
| 7 | Negative | Negative | 99% | 99% | 0.00% | Negative | <0.100/<0.100 | 80 | 55% | Pass |
| 8 | Negative | Negative | 99% | 99% | 0.00% | Negative | <0.100 | 76 | 60% | Pass |
| 8[5] | Positive | N/A | 99% | 99% | 0.40% | Positive | <1.00/<1.00 | 88 | N/A | Pass |
| 9[5] | Negative | Negative | 99% | 99% | 0.00% | Positive | <1.00/<1.00 | 87 | N/A | Pass |
| 10 | Negative | Negative | 99% | 99% | 0.19% | Negative | <0.100/<0.100 | 100 | 57% | Pass |
| 11 | Negative | Negative | 100% | 99% | 0.00% | Negative | <0.100/<0.100 | 100 | 63% | Pass |
| 12 | Negative | Negative | 99% | 97% | 0.00% | Negative, Negative | <0.100/<0.100 | 126 | 57% | Pass |
| 13 | Negative | Negative | 99% | 98% | 0.00% | Negative, Negative | <0.100/<0.100 | 111 | 57% | Pass |
| 14 | Negative | Negative | 99% | 98% | 0.00% | Negative, Negative | <0.100/<0.100 | 121 | 69% | Pass |
| 15 | Negative | Negative | 99% | 99% | <0.50% | Negative | <0.100/<0.100 | 111 | 70% | Pass |
| 16 | Negative | Negative | 99% | 99% | <0.50% | Negative | <0.100 | 114 | 71% | Pass |
| 17[5] | Negative | Negative | 99% | 99% | <0.50% | Negative | <1.00 | 112 | 76% | Pass |
| 18 | Negative | Negative | 99% | 99% | <0.50% | Negative | 0.177 | 128 | 83% | Pass |

[1]Sterility testing is performed on the P2 2X intermediate Formulation sample.

[2]Sterility testing is performed on the final P2 packaged dose. Multiple test results indicate two bags were pulled for testing: one from controlled rate freezer #1 and one from controlled rate freezer #2. Both results must be negative for the lot to meet the sterility criterion.

[3]Endotoxin testing is performed on the final P2 packaged dose. Multiple test results indicate two bags were pulled for testing-one from controlled rate freezer #1 and one from controlled rate freezer #2. Both results must be ≤1.67 EU/mL for the P2 lot to meet the endotoxin criterion.

[4]Pass = Opaque contents, off-white to pale amber in color.

[5]N/A = Not applicable, no samples were available for testing due to microbial contamination

TABLE 8

Clinical Scale MSC Preparations Produced Through Passage 2

| P2 Lot Number | HCV Negative | CMV Negative | EBV Negative | HBV Negative | HHV-6 Variant A and Variant B Negative | HHV-8 Negative | HIV-1 Negative | HIV-2 Negative |
|---|---|---|---|---|---|---|---|---|
| 7 | Negative | Negative | Negative | Negative | Negative | Negative | Negative | Negative |
| 8 | Negative | Negative | Negative | Negative | Negative | Negative | Negative | Negative |
| 9[1] | N/A | N/A | N/A | N/A | N/A | N/A | N/A | N/A |
| 10 | Negative | Negative | Negative | Negative | Negative | Negative | Negative | Negative |
| 11 | Negative | Negative | Negative | Negative | Negative | Negative | Negative | Negative |
| 12 | Negative | Negative | Negative | Negative | Negative | Negative | Negative | Negative |
| 13 | Negative | Negative | Negative | Negative | Negative | Negative | Negative | Negative |
| 14 | Negative | Negative | Negative | Negative | Negative | Negative | Negative | Negative |
| 15 | Negative | Negative | Negative | Negative | Negative | Negative | Negative | Negative |
| 16 | Negative | Negative | Negative | Negative | Negative | Negative | Negative | Negative |
| 17 | Negative | Negative | Negative | Negative | Negative | Negative | Negative | Negative |
| 18[1] | Negative | Negative | Negative | Negative | Negative | Negative | Negative | Negative |
| 19 | Negative | Negative | Negative | Negative | Negative | Negative | Negative | Negative |

[1]N/A = Not applicable, no samples available for testing.

TABLE 9

Clinical Scale MSC Preparations Produced Through Passage 2

| P2 Lot Number | HTLV I & II | Parvovirus B-19 | HPV 18 | In-Vivo Assay for Viral Contaminants (mouse and egg) | In-Vitro Assay for Adventitious Viral Contaminants (MRC-5, VERO, Hs68 Cells) | Thin Section Electron Microscopy for Detection of Viral Particles | Cell Lines Identity Isoenzyme Electrophoresis | Karyology |
|---|---|---|---|---|---|---|---|---|
| 7 | Negative | Negative | Negative | Negative | Negative | Negative | Human Cell Lines | No Chromosomal Abnormalities |
| 8 | Negative | Negative | Negative | Negative | Negative | Negative | Human Cell Lines | No Chromosomal Abnormalities |
| 9[1] | N/A | N/A | N/A | N/A | N/A | N/A | N/A | N/A |
| 10 | Negative | Negative | Negative | Negative | Negative | Negative | Human Cell Lines | No Chromosomal Abnormalities |
| 11 | Negative | Negative | Negative | Negative | Negative | Negative | Human Cell Lines | No Chromosomal Abnormalities |
| 12 | Negative | Negative | Negative | Negative | Negative | Negative | Human Cell Lines | No Chromosomal Abnormalities |
| 13 | Negative | Negative | Negative | Negative | Negative | Negative | Human Cell Lines | No Chromosomal Abnormalities |
| 14 | Negative | Negative | Negative | Negative | Negative | Negative | Human Cell Lines | No Chromosomal Abnormalities |
| 15 | Negative | Negative | Negative | Negative | Negative | Negative | Human Cell Lines | No Chromosomal Abnormalities |
| 16 | Negative | Negative | Negative | Negative | Negative | Negative | Human Cell Lines | No Chromosomal Abnormalities |
| 17 | Negative | Negative | Negative | Negative | Negative | Negative | Human Cell Lines | No Chromosomal Abnormalities |
| 18[1] | Negative | Negative | Negative | Negative | Negative | Negative | Human Cell Lines | Clonal Chromosome Abnormalities |
| 19 | Negative | Negative | Negative | Negative | Negative | Negative | Human Cell Lines | No Chromosomal Abnormalities |

1N/A = Not applicable, no test samples available for testing.

Example 32 Production of Clinical Scale MSC Preparations Through Passage 5

Multiple clinical scale preparations were produced, each by the method set forth in Example 1 through Example 26, to produce a collection of preparations. Each preparation contained about $1\times10^{12}$ MSCs (up to about 8,000 doses after a freeze-thaw cycle) derived from a single donor with an average of about 12.5 population doublings compared to the P0 culture, or 25 total doublings. After thawing, a sample from each preparation was tested for antigen profile, TNFRI profile, cell viability, and capacity for differentiation. With the exception of TNFRI profile, each test was performed in the same manner described in Example 30. For the TNFRI profile, a TNFRI assay was performed in the same manner described in Example 30, and an assay of IL-2Ra expression inhibition was also determined as described below.

Inhibition of IL-2Ra expression on T-cells was determined by co-culturing MSCs with CD3/CD28-activated hPBMCs for 3 days, the time corresponding to the maximal level of IL-2Rα expression by the T-cell population in hPBMCs. The ratio of hMSCs to hPBMCs is 1:5, which was the optimal ratio identified for hMSC-mediated inhibition of lymphocyte proliferation tests. After incubation, cells were collected and lysed. The level of IL-2Rα in cell lysates was measured by ELISA. Results were expressed as % inhibition of IL-2Rα expression on CD3/CD28-stimulated hPBMCs by hMSCs relative to the control CD3/CD28 hPBMC cultured without hMSCs.

As shown in Table 10, each preparation in the collection had an antigen profile of less than 1.25% CD45+ cells, at least 95% CD105+ cells, and at least 95% CD166+ cells. Also as shown in Table 10, each preparation in the collection had a TNFRI profile of 13 to 179 pg TNFRI per million cells and inhibited IL-2Ra expression by at least 20% (at least 30%). Also as shown in Table 10, at least 70% (at least 80%) of the cells in each preparation were viable. Cells from each preparation had a capacity for chondrogenesis, osteogenesis, and adipogenesis (data not shown).

TABLE 10

Clinical scale MSC preparations produced through passage 5

| Test | Manufacturing Step | Test Method | 20* | 21* | 22* | 23* |
|---|---|---|---|---|---|---|
| | DCB Derived From | | Lot 2 | Lot 2 | Lot 2 | Lot 5 |
| | Date of Manufacture | | 10 Mar. 2006 | 17 Mar. 2006 | 21 Mar. 2006 | 20 Feb. 2007 |
| | Manufacturer | | OTI | OTI | OTI | LONZA |
| Sterility | pooled suspension | Negative | Negative | Negative | Negative | Negative |
| | packaged PD (post-thaw) | | Negative | Negative | Negative | Negative |
| Mycoplasma | pooled suspension | Negative | Negative | Negative | Negative | Negative |
| Endotoxin | pooed suspension | ≤1.67 EU/mL | <0.050 | <0.050 | <0.050 | <0.050 |
| | packaged PD (post-thaw) | | <0.25 | <0.25 | <0.025 | <0.25 |
| Viability | packaged PD (post-thaw) | ≥70% viable cells | 88 | 84 | 86 | 92 |
| Phenotype (Identity/Purity) | 2X PD Formulation | ≥95% CD105 ≥95% CD166 ≤1.25% CD45** | ≥98.91% CD105 ≥98.49% CD166 ≤0.00% CD45 | ≥98.17% CD105 ≥95.59% CD166 ≤0.04% CD45 | ≥98.52% CD105 ≥97.84% CD166 ≤0.45% CD45 | ≥99.53% CD105 ≥98.95% CD166 ≤0.03% CD45 |
| TNFRI (potency) | PD Formulation | Min: 272 pg/mL** Max: 1471 pg/mL | 961 | 900 | 963 | 995 |
| IL-2Ra (potency) | PD Formulation | ≤30% inhibition of Il-2Ra expression | N/A | N/A | N/A | 34 |
| Residual BSA | 2X PD Formulation | ≤10.0 ug/mL** | 3.0 | 1.08 | 3.05 | 3.11 |
| Residual Trypsin | 2X PD Formulation | ≤30.0 ug/mL** | 21.21 | 21.3 | <14.4 | <14.4 |
| Appearance** (cells in bag) | Packaged PD (post-thaw) | Opaque, off-white to pale amber, no fine particulates, no cell dumping*** | N/A | N/A | N/A | Pass |

| Test | Manufacturing Step | Test Method | 24* | 25* |
|---|---|---|---|---|
| | DCB Derived From | | Lot 5 | Lot 5 |
| | Date of Manufacture | | 22 Feb. 2007 | 23 Feb. 2007 |
| | Manufacturer | | LONZA | LONZA |
| Sterility | pooled suspension | Negative | Negative | Negative |
| | packaged PD (post-thaw) | | Negative | Negative |
| Mycoplasma | pooled suspension | Negative | Negative | Negative |
| Endotoxin | pooed suspension | ≤1.67 EU/mL | <0.050 | <0.050 |
| | packaged PD (post-thaw) | | <0.050 | <0.050 |
| Viability | packaged PD (post-thaw) | ≥70% viable cells | 94.8 | 86 |
| Phenotype (Identity/Purity) | 2X PD Formulation | ≥95% CD105 ≥95% CD166 ≤1.25% CD45** | ≥99.52% CD105 ≥99.51% CD166 ≤0.00% CD45 | ≥99.602% CD105 ≥99.47% CD166 ≤0.00% CD45 |
| TNFRI (potency) | PD Formulation | Min: 272 pg/mL** Max: 1471 pg/mL | 1269 | 1162 |
| IL-2Ra (potency) | PD Formulation | ≤30% inhibition of Il-2Ra expression | 58 | 62 |
| Residual BSA | 2X PD Formulation | ≤10.0 ug/mL** | 5.60 | 2.59 |
| Residual Trypsin | 2X PD Formulation | ≤30.0 ug/mL** | 14.4 | <14.4 |
| Appearance** (cells in bag) | Packaged PD (post-thaw) | Opaque, off-white to pale amber, no fine particulates, no cell dumping*** | Pass | Pass |

Example 33 Production of Clinical Scale MSC Preparations Through Passage 5

A collection of clinical scale preparations were produced and analyzed, as in Example 32.

Table 11 depicts the results of the preparation screen for the properties listed in Table 12 and the population density in the CFs. As depicted in Table 11, all preparations successfully analyzed passed the exemplary release criteria.

As depicted in Table 12, each preparation in the collection had an antigen profile of less than 1.25% CD45+ cells, at least 95% CD105+ cells, and at least 95% CD166+ cells.

Also as depicted in Table 12, each preparation in the collection had a TNFRI profile of at least 13 pg TNFRI per million cells.

Also as depicted Table 12, each preparation in the collection had a TNFRI profile of at least 13 pg TNFRI per million cells and inhibited IL-2Ra expression by at least about 20% (at least about 30%). Each preparation had a cell viability of at least about 70% (at least about 80%).

In order to determine if preparations could consistently be produced, the variance and standard deviation in the antigen profile, TNFRI profile, and cryopreservation profile were calculated as measures of deviation within the collection set forth in Table 12. The results are shown at the end of Table 12. As seen in Table 12, there is minimal deviation in the profiles (note that the cutoff value (preceded by a "<" symbol) was used for deviation calculation in certain instances where actual values were not determined).

TABLE 11

Clinical Scale MSC Preparations Through Passage 5

| P5 Lot Number | P2 Lot Used to Manufacture DP | Released if lot meets examplary criteria | Average Total Viable Cells/Cell Factory at Harvest |
|---|---|---|---|
| 26 | 7 | Released | $174 \times 10^6$ |
| 27 | 14 | Released | $168 \times 10^6$ |
| 28 | 14 | Released | $191 \times 10^6$ |
| 29 | 13 | Released | $122 \times 10^6$ |
| 30 | 13 | Released | $156 \times 10^6$ |
| 31 | 13 | Released | $181 \times 10^6$ |
| 32 | 13 | N/A | N/A |
| 33 | 13 | N/A | N/A |
| 34 | 14 | Released | $179 \times 10^6$ |
| 35 | 14 | Released | $121 \times 10^6$ |
| 36 | 14 | Released | $151 \times 10^6$ |
| 37 | 14 | Released | $121 \times 10^6$ |
| 38 | 14 | Released | $164 \times 10^6$ |
| 39 | 14 | Released | $164 \times 10^6$ |
| 40 | 14 | Released | $172 \times 10^6$ |
| 41 | 14 | Released | $201 \times 10^6$ |
| 42 | 14 | Released | $160 \times 10^6$ |
| 43 | 14 | Released | $142 \times 10^6$ |
| 44 | 14 | Released | $210 \times 10^6$ |
| 45 | 14 | Released | $237 \times 10^6$ |
| 46 | 14 | Released | $195 \times 10^6$ |
| 47 | 14 | Released | $173 \times 10^6$ |
| 48 | 14 | Released | $190 \times 10^6$ |
| 49 | 14 | Released | $168 \times 10^6$ |
| 50 | 14 | Released | $173 \times 10^6$ |
| 51 | 14 | Released | $162 \times 10^6$ |
| 52 | 8 | Released | $147 \times 10^6$ |
| 53 | 14 | Released | $169 \times 10^6$ |
| 54 | 14 | Released | $147 \times 10^6$ |
| 55 | 14 | Released | $166 \times 10^6$ |

P5 lots 32 and 33 were rejected prior to harvest due to an in process error. No QC samples were generated.

TABLE 12

Clinical Scale MSC Preparations Produced through Passage 5

| P5 Lot Number | Sterility[1] Negative | Mycoplasma PTC Negative | FACS CD166 (%) ≥95% | FACS CD105 (%) ≥95% | FACS CD45 (%) ≤75% | Sterility[2] Negative | Endotoxin (EU/mL) ≤1.67 EU/mL |
|---|---|---|---|---|---|---|---|
| 26 | Negative | Negative | 98 | 98 | <0.50 | Negative | 0.421 |
| 27 | Negative | Negative | 99 | 99 | <0.50 | Negative | <0.250 |
| 28 | Negative | Negative | 99 | 99 | 0.71 | Negative | <0.250 |
| 29 | Negative | Negative | 98 | 98 | <0.50 | Negative | <0.250 |
| 30 | Negative | Negative | 99 | 99 | <0.50 | Negative | <0.250 |
| 31 | Negative | Negative | 98 | 99 | 0.67 | Negative | <0.250 |
| 34 | Negative | Negative | 98 | 96 | 0.55 | Negative | <0.250 |
| 35 | Negative | Negative | 98 | 98 | <0.50 | Negative | <0.250 |
| 36 | Negative | Negative | 95 | 96 | <0.50 | Negative | <0.250 |
| 37 | Negative | Negative | 98 | 98 | <0.50 | Negative | <0.250 |
| 38 | Negative | Negative | 97 | 97 | <0.50 | Negative | <0.250 |
| 39 | Negative | Negative | 97 | 98 | <0.50 | Negative | <0.250 |
| 40 | Negative | Negative | 99 | 99 | <0.50 | Negative | <0.250 |
| 41 | Negative | Negative | 98 | 98 | <0.50 | Negative | <0.250 |
| 42 | Negative | Negative | 98 | 98 | <0.50 | Negative | <0.250 |
| 43 | Negative | Negative | 97 | 98 | <0.50 | Negative | <0.250 |
| 44 | Negative | Negative | 97 | 98 | <0.50 | Negative | <0.250 |
| 45 | Negative | Negative | 97 | 98 | <0.50 | Negative | <0.250 |
| 46 | Negative | Negative | 98 | 98 | <0.50 | Negative | 0.286 |
| 47 | Negative | Negative | 98 | 99 | <0.50 | Negative | 0.302 |
| 48 | Negative | Negative | 98 | 98 | <0.50 | Negative | <1.00 |
| 49 | Negative | Negative | 99 | 99 | <0.50 | Negative | 0.550 |

TABLE 12-continued

Clinical Scale MSC Preparations Produced through Passage 5

| | | | | | | | |
|---|---|---|---|---|---|---|---|
| 50 | Negative | Negative | 99 | 99 | <0.50 | Negative | 0.730 |
| 51 | Negative | Negative | 99 | 99 | <0.50 | Negative | <0.250 |
| 52 | N/A | Negative | 99 | 99 | <0.50 | Negative | <0.250 |
| 53 | Negative | Negative | 97 | 98 | <0.50 | Negative | <0.250 |
| 54 | Negative | Negative | 99 | 99 | <0.50 | Negative | 0.370 |
| 55 | Negative | Negative | 98 | 99 | 0.64 | Negative | <0.250 |
| 56 | Negative | Negative | 98 | 99 | <0.50 | Negative | <0.250 |
| 57 | Negative | Negative | 98 | 99 | <0.50 | Negative | 0.365 |
| 58 | Negative | Negative | 99 | 100 | <0.50 | Negative | 0.536 |
| 59 | Negative | Negative | 95 | 96 | <0.50 | Negative | <0.250 |
| 60 | Negative | Negative | 99 | 100 | <0.50 | Negative | <0.250 |
| 61 | Negative | Negative | 99 | 100 | <0.50 | Negative | <0.250 |
| 62 | Negative | Negative | 99 | 99 | <0.50 | Negative | <0.250 |
| Variance | | | 1.087395 | 1.011765 | 0.002524 | | |
| Standard Dev | | | 1.042782 | 1.005865 | 0.05024 | | |

| P5 Lot Number | Post Thaw Viability (%) ≥70% | Residual BSA (ug/mL) ≤10 ug/mL | Residual Trypsin (ug/mL) ≤30 ug/mL | TNF RI (pg/mL) Min: 108 Max: 368 | IL-2Rα (%) ≥30% | Appearance Pass[3] |
|---|---|---|---|---|---|---|
| 26 | 96 | 2 | <28.8 | 179 | 75 | Pass |
| 27 | 92 | 2 | <14.4 | 217 | 76 | Pass |
| 28 | 92 | 1 | <14.4 | 252 | 79 | Pass |
| 29 | 92 | 1 | <28.8 | 297 | 77 | Pass |
| 30 | 93 | 2 | <14.4 | 232 | 76 | Pass |
| 31 | 93 | 2 | <14.4 | 252 | 76 | Pass |
| 34 | 93 | 1 | <14.4 | 247 | 80 | Pass |
| 35 | 91 | 1 | <14.4 | 340 | 75 | Pass |
| 36 | 90 | 1 | <14.4 | 314 | 79 | Pass |
| 37 | 86 | 2 | <14.4 | 270 | 79 | Pass |
| 38 | 83 | 2 | <14.4 | 318 | 78 | Pass |
| 39 | 87 | 1 | <14.4 | 286 | 79 | Pass |
| 40 | 86 | 2 | <14.4 | 299 | 78 | Pass |
| 41 | 90 | 1 | <14.4 | 240 | 82 | Pass |
| 42 | 90 | 2 | <14.4 | 286 | 74 | Pass |
| 43 | 88 | 2 | <14.4 | 321 | 67 | Pass |
| 44 | 87 | 2 | <14.4 | 340 | 74 | Pass |
| 45 | 89 | 2 | <14.4 | 336 | 77 | Pass |
| 46 | 91 | 2 | <14.4 | 340 | 78 | Pass |
| 47 | 80 | 2 | <14.4 | 299 | 75 | Pass |
| 48 | 85 | 2 | <28.8 | 314 | 85 | Pass |
| 49 | 93 | 2 | <14.4 | 335 | 76 | Pass |
| 50 | 90 | 3 | <28.8 | 306 | 85 | Pass |
| 51 | 92 | 3 | <14.4 | 304 | 79 | Pass |
| 52 | 94 | 2 | <14.4 | 300 | 67 | Pass |
| 53 | 94 | 2 | <14.4 | 323 | 78 | Pass |
| 54 | 91 | 3 | <14.4 | 301 | 81 | Pass |
| 55 | 93 | 4 | <14.4 | 328 | 71 | Pass |
| 56 | 92 | 3 | <14.4 | 277 | 68 | Pass |
| 57 | 93 | 4 | <14.4 | 313 | 71 | Pass |
| 58 | 91 | 3 | <14.4 | 330 | 69 | Pass |
| 59 | 88 | 2 | <14.4 | 334 | 67 | Pass |
| 60 | 94 | 3 | <14.4 | 273 | 66 | Pass |
| 61 | 86 | 2 | <28.8 | 333 | 76 | Pass |
| 62 | 92 | 3 | <14.4 | 359 | 75 | Pass |
| Variance | 12.16471 | 0.633613 | | 1648.706 | 23.99664 | |
| Standard Dev | 3.487794 | 0.795998 | | 40.60426 | 4.898636 | |

Example 34 Analysis of Profile Deviation

In order to determine if preparations could consistently be produced, the variance and standard deviation in the antigen profile, TNFRI profile, and cryopreservation profile were calculated as measures of deviation within the collection set forth in Table 10. The results are shown in Table 13. As seen in Table 13, there is minimal deviation in the profiles.

TABLE 13

Consistent Production of MSC Preparations

| Preparation | Antigen Profile | | | TNFRI Profile | | Cryopreservation Profile |
| | % CD105+ | % CD166+ | % CD45+ | TNFRI | % IL-2Ra inhibition | % Viability |
| --- | --- | --- | --- | --- | --- | --- |
| 20 | 98.91 | 98.49 | 0.00 | 961 | NA | 88 |
| 21 | 98.17 | 95.59 | 0.04 | 900 | NA | 84 |
| 22 | 98.52 | 97.84 | 0.45 | 963 | NA | 86 |
| 23 | 99.53 | 98.95 | 0.03 | 995 | 34 | 92 |
| 24 | 99.52 | 99.51 | 0.00 | 1,269 | 58 | 94.8 |
| 25 | 99.60 | 99.47 | 0.00 | 1,192 | 62 | 86 |
| Variance | 0.31 | 1.81 | 0.027 | 18,200 | 152.9 | 14.2 |
| Standard Dev | 0.552347 | 1.34455 | 0.163 | 134.8 | 12.36 | 3.76 |

Example 35 Consistent Proliferation

An analysis of cellular proliferation was used to assess process consistency, although cells from different donors will have different proliferation potential. The evaluation of the total cells harvested for each MSC preparation also allows for the identification of any out of trend values. One measure of process consistency is the number of cells per CF, since it reflects the uniformity of the process performance. However, due the inherent biological variability of the preparation of a cellular product, the process will always be subject to a certain level of variability.

The number of cells recovered per CF was evaluated at two passages during the manufacture of MSC preparations. The number of cells per CF after the third passage (see Example 17) and the fifth passage (see Example 23) for several MSC preparations is presented with descriptive statistics in Table 14. At P3, the average number of cells per CF was about 190 million, and the standard deviation was 67. At P5, the average number of cells per CF was about 166 million, and the standard deviation was 35.

TABLE 14

Cellular Proliferation

| PD Lot # | DCB Lot # | Passage 3 (P3) Cells/CF (in millions) | Harvest (P5) Cells/CF (in millions) |
| --- | --- | --- | --- |
| 63 | 63 | 238 | 154 |
| 64 | 63 | 116 | 141 |
| 65 | 63 | 116 | 126 |
| 66 | 63 | 315 | 148 |
| 67 | 63 | 157 | 117 |
| 68 | 63 | 154 | 141 |
| 69 | 2 | 122 | 188 |
| 70 | 1 | 71 | 162 |
| 71 | 1 | 143 | 140 |
| 72 | 3 | 118 | 124 |
| 73 | 3 | 134 | 102 |
| 74 | 2 | 163 | 189 |
| 75 | 2 | 229 | 238 |
| 76 | 2 | 229 | 197 |
| 77 | 2 | 246 | 208 |
| 78 | 2 | 246 | 174 |
| 79 | 2 | 202 | 218 |
| 20 | 2 | 202 | 153 |
| 80 | 2 | 194 | 180 |
| 21 | 2 | 194 | 172 |
| 81 | 2 | 295 | 185 |
| 22 | 2 | 295 | 186 |
| Mean | | 190 | 166 |
| Std. Dev. | | 67 | 35 |

Example 36 Evaluation of Cryoprotectant Fill Time

Product formulation and bag fill time ranges for an exemplary ex viva cultured mesenchymal stem cells manufacturing process was performed to evaluate the effects of the cryoprotectant solution on cells to determine an exemplary time range for formulation and fill prior to cryopreservation. Four time points were evaluated: 60, 90 (control), 150 and 240 minutes. At one day and thirty days post-cryopreservation, hMSCs were thawed and evaluated for viability (Table 15), phenotype (Table 16) and expression of TNFRI (patency) (Table 17) against this exemplary acceptance criteria. Results of the study showed that cell quality is not affected, for example, when product formulation and fill occurs within 150 or 240 minutes prior to cryopreservation.

TABLE 15

Effect of Different Formulation/Fill Times on Post-Thaw Cell Viability

| Time for Formulation/Fill | Example Acceptance Criteria for Post-Thaw Cell Viability (%) | Post-Thaw Cell Viability (%) |
|---|---|---|
| One Day Storage After Cryopreservation | | |
| 60 minutes | ≥70 | 87.3 |
| 90 minutes (control) | ≥70 | 87.6 |
| 150 minutes | ≥70 | 85.3 |
| 240 minutes | ≥70 | 90.5 |
| 30 Days Storage After Cryopreservation | | |
| 60 minutes | ≥70 | 87.4 |
| 90 minutes (control) | ≥70 | 80.3 |
| 150 minutes | ≥70 | 92.1 |
| 240 minutes | ≥70 | 88.8 |

TABLE 16

Effect of Different Formulation/Fill Times on Cell Phenotype
Positively stained cells (%)

| Time for Formulation/Fill | Example CD166 (%) Acceptance Criteria | CD166 (%) | Example CD105 (%) Acceptance Criteria | CD105 (%) | Example CD45 (%) Acceptance Criteria | CD45 (%) |
|---|---|---|---|---|---|---|
| One Day Storage After Cryopreservation | | | | | | |
| 60 minutes | ≥95 | 98.28 | ≥95 | 99.07 | ≤0.75 | 0.37 |
| 90 minutes(control) | ≥95 | 99.19 | ≥95 | 99.47 | ≤0.75 | 1.57[x] |
| 150 minutes | ≥95 | 98.58 | ≥95 | 99.08 | ≤0.75 | 0.11 |
| 240 minutes | ≥95 | 97.97 | ≥95 | 98.99 | ≤0.75 | 0.26 |
| 30 Days Storage After Cryopreservation | | | | | | |
| 60 minutes | ≥95 | 96.07 | ≥95 | 98.08 | ≤0.75 | 0 |
| 90 minutes(control) | ≥95 | 96.75 | ≥95 | 98.81 | ≤0.75 | 0.21 |
| 150 minutes | ≥95 | 96.12 | ≥95 | 98.56 | ≤0.75 | 0 |
| 240 minutes | ≥95 | 95.21 | ≥95 | 98.62 | ≤0.75 | 0 |

[x]Investigation showed that the out of specification result was not a result of the test condition.

TABLE 17

Effect of Different Formulation/Fill Times on TNF RI Expression

| Time for Formulation/Fill | Example Acceptance Criteria TNFRI (pg/mL) | TNF RI Expression (pg/mL) |
|---|---|---|
| One Day Storage After Cryopreservation | | |
| 60 minutes | 108 ≤ TNFRI ≤ 368 | 188 |
| 90 minutes (control) | | 280 |
| 150 minutes | | 258 |
| 240 minutes | | 267 |
| 30 Days Storage After Cryopreservation | | |
| 60 minutes | 108 ≤ TNFRI ≤ 368 | 318 |
| 90 minutes (control) | | 298 |
| 150 minutes | | 312 |
| 240 minutes | | 368 |

Example 37 Karyotyping

The karyotype of an hMSC sample is determined through examination of colcemid-arrested metaphase spreads. The hMSCs are cultured briefly, arrested with colcemid and processed. The cells are enlarged using a hypotonic HEPES buffered EGTA solution, fixed, and then the cells are enlarged using a hypotonic HEPES buffered EGTA solution, fixed, and then placed on microscope slides. The slides are aged overnight, treated with trypsin, and stained with Giemsa to produce G-banding. Typical G-banding should yield about 350-450 positive G bands. Standard evaluation includes enumeration of numerical and structural abnormalities ('chromosomal abnormalities'), such as translocations, breaks, rings, markers and double-minutes, with at least 20 cells evaluated. Inversion, deletion, or translocation breakpoints are identified as per the ISCN 1995 International System for Human Cytogenetic Nomenclature, when possible. At least two karyotypes per sample are prepared. Results of karyotyping show that exemplary preparations of the present invention have no chromosomal abnormalities (Table 4, Table 6, and Table 9).

Example 38 Pathogen Contaminants

Testing for Adventitious Agents. The preparations of the present invention can be made without being compromised by adventitious agents (pathogens). A useful preparation is optionally screened for the following pathogens.

Sterility. The sterility of the test article is determined by the Direct Inoculation Method (Direct Method) in accordance with <USP 71> Sterility Test. The test conforms to the standard 14-day incubation period under aerobic and anaerobic conditions. Fluid Thioglycollate Medium is used for the culture of anaerobic bacteria and Soybean-Casein Digest (SCD) Medium is used for both fungi and aerobic bacteria. A test Negative result is no growth of microorganisms after 14 days incubation. Validation of the test method includes the following strains of test microorganisms: FTM (anaerobic)—[*B. subtillis* (ATCC 6633, *K. rhizophilia* (ATCC 9341), and *C. sporogenes* (ATCC 11437)] and SCD (aerobic and fungi)—[*B. subtillis* (ATCC 6633); *C. albicans* (ATCC 10231), and *A. niger* (ATCC 16404)].

Mycoplasma. Both indirect and direct methods are used.
 i. The indirect method allows visualization of *Mycoplasma* in a co-cultured indicator cell line (Vero cells). The test article hMSCs are co-cultured with Vero cells on coverslips. Positive controls for the test are Vero cells inoculated with the *Mycoplasma* species *M. hyorhinis* and *M. orale*. The negative control is Vero cells inoculated with sterile broth. Mycoplasmas are identified by epifluorescent detection of a DNA-binding fluorochrome stain (Hoechst stain). In negative controls, only the Vero cell nucleus is stained, whereas in positive controls, both nuclear and extra-nuclear fluorescence is detected. *Mycoplasma* exhibit a staining pattern that differs from the host Vero cells, and consists of extra-nuclear staining of small round bodies of approximately 0.3 μm in diameter.

ii. The direct method allows detection of *Mycoplasma* growth under aerobic and anaerobic conditions (broth culture flasks and agar plates, respectively). The agar and broth media supply nutrients and a source of carbon and energy necessary for *Mycoplasma* growth. Positive controls consist of cultures inoculated with nonfermentative and fermentative *Mycoplasma* species (*M. orale* and *M. pneumoniae*, respectively), while sterile broth serves as a negative control. Indicators of *Mycoplasma* growth include change in color or turbidity of broth cultures, and growth of colonies with "fried egg" morphology on agar plates.

Negative results for *Mycoplasma* contamination of the hMSC test sample are defined as results for both indirect and direct methods that resemble the respective negative controls. This test is governed by an OTI-approved protocol executed by an external testing laboratory (AppTec protocol 30055).

Endotoxin. Endotoxin levels in the test article are determined by the Limulus Amebocyte Lysate (LAL) method in accordance with <USP 85>. This test is a quantitative, chromogenic kinetic assay for the detection of gram-negative bacterial endotoxin. The concentration of endotoxin in the test article is calculated from a standard curve using a series of endotoxin standards. The assay is validated to ensure the test article does not inhibit or enhance detection of endotoxin. A positive product control (PPC) is included to ensure the sample dilution is valid.

Ultrastructural Evaluation of Cell Cultures for Viral Particles. The ultrastructural morphology of an hMSC sample will be evaluated by thin-section transmission electron microscopy (TEM) to determine the following:

Presence of a variety of viral types including retroviruses, herpesviruses, adenoviruses, picornaviruses, parvoviruses, orthomyxoviruses, paramyxoviruses, and reoviruses.

Presence of other microbial agents such as yeast, fungi or bacteria.

Incidence of specific retroviral morphologies (A-, B- C-, D- and R-type particles).

The test article is cultured briefly and the harvested. The cells are harvested, fixed, embedded, and sectioned for analysis by TEM. Two hundred cells are evaluated for any particle with virus-like morphology. A tabulation of retrovirus-like particles is undertaken. A blank water sample serves as the negative control.

In Vivo Test for Detection of Adventitious Viruses (Viral Contaminants)

The in-vivo viral test assay is designed to detect murine and non-murine viruses that would not be detected by the in vitro viral test. The assay sensitivity is increased by sub-passage of materials from mice and eggs into new test systems. The test article is prepared as a clarified lysate supernatant and inoculated into the following:

Adult mice (intraperitoneal and intracerebral administration). Adult mice are susceptible to various viral agents (including coxsackieviruses, flaviviruses). Daily health observations of the adult mice are performed and they are sacrificed 21 days after inoculation, or possibly sooner if group mortality exceeds 20%.

Newborn suckling mice (intraperitoneal and intracerebral administration). Suckling mice are susceptible to various agents, including togaviruses, bunyaviruses, flaviviruses, picornaviruses, and herpes viruses. The newborn suckling mice are observed for 14 days post administration for ill effects, or possibly sooner if group mortality exceeds 20%. At that time the mice are sacrificed, their tissues pooled, and homogenized for subpassage into another set of newborn suckling mice through the same routes of administration. This group is monitored for 14 days. Animals found dead within 24 hours of injection have their tissues homogenized and sub-passaged into a fresh group of animals.

Embryonated hen eggs (allantois and yolk sac administration) is used to test for viruses. Inoculation via the allantois favors propagation of orthomyxoviruses, and paramyxoviruses. Inoculation via the yolk sac favors replication of herpes viruses, rickettsiae, *Mycoplasma*, and bacteria.

Embryonated hen's eggs inoculated via the allantoic cavity (first passage) are incubated for three days and the embryos are observed for viability. Allantoic fluids from this first passage are harvested (including fluids from dead eggs) for a hemagglutination assay (to quantify viral particles) or for sub-passage into a fresh set of eggs. The second passage eggs follow the same time course, at the end of which the allantoic fluids are harvested for a hemagglutination assay and an examination of the embryos.

Eggs inoculated via the yolk sac (first passage) are incubated for nine days and are observed for viability. After the 9-day incubation, all embryos are harvested and examined. All first passage yolk sacs are harvested, washed, and pooled; second passage eggs are inoculated with a preparation of this material. Second passage eggs, along with the negative control, are incubated for 9 days and are candled each working day for viability. After the 9 day incubation all embryos are harvested and examined.

The hemagglutination assay uses chicken, guinea pig, and human type-O erythrocytes. Replicate plates are observed after incubation for hemagglutination.

A negative control is prepared for each set in the study group with an inoculation of Eagle's Minimal Essential Medium and processed and analyzed in the same manner as the study group. A test article is considered negative for adventitious agents if: 1) at least 80% of adult and suckling mice (first and second passage) survive the test period in good health; 2) at least 80% of inoculated hen embryos survive the test period and are normal in appearance; and 3) the fluids collected from inoculated embryos do not produce hemagglutination.

In vitro test for Detection of Adventitious Viruses. The in vitro viral test is designed to detect various viruses, including picornaviruses, orthomyxoviruses, paramyxoviruses, herpesviruses, adenoviruses, and reoviruses. Test article is incubated with three indicator cell lines (MRC-5, a human embryonic cell line; VERO, a simian kidney cell line; Hs68, a human foreskin cell line). The inoculated cultures are examined for at least 28 days and compared to positive controls for the development of cell morphology characteristic of viral contamination. Picomaviruses, herpesviruses, adenoviruses, and reoviruses can be detected by changes in morphology directly. However, orthomyxo- and paramyxoviruses may replicate in these cell lines with little or no cytopathic manifestation. The presence of these viruses is detected by the ability to adsorb erythrocytes to the surface of infected cells (hemadsorption assay) which is performed at the conclusion of the observation period.

HTLV I & II. Testing for human T-cell lymphotropic viruses I and II (HTLV-1 and HTLV-II) is designed to detect the presence of HTLV-1 and HTLV-2 proviral DNA tax gene sequences in test article. The assay limit of detection is 10-100 infected cell equivalents of HTLV I or HTLV II DNA. The test method is based upon PCR amplification of a conserved region of the viral genome containing the tax/rex locus (the tax and rex loci encode proteins essential for viral replication). The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral DNA copy number. A negative result is defined as a fluorescence signal below the limit of detection (lowest copy number detected above background).

HBV. The human hepatitis B virus (HBV) assay is a limit test designed to detect the presence of HBV DNA sequences, down to 10-100 copies of HBV viral DNA in the test article. The test method is based upon PCR amplification of the S region of the HBV genome, yielding a 194 bp amplification product. The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral DNA copy number. A negative result is defined as a fluorescence signal below the limit of detection (lowest copy number detected above background).

CMV. The human cytomegalovirus (CMV) assay is a limit test designed to detect the presence of CMV DNA sequences (as few as 10-100 DNA copies) in the test article. The test method is based upon PCR amplification of a region of the viral genome containing a highly conserved Hind III-X fragment, yielding a 311 bp amplification product. The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral DNA copy number. A negative result is defined as a fluorescence signal below the limit of detection (lowest copy number detected above background).

EBV. The human Epstein-Barr virus (EBV) assay is a limit test designed to detect the presence of EBV gene sequences (as few as 10-100 EBV DNA copies) in the test article. The test method is based upon PCR amplification of a region of the EBV major capsid protein (MCP) gene, yielding a 212 bp amplification product. The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral DNA copy number. A negative result is defined as a fluorescence signal below the limit of detection (lowest copy number detected above background).

HHV-6 Variant A (HHV-6A) and Variant B (HHV-6B). The assay for human herpesvirus 6, variant A (HHV-6A) and variant B (HHV-6B) is a limit test designed to detect the presence of HHV-6A and HHV-6B DNA sequences in the test article (as few as 10-100 copies of HHV-6A and 6B DNA). The test method is based upon PCR amplification of a region of the viral genome encompassing the U65-U66 genes, yielding a 196 bp amplification product. The primers were derived from HHV-6A but also amplify an identical sequence in HHV-6B. The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral DNA copy number. A negative result is defined as a fluorescence signal below the limit of detection (lowest copy number detected above background).

HIV-1. The human immunodeficiency virus type 1 (HIV-1) assay is a limit test designed to detect the presence of HIV-1 gag region DNA sequences in the test article (as few as 10-100 HIV-1 DNA copies). The test method is based upon PCR amplification of a region of the viral genome encompassing the gag locus, yielding a 140 bp amplification product. The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral DNA copy number. A negative result is defined as a fluorescence signal below the limit of detection (lowest copy number detected above background).

HIV-2. The human immunodeficiency virus type 2 (HIV-2) assay is a limit test designed to detect the presence of HIV-2 gag region DNA sequences in the test article (as few as 50-500 infected cell equivalents of HIV-2 viral DNA). The test method is based upon PCR amplification of a region of the viral genome, encompassing the gag locus, yielding a 196 bp amplification product. The specific amplicon is detected through use of a FITC-labeled donor probe and an LC640-labeled acceptor probe to provide a quantitative, real-time, sequence-specific analysis using a Roche LightCycler™. The fluorescence is detected and correlates to the number of infected cell equivalents. A negative result is defined as a fluorescence signal below the limit of detection. This test is governed by an OTI-approved protocol executed by an external testing laboratory.

Parvovirus B-19. The parvovirus B-19 assay is a limit test designed to detect the presence of parvovirus B-19 VP1 region DNA sequences in the test article (as few as 10-100 B-19 viral DNA copies). The test method is based upon PCR amplification of a region of the viral genome, within the VP1 gene, yielding a 208 bp amplification product. The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral DNA copy number. A negative result is defined as a fluorescence signal below the limit of detection (lowest copy number detected above background).

HCV. The human hepatitis C virus (HCV) assay is a limit test designed to detect the presence of HCV RNA sequences in the test article (as few as 1-10 HCV virus genomes). The test method is based upon reverse transcriptase-mediated synthesis of DNA complementary to viral RNA present in the test article, followed by PCR amplification of the highly conserved 5' untranslated region of the HCV genome, yielding a 297 bp amplification product. The specific amplicon is detected through use of a FITC-labeled donor probe and an LC640-labeled acceptor probe to provide a quantitative, real-time, sequence-specific analysis using a Roche LightCycler™. The fluorescence is detected and correlates to viral copy number. A negative result is defined as a fluorescence signal below the limit of detection (lowest copy number detected above background).

HPV Type 18. This is a new assay implemented post Q4 2006 to replace the HPV assay. The human papillomavirus type 18 (HPV 18) assay is a limit test designed to detect viral DNA in the test article (as few as 1-10 copies/infected cell equivalent (ICE)/plaque-forming unit (Pfu). The test method is based upon PCR amplification of a region of the viral genome, within the E6/E7 region, yielding a 208 bp amplification product. The specific amplicon is detected using a quantitative, real-time, sequence-specific analysis using a Roche LightCycler™. The presence of amplified HPV target DNA is confirmed by DNA probe specific hybridisation with a fluorescence-labeled HPV oligonucleotide probe that identifies an internal sequence of 208 bp Amplicon. The fluorescence is detected and correlates to viral particle number. A negative result is defined as a fluorescence signal below the limit of detection (lowest viral particle number detected above background).

HHV-8. The human herpesvirus 8 (HHV-8) assay is a limit test designed to detect the presence of HHV-8 IE1A gene DNA sequences (10-100 infected cell equivalents of HHV-8 DNA) in test article. The test method is based upon PCR amplification of a region of the viral genome, encompassing the IE1A gene, yielding a 264 bp amplification product. Amplified reaction products are then fractionated on an agarose gel, blotted by the Southern method onto a DNA binding membrane, and probed with a radiolabeled oligonucleotide homologous to a DNA sequence embedded within the 264 bp-amplified product. Amplicon-specific radioactivity is measured by autoradiography.

Example 39 Aseptic Processing

Certain steps occurred throughout the manufacturing process to control the environment. To reduce potential contamination, the Terumo® Sterile Tubing Welder and the Sebra® MINI™ Hand Held Tube Sealer were utilized to permit closed processing. Steps that used the welder and sealer included: transfer of BMA and fluids, sampling, seeding of CFs, feeds, passages, harvest, formulation, fill and cryopreservation. All welds and seals were visually inspected for integrity. If the integrity of a seal or weld has been breached (exposed to air), then the affected portion of the material will be discarded.

Example 40 Control of Tube Welding for Aseptic Processing

In all processing steps, tube to tube welding (cell factories (CFs), solution bags and cryopreservative (e.g., Cryocyte™) freezing containers) was surprisingly useful to implement controls to reduce potential contamination. All welding of tubing was performed using the Terumo® Sterile Tubing Welder. This welder has been designed for use in the storage and handling of blood products. The system automatically connects in a sterile manner two sections of tubing. The welds were visually inspected to ensure integrity by rotating the tubing 360° to determine if the outer diameters of the two tubes were aligned at the connection (weld). If the welds were determined to be breached (exposed to air), then the affected portion of material was discarded. If properly aligned, each weld was opened by pinching or rolling the tubing until the fluid pathway opens. Process steps that are surprisingly enhanced by welding include, for example, transfer of BMA and fluids, sampling, seeding of CFs, feeds, passages, harvest, formulation and fill.

Example 41 Control of Tube Seals for Aseptic Processing

Processing steps that require tubing to be sealed or severed utilized the Sebra® MINI™ Hand Held Tube Sealer. The tube sealer is an instrument for making seals on tubing made of Radio Frequency (RF)-reactive thermoplastic materials used in blood banks, blood processing facilities and transfusion centers. The sealer is an instrument that generates a controlled amount of RF energy at the sealing head while mechanically compressing the tubing across its diameter during the dielectric sealing and forming process. When the energy is removed and the tubing is allowed to cool under compression, a permanent seal is produced. During processing, the seals were inspected visually for integrity. If a seal was determined to be breached (exposed to air), that portion of material was discarded. Process steps that are surprisingly enhanced by seals include transfer of BMA and fluids, sampling, seeding of CFs, feeds, passages, harvest, formulation, fill and cryopreservation.

Example 42 Therapeutic Efficacy of Clinical Scale Preparations

A clinical scale preparation was prepared as detailed in Example 1 through Example 26. The preparation was partitioned into therapeutic doses and administered to pediatric aGVHD patients.

Eight biweekly therapeutic doses of $2 \times 10^6$ cells/kg were administered by infusion to 59 children with steroid (and other therapeutic agent)-refractory Grade B-D aGVHD. An additional 4 weekly infusions were administered after day 28 in patients who had a response.

At baseline, the distribution of aGVHD grades B:C:D was 6 (10%): 20 (33%): 33 (57%). The median duration of aGVHD before enrollment was 29 days, and patients failed an average of 3.2 lines of treatment for GVHD. Organ involvement was 60% skin, 87% gastrointestinal, and 38% liver. At day 28, overall response (OR), defined as organ improvement of at least one stage without worsening in any other, was 64%; 17% of patients had stable disease or mixed response; and 19% experienced progression. By grade, 28 day OR was 67% for B, 75% for C, and 58% for D. Response by organ was recorded, with 47% of skin, 23% of GI, and 39% of liver GVHD completely responding (stage 0) within the first 28 days of treatment.

Overall survival through study duration (day 100) was 62%. Achieving an OR at day 28 resulted in a significantly higher probability of survival when compared to patients who progressed within the first 28 days (76% vs 9%, p<0.05). The MSCs were well tolerated and there was no evidence of ectopic tissue formation.

These results demonstrate that preparations of the present invention are surprisingly therapeutically effective, even when expanded on a large (clinical) scale.

Example 43 Therapeutic Efficacy of Clinical Scale Preparations

Pediatric patients (<18 years) with grade B-D SR-GVHD were randomized to receive MSCs from a clinical scale preparation produced by the method detailed in Example 1 through Example 26 or placebo, in addition to standard of care, including institutionally selected second line agent. Patients received 8 therapeutic doses of $2 \times 10^6$ cells/kg for 4 weeks (or volume equivalent for placebo), with 4 more infusions weekly in patients who had a response. The primary endpoint was durable complete response (CR>28 days); secondary endpoints included incidence of CR, overall response (OR=CR+PR), progression through 100 days, and survival.

Twenty-eight children were randomized to MSC treatment (50% male, 79% Caucasian) or placebo (71% male, 71% Caucasian), with a median age of 7 years (range 1-15) and 10 years (range 1-18), respectively. The dominant transplant graft was cord blood (71% MSC, 57% placebo), with mostly unrelated donors (93% vs 79%, respectively). The median duration of aGVHD prior to enrollment was 20 days for MSC treatment and 8 days for placebo (p<0.05). At baseline, aGVHD grades B:C:D were 3:8:3 for both arms. For MSC treatment, organ involvement was 64% skin, 43% GI, and 36% liver. For placebo patients, organ involvement was 57% skin, 79% GI, and 29% liver. Durable CR was 64% for MSC treatment and 43% for placebo. CR for MSC treatment vs placebo, respectively, was 36% vs 21% at day 28, 57% vs 21% at day 42, and 64% vs 29% at day 100. OR for MSC treatment vs placebo, respectively, was 64% vs 34% at day 28, 64% vs 50% at day 42, and 71% vs 50% at day 100. Progression for MSC treatment vs placebo, respectively, was 14% vs 50% at day 28, 29% vs 43% at day 42, and 21% vs 43% at day 100.

Survival for MSC treatment vs placebo, respectively, was 93% vs 86% at day 28, 79% vs 79% at day 42, and 79% vs 50% at day 100. The median time to CR was 25 days vs 63 days. The 25% percentile of the survival function after study start was 139 days for MSC treatment and 50 days for placebo.

These results demonstrate that preparations of the present invention are surprisingly therapeutically effective, even when expanded on a large (clinical) scale.

Example 44 Therapeutic Efficacy of Clinical Scale Preparations 244 patients with grade B-D SR-GVHD (skin involvement n=144, GI involvement n=179, liver involvement n=61) were randomized to receive MSCs from a clinical scale preparation produced by the method detailed in Example 1 through Example 26 (n=163) or placebo (n=81), in addition to standard of care, including institutionally selected second line agent. Patients received 8 therapeutic doses of $2 \times 10^6$ cells/kg for 4 weeks (or volume equivalent for placebo), with 4 more infusions weekly in patients who responded. The primary endpoint was durable complete response (CR>28 days).

For the MSC treatment and placebo arms, respectively, the grades of GVHD at entry were B (22% vs. 26%), C (51% vs. 58%), and D (27% vs 16%). The respective durable CR rates were 35% vs. 30% (p=0.3) in the ITT population and 40% vs. 28% (p=0.08) in the per protocol population. Patients with GVHD affecting all 3 organs had an overall complete or partial response rate of 63% vs. 0% (n=22, p<0.05) at day 28. Patients treated with MSCs had less progression of liver GVHD at weeks 2 and 4 respectively (32% vs 59%, p=0.05; and 37% vs. 65%, p=0.05).

The overall response (OR) results at day 100 were 82% in the MSC-treated group and 73% in the placebo group.

The partial response results at day 100 for the MSC-treated group and placebo group, respectively, were: Skin, 78% and 77%; Liver, 76% and 47%; Gut, 82% and 68%.

These results demonstrate that preparations of the present invention are surprisingly therapeutically effective, even when expanded on a large (clinical) scale.

Example 45 Therapeutic Efficacy of Clinical Scale Preparations

Patients with grades II-IV GVHD were randomized to receive human MSCs derived from a clinical scale preparation produced by the method detailed in Example 1 through Example 26 in 2 therapeutic doses of either 2 or 8 million MSCs/kg in combination with corticosteroids. The study evaluated induction of response to MSC therapy, and overall response of aGVHD by day 28. Thirty-one patients were evaluated: 21 males, 10 females; median age 52 years (range: 34-67). Twenty-one patients had grade II, 8 had grade Ill, and 3 had grade IV aGVHD. Ninety-four percent of patients had an initial response to MSC therapy (77% complete response and 16% partial response).

These results demonstrate that preparations of the present invention are surprisingly therapeutically effective, even when expanded on a large (clinical) scale.

Example 46 Variant Preparations

Using the methodologies generally set forth in Example 1-Example 41, a manufacturing facility produced multiple preparations of MSCs. Of the 27 independent preparations manufactured that were fully analyzed (until a failure was identified), labeled according to the manufacturing protocol, and successfully passed sterility and visual appearance tests, 14 preparations met the following criteria:

| | |
|---|---|
| CD 166+: | ≥95% |
| CD 105+ | ≥95% |
| CD 45– | ≥99.25% |
| Post-thaw viability: | ≥75% |
| Residual BSA | ≥10 µg/ml |
| Residual Trypsin | ≤30 µg/ml |
| TNFRI | 108-368 pg/ml |
| IL2-Ra | ≥30% inhibition |

Of the 13 that failed to meet one or more criteria, 8 failed to demonstrate potency based upon the IL-2Ra test, 4 failed to demonstrate potency based upon TNF R1 expression, and 2 had excess residual trypsin levels. One of the preparations failed the TNFRI assay also failed the IL-2Ra assay.

These results demonstrate that MSC preparations can show heterogeneity, even when standardized procedures are followed. Thus, the skilled artisan should now recognize that MSC preparations in the art that appear equivalent based one or even several criteria may, in fact, have important phenotypic or genotypic differences between them and may not demonstrate the potency that characterizes the MSC preparations of the present invention. Moreover, the MSC preparations of the present invention can be distinguished from many of the preparations in the prior art upon complete characterization as taught here.

Example 47 Variant Preparations

At another manufacturing facility (i.e. different facility than in Example 46), the methodologies set forth in Example 1-Example 41 were generally followed. Greater than 95% of the lots met the criteria of Example 46. However, one preparation failed post-thaw viability test and the TNFR1 assay for potency. Another preparation failed the residual trypsin analysis, having a value of 38.1 µg/mL. These results demonstrate the importance of adding a screening step to the manufacturing methods, even when highly reproducible techniques have been achieved.

The citations provided herein are hereby incorporated by reference for the cited subject matter.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

What is claimed is:

1. A mesenchymal stem cell (MSC) preparation comprising:
cultured human bone-marrow-derived MSCs expanded from a cryopreserved in-process intermediate MSC preparation; wherein the cultured human bone-marrow-derived MSCs
   (a) have an antigen profile comprising:
      i. less than 0.75% CD45+ cells;
      ii. at least 95% CD105+ cells; and
      iii. at least 95% CD166+ cells; and
   (b) are capable of inhibiting IL2Rα expression by CD3/CD28-activated PBMCs by at least 30% relative to a control.

2. The MSC preparation of claim 1, wherein the MSCs express at least 13 pg TNFR1 per million MSCs.

3. The MSC preparation of claim 1, wherein the MSCs express at least 108 pg TNFR1 per million MSCs.

4. The MSC preparation of claim 1, wherein the MSCs express about 13 pg to about 179 pg TNFR1 per million MSCs.

5. The MSC preparation of claim 1, wherein the MSCs express 108 pg to 368 pg TNFR1 per million MSCs.

6. The MSC preparation of claim 1, wherein the MSCs express TNFR1 at a minimum of 272 pg/mL and a maximum of 1471 pg/mL.

7. A frozen cell suspension composition comprising:
   (a) cultured human bone-marrow-derived MSCs expanded from a cryopreserved in-process intermediate MSC preparation with an antigen profile comprising: i. less than 0.75% CD45+ cells; ii. at least 95% CD105+ cells; and iii. at least 95% CD166+ cells; wherein the cultured human bone-marrow-derived MSCs are capable of inhibiting IL2Ra expression by CD3/CD28-activated PBMCs by at least 30% relative to a control;
   (b) an electrolyte solution,
   (c) 5% human serum albumin, and
   (d) 10% DMSO.

8. A method of treating steroid refractory acute Graft versus Host Disease (aGvHD) in a pediatric patient comprising intravenously administering eight biweekly therapeutic doses of $2\times10^6$ mesenchymal stem cells/kg.

9. The method of claim 8, wherein the MSCs express at least 13 pg TNFR1 per million MSCs.

10. The method of claim 8, wherein the MSCs express at least 108 pg TNFR1 per million MSCs.

11. The method of claim 8, wherein the MSCs express about 13 pg to about 179 pg TNFR1 per million MSCs.

12. The method of claim 8, wherein the MSCs express about 13 pg to about 44 pg TNFR1 per million MSCs.

13. The method of claim 8, wherein the MSCs express 108 pg to 368 pg TNFR1 per million MSCs.

14. The method of claim 8, wherein the MSCs express TNFR1 at a minimum of 272 pg/mL and a maximum of 1471 pg/mL.

15. The method of claim 8, wherein the MSC are autologous.

16. The method of claim 8, wherein the MSC are allogeneic.

* * * * *